(12) United States Patent
Inouye et al.

(10) Patent No.: US 8,569,003 B2
(45) Date of Patent: Oct. 29, 2013

(54) FUSION PROTEIN HAVING LUMINESCENCE ACTIVITY

(71) Applicants: Satoshi Inouye, Tokyo (JP); Yuiko Sahara, Tokyo (JP); Junichi Sato, Tokyo (JP)

(72) Inventors: Satoshi Inouye, Tokyo (JP); Yuiko Sahara, Tokyo (JP); Junichi Sato, Tokyo (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 13/908,686

(22) Filed: Jun. 3, 2013

(65) Prior Publication Data

US 2013/0252256 A1    Sep. 26, 2013

Related U.S. Application Data

(62) Division of application No. 13/763,212, filed on Feb. 8, 2013, now Pat. No. 8,481,702, and a division of application No. 12/975,710, filed on Dec. 22, 2010, now Pat. No. 8,399,616.

(30) Foreign Application Priority Data

Dec. 24, 2009   (JP) ................. 2009-292779

(51) Int. Cl.
    *C12Q 1/66*    (2006.01)
(52) U.S. Cl.
    USPC .......................................................... 435/8
(58) Field of Classification Search
    USPC .......................................................... 435/8
    See application file for complete search history.

(56) References Cited

U.S. PATENT DOCUMENTS 6,232,107 B1   5/2001   Bryan et al.
7,834,148 B2   11/2010  Gambhir et al.

FOREIGN PATENT DOCUMENTS

| GB | 2442118 A | 3/2008 |
| GB | 2468757 A | 9/2010 |
| JP | 2008297203 A | 12/2008 |
| WO | 99/49019 A2 | 9/1999 |
| WO | 2010/042904 A2 | 4/2010 |

OTHER PUBLICATIONS

Inouye, S. and Sahara, Y., 2008, Identification of two catalytic domains in a luciferase secreted by the copepod *Gaussia princeps*, Biochemical and Biophysical Research Communications, vol. 365, Issue 1, 4, Jan. 2008, pp. 96-101.

Verhaegen, Monique and Theodore K. Christopoulos, Recombinant Gaussia Luciferase. Overexpression, Purification, and Analytical Application of a Bioluminescent Reporter for DNA Hybridization, Anal. Chem., 2002, 74 (17), pp. 4378-4385.

Lewis, J.C., and S. Daunert, 2001, Bioluminescence immunoassay for thyroxine employing genetically engineered mutant aequorins containing unique cysteine residues, Anal. Chem., vol. 73, 3227-3233.

Inouye, S. and Y. Sahara, 2008, Soluble protein expression in *E. coli* cells using IgG-binding domain of protein A as a solubilizing partner in the cold induced system, Biochem. & Biophys. Res. Com., 376, 448-453.

Patel, K.G. et al., 2009, Cell-free production of *Gaussia princeps* luciferase—antibody fragment bioconjugates for ex vivo detection of tumour cells, Biochem. & Biophys. Res. Com., 390, 971-976.

UK Search report, May 24, 2011.

*Primary Examiner* — Maryam Monshipouri
(74) *Attorney, Agent, or Firm* — Hogan Lovells US LLP

(57) ABSTRACT

The fusion protein comprising (1) a first region comprising the amino acid sequence of SEQ ID NO: 18 and (2) a second region comprising an amino acid sequence for a polypeptide containing at least one cysteine residue for binding to other useful compound via the thiol group can be modified by chemical modification, and thus has a high catalytic ability for a luminescence activity and is highly available for general purposes.

4 Claims, 14 Drawing Sheets

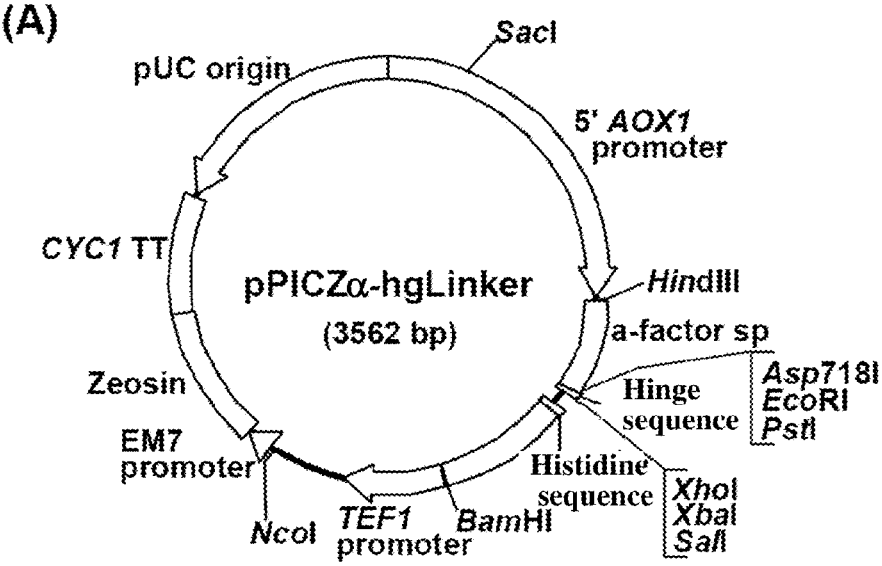

(B)

```
 [M   R   F   P   S   I   F   T   A   V   L   F   A   A   S   S
 ATG AGA TTT CCT TCA ATT TTT ACT GCT GTT TTA TTC GCA GCA TCC TCC

A   L   A   A   P   V   N   T   T   T   E   D   E   T   A   Q
 GCA TTA GCT GCT CCA GTC AAC ACT ACA ACA GAA GAT GAA ACG GCA CAA
                         α-factor signal peptide
  I   P   A   E   A   V   I   G   Y   S   D   L   E   G   D   F
 ATT CCG GCT GAA GCT GTC ATC GGT TAC TCA GAT TTA GAA GGG GAT TTC D   V   A   V   L   P   F   S   N   S   T   N   N   G   L   L
 GAT GTT GCT GTT TTG CCA TTT TCC AAC AGC ACA AAT AAC GGG TTA TTG F   I   N   T   T   I   A   S   I   A   A   K   E   E   G   V
 TTT ATA AAT ACT ACT ATT GCC AGC ATT GCT GCT AAA GAA GAA GGG GTA S   L   E   K   R   E   A   E]  G   T   E   F   L   Q   S
 TCT CTC GAA AAA AGA GAG GCT GAA GCT GGT ACC GAA TTC CTG CAG agc
                                       Asp718I  EcoRI   PstI
  L   S   T   P   P   T   P   S   P   S   T   P   P   C   L   E
 tta tcc acc ccg acg ccg tcc ccg tcc acc ccg ccg Tgc CTC GAG
                      Hinge sequence                      XhoI
  S   R   V   D   H   H   H   H   H   H   ***
 TCT AGA GTC GAC CAT CAT CAT CAT CAT CAT TGA
 XbaI       SalI      Histidine sequence
```

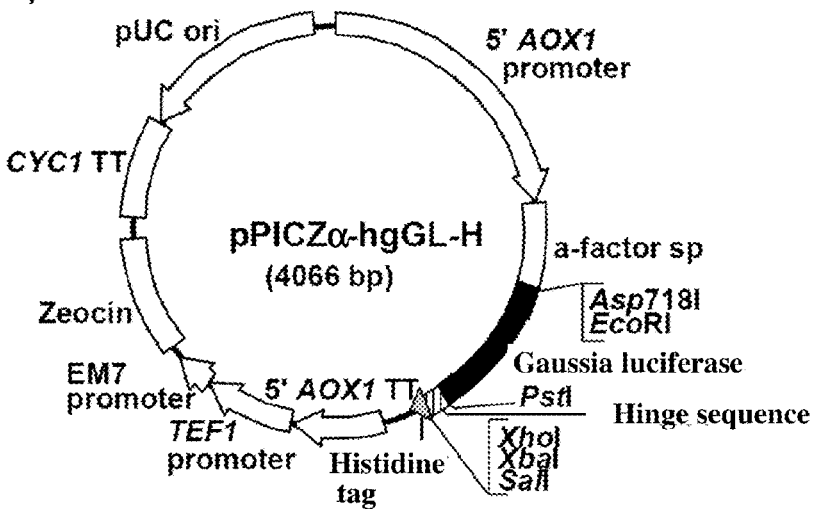

(B)

```
     [M    R    F    P    S    I    F    T    A    V    L    F    A    A    S    S
      ATG  AGA  TTT  CCT  TCA  ATT  TTT  ACT  GCT  GTT  TTA  TTC  GCA  GCA  TCC  TCC

A    L    A    A    P    V    N    T    T    T    E    D    E    T    A    Q
      GCA  TTA  GCT  GCT  CCA  GTC  AAC  ACT  ACA  ACA  GAA  GAT  GAA  ACG  GCA  CAA
                          α-factor signal peptide
      I    P    A    E    A    V    I    G    Y    S    D    L    E    G    D    F
      ATT  CCG  GCT  GAA  GCT  GTC  ATC  GGT  TAC  TCA  GAT  TTA  GAA  GGG  GAT  TTC D    V    A    V    L    P    F    S    N    S    T    N    N    G    L    L
      GAT  GTT  GCT  GTT  TTG  CCA  TTT  TCC  AAC  AGC  ACA  AAT  AAC  GGG  TTA  TTG F    I    N    T    T    I    A    S    I    A    A    K    E    E    G    V
      TTT  ATA  AAT  ACT  ACT  ATT  GCC  AGC  ATT  GCT  GCT  AAA  GAA  GAA  GGG  GTA S    L    E    K    R    E    A    E    A]   G    T    E    F    K    P    T
      TCT  CTC  GAA  AAA  AGA  GAG  GCT  GAA  GCT  GGT  ACC  GAA  TTC  AAG  CCC  ACC
                                                       Asp718I    EcoRI
      E    N    G    A    G    G    D    L    Q    S    L    S    T    P    P
      GAG  AAC  GGC  GCC  GGT  GGT  GAC  CTG  CAG  agc  tta  tcc  acc  ccg  ccg
              Gaussia luciferase          PstI         Hinge sequence
      T    P    S    P    S    T    P    P    C    L    E    S    R    V    D
      acc  ccg  tcc  ccg  tcc  acc  ccg  ccg  TGc  CTC  GAG  TCT  AGA  GTC  GAC
                                                       XhoI  XbaI      SalI
      H    H    H    H    H    H    ***
      CAT  CAT  CAT  CAT  CAT  CAT  TGA
          Histidine sequence
```

Fig. 4

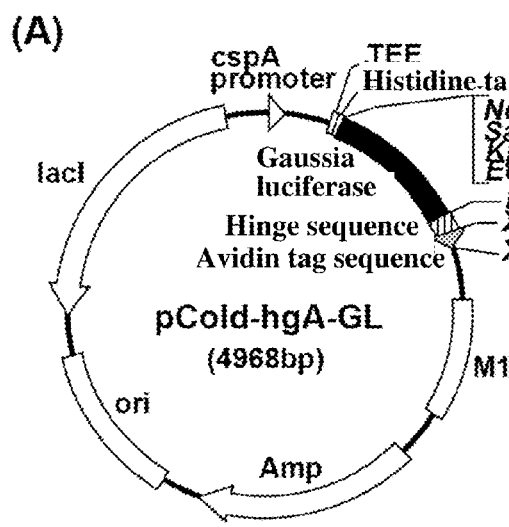

(A)

(B)
```
                        M   N   H   K   V   H   H   H   H   H   H   M
AAG AGG TAA TAC ACC ATG AAT CAC AAA GTG CAT CAT CAT CAT CAT CAT ATG
 SD                                     Histidine sequence        NdeI E   L   G   T   E   F   K   P   T   E   N  ...  G   A   G   G   D
GAG CTC GGT ACC GAA TTC AAG CCC ACC GAG AAC ... GGG GCC GGT GGT GAC
 SacI    Asp718I EcoRI           Gaussia luciferase L   Q   S   L   S   T   P   P   T   P   S   P   S   T   P   P   C
CTG CAG AGC TTA TCC ACC CCG CCG ACC CCG TCC CCG TCC ACC CCG CCG TGC
 PstI                       Hinge sequence L   E   G   L   N   D   I   F   E   A   Q   K   I   E   W   H   E
CTC GAG GGT CTG AAC GAC ATC TTC GAA GCT CAG AAA ATC GAA TGG CAC GAA
 XhoI                       Avidin tag sequence S   R   *
TCT AGA TAG
 XbaI
```

(a)

(b)

MNHKV|HHHHHH|MELGTLEGSEF|KPTEN...GAGGDLETSDFD...GGAVP
  Histidine tag         Gaussia luciferase      Apoaequorin-S142C
                           (168 a.a.)               (186 a.a.)

SEQUENCE LISTING

```
<160> NUMBER OF SEQ ID NOS: 28

<210> SEQ ID NO 1
<211> LENGTH: 369
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(369)

<400> SEQUENCE: 1 atg aga ttt cct tca att ttt act gct gtt tta ttc gca gca tcc tcc      48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gaa aaa aga gag gct gaa gct ggt acc gaa ttc ctg cag agc     288
Ser Leu Glu Lys Arg Glu Ala Glu Ala Gly Thr Glu Phe Leu Gln Ser
                85                  90                  95 tta tcc acc ccg ccg acc ccg tcc ccg tcc acc ccg ccg tgc ctc gag     336
Leu Ser Thr Pro Pro Thr Pro Ser Pro Ser Thr Pro Pro Cys Leu Glu
            100                 105                 110 tct aga gtc gac cat cat cat cat cat cat tga                         369
Ser Arg Val Asp His His His His His His
        115                 120

<210> SEQ ID NO 2
<211> LENGTH: 122
<212> TYPE: PRT
<213> ORGANISM: Artificial sequence
<220> FEATURE:
<223> OTHER INFORMATION: Synthetic Construct

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60
```

```
Phe Ile Asn Thr Thr Ile Ala Ser Ile Ala Ala Lys Glu Glu Gly Val
 65                  70                  75                  80

Ser Leu Glu Lys Arg Glu Ala Glu Ala Gly Thr Glu Phe Leu Gln Ser
             85                  90                  95

Leu Ser Thr Pro Pro Thr Pro Ser Pro Ser Thr Pro Pro Cys Leu Glu
            100                 105                 110

Ser Arg Val Asp His His His His His His
        115                 120

<210> SEQ ID NO 3
<211> LENGTH: 873
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(873)

<400> SEQUENCE: 3 atg aga ttt cct tca att ttt act gct gtt tta ttc gca gca tcc tcc      48
Met Arg Phe Pro Ser Ile Phe Thr Ala Val Leu Phe Ala Ala Ser Ser
  1               5                  10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
             20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
         35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
     50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
 65                  70                  75                  80 tct ctc gaa aaa aga gag gct gaa gct ggt acc gaa ttc aag ccc acc     288
Ser Leu Glu Lys Arg Glu Ala Glu Ala Gly Thr Glu Phe Lys Pro Thr
             85                  90                  95 gag aac aac gaa gac ttc aac atc gtg gcc gtg gcc agc aac ttc gcg     336
Glu Asn Asn Glu Asp Phe Asn Ile Val Ala Val Ala Ser Asn Phe Ala
            100                 105                 110 acc acg gat ctc gat gct gac cgc ggg aag ttg ccc ggc aag aag ctg     384
Thr Thr Asp Leu Asp Ala Asp Arg Gly Lys Leu Pro Gly Lys Lys Leu
        115                 120                 125 ccg ctg gag gtg ctc aaa gag atg gaa gcc aat gcc cgg aaa gct ggc     432
Pro Leu Glu Val Leu Lys Glu Met Glu Ala Asn Ala Arg Lys Ala Gly
    130                 135                 140 tgc acc agg ggc tgt ctg atc tgc ctg tcc cac atc aag tgc acg ccc     480
Cys Thr Arg Gly Cys Leu Ile Cys Leu Ser His Ile Lys Cys Thr Pro
145                 150                 155                 160 aag atg aag aag ttc atc cca gga cgc tgc cac acc tac gaa ggc gac     528
Lys Met Lys Lys Phe Ile Pro Gly Arg Cys His Thr Tyr Glu Gly Asp
                165                 170                 175 aaa gag tcc gca cag ggc ggc ata ggc gag gcg atc gtc gac att cct     576
Lys Glu Ser Ala Gln Gly Gly Ile Gly Glu Ala Ile Val Asp Ile Pro
            180                 185                 190 gag att cct ggg ttc aag gac ttg gag ccc atg gag cag ttc atc gca     624
Glu Ile Pro Gly Phe Lys Asp Leu Glu Pro Met Glu Gln Phe Ile Ala
        195                 200                 205 cag gtc gat ctg tgt gtg gac tgc aca act ggc tgc ctc aaa ggg ctt     672
Gln Val Asp Leu Cys Val Asp Cys Thr Thr Gly Cys Leu Lys Gly Leu
```

```
                    210                 215                 220
gcc aac gtg cag tgt tct gac ctg ctc aag aag tgg ctg ccg caa cgc         720
Ala Asn Val Gln Cys Ser Asp Leu Leu Lys Lys Trp Leu Pro Gln Arg
225                 230                 235                 240 tgt gcg acc ttt gcc agc aag atc cag ggc cag gtg gac aag atc aag         768
Cys Ala Thr Phe Ala Ser Lys Ile Gln Gly Gln Val Asp Lys Ile Lys
                245                 250                 255 ggg gcc ggt ggt gac ctg cag agc tta tcc acc ccg acc ccg tcc             816
Gly Ala Gly Gly Asp Leu Gln Ser Leu Ser Thr Pro Thr Pro Ser
            260                 265                 270 ccg tcc acc ccg ccg tgc ctc gag tct aga gtc gac cat cat cat cat         864
Pro Ser Thr Pro Pro Cys Leu Glu Ser Arg Val Asp His His His His
        275                 280                 285 cat cat tga                                                             873
His His
    290

<210> SEQ ID NO 4
<211> LENGTH: 290
<212> TYPE: PRT
<213> ORGANISM: Artificial sequence
<220> FEATURE:
<223> OTHER INFORMATION: Synthetic Construct

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gly Thr Glu Phe Lys Pro Thr
                85                  90                  95

Glu Asn Asn Glu Asp Phe Asn Ile Val Ala Val Ala Ser Asn Phe Ala
            100                 105                 110

Thr Thr Asp Leu Asp Ala Asp Arg Gly Lys Leu Pro Gly Lys Lys Leu
        115                 120                 125

Pro Leu Glu Val Leu Lys Glu Met Glu Ala Asn Ala Arg Lys Ala Gly
    130                 135                 140

Cys Thr Arg Gly Cys Leu Ile Cys Leu Ser His Ile Lys Cys Thr Pro
145                 150                 155                 160

Lys Met Lys Lys Phe Ile Pro Gly Arg Cys His Thr Tyr Glu Gly Asp
                165                 170                 175

Lys Glu Ser Ala Gln Gly Gly Ile Gly Glu Ala Ile Val Asp Ile Pro
            180                 185                 190

Glu Ile Pro Gly Phe Lys Asp Leu Glu Pro Met Glu Gln Phe Ile Ala
        195                 200                 205

Gln Val Asp Leu Cys Val Asp Cys Thr Thr Gly Cys Leu Lys Gly Leu
    210                 215                 220

Ala Asn Val Gln Cys Ser Asp Leu Leu Lys Lys Trp Leu Pro Gln Arg
225                 230                 235                 240

Cys Ala Thr Phe Ala Ser Lys Ile Gln Gly Gln Val Asp Lys Ile Lys
                245                 250                 255
```

```
Gly Ala Gly Gly Asp Leu Gln Ser Leu Ser Thr Pro Pro Thr Pro Ser
            260                 265                 270

Pro Ser Thr Pro Pro Cys Leu Glu Ser Arg Val Asp His His His His
        275                 280                 285

His His
    290

<210> SEQ ID NO 5
<211> LENGTH: 624
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(624)

<400> SEQUENCE: 5 atg aat cac aaa gtg cat cat cat cat cat cat atg gag ctc ggt acc      48
Met Asn His Lys Val His His His His His His Met Glu Leu Gly Thr
1               5                   10                  15 gaa ttc aag ccc acc gag aac aac gaa gac ttc aac atc gtg gcc gtg      96
Glu Phe Lys Pro Thr Glu Asn Asn Glu Asp Phe Asn Ile Val Ala Val
            20                  25                  30 gcc agc aac ttc gcg acc acg gat ctc gat gct gac cgc ggg aag ttg     144
Ala Ser Asn Phe Ala Thr Thr Asp Leu Asp Ala Asp Arg Gly Lys Leu
        35                  40                  45 ccc ggc aag aag ctg ccg ctg gag gtg ctc aaa gag atg gaa gcc aat     192
Pro Gly Lys Lys Leu Pro Leu Glu Val Leu Lys Glu Met Glu Ala Asn
    50                  55                  60 gcc cgg aaa gct ggc tgc acc agg ggc tgt ctg atc tgc ctg tcc cac     240
Ala Arg Lys Ala Gly Cys Thr Arg Gly Cys Leu Ile Cys Leu Ser His
65                  70                  75                  80 atc aag tgc acg ccc aag atg aag aag ttc atc cca gga cgc tgc cac     288
Ile Lys Cys Thr Pro Lys Met Lys Lys Phe Ile Pro Gly Arg Cys His
                85                  90                  95 acc tac gaa ggc gac aaa gag tcc gca cag ggc ggc ata ggc gag gcg     336
Thr Tyr Glu Gly Asp Lys Glu Ser Ala Gln Gly Gly Ile Gly Glu Ala
            100                 105                 110 atc gtc gac att cct gag att cct ggg ttc aag gac ttg gag ccc atg     384
Ile Val Asp Ile Pro Glu Ile Pro Gly Phe Lys Asp Leu Glu Pro Met
        115                 120                 125 gag cag ttc atc gca cag gtc gat ctg tgt gtg gac tgc aca act ggc     432
Glu Gln Phe Ile Ala Gln Val Asp Leu Cys Val Asp Cys Thr Thr Gly
    130                 135                 140 tgc ctc aaa ggg ctt gcc aac gtg cag tgt tct gac ctg ctc aag aag     480
Cys Leu Lys Gly Leu Ala Asn Val Gln Cys Ser Asp Leu Leu Lys Lys
145                 150                 155                 160 tgg ctg ccg caa cgc tgt gcg acc ttt gcc agc aag atc cag ggc cag     528
Trp Leu Pro Gln Arg Cys Ala Thr Phe Ala Ser Lys Ile Gln Gly Gln
                165                 170                 175 gtg gac aag atc aag ggg gcc ggt ggt gac ctg cag agc tta tcc acc     576
Val Asp Lys Ile Lys Gly Ala Gly Gly Asp Leu Gln Ser Leu Ser Thr
            180                 185                 190 ccg ccg acc ccg tcc ccg tcc acc ccg ccg tgc ctc gag tct aga tag    624
Pro Pro Thr Pro Ser Pro Ser Thr Pro Pro Cys Leu Glu Ser Arg
        195                 200                 205

<210> SEQ ID NO 6
<211> LENGTH: 207
<212> TYPE: PRT
<213> ORGANISM: Artificial sequence
<220> FEATURE:
```

<223> OTHER INFORMATION: Synthetic Construct

<400> SEQUENCE: 6

```
Met Asn His Lys Val His His His His His Met Glu Leu Gly Thr
1               5                   10                  15

Glu Phe Lys Pro Thr Glu Asn Asn Glu Asp Phe Asn Ile Val Ala Val
            20                  25                  30

Ala Ser Asn Phe Ala Thr Thr Asp Leu Asp Ala Asp Arg Gly Lys Leu
        35                  40                  45

Pro Gly Lys Lys Leu Pro Leu Glu Val Leu Lys Glu Met Glu Ala Asn
    50                  55                  60

Ala Arg Lys Ala Gly Cys Thr Arg Gly Cys Leu Ile Cys Leu Ser His
65                  70                  75                  80

Ile Lys Cys Thr Pro Lys Met Lys Lys Phe Ile Pro Gly Arg Cys His
                85                  90                  95

Thr Tyr Glu Gly Asp Lys Glu Ser Ala Gln Gly Gly Ile Gly Glu Ala
            100                 105                 110

Ile Val Asp Ile Pro Glu Ile Pro Gly Phe Lys Asp Leu Glu Pro Met
        115                 120                 125

Glu Gln Phe Ile Ala Gln Val Asp Leu Cys Val Asp Cys Thr Thr Gly
    130                 135                 140

Cys Leu Lys Gly Leu Ala Asn Val Gln Cys Ser Asp Leu Leu Lys Lys
145                 150                 155                 160

Trp Leu Pro Gln Arg Cys Ala Thr Phe Ala Ser Lys Ile Gln Gly Gln
                165                 170                 175

Val Asp Lys Ile Lys Gly Ala Gly Gly Asp Leu Gln Ser Leu Ser Thr
            180                 185                 190

Pro Pro Thr Pro Ser Pro Ser Thr Pro Pro Cys Leu Glu Ser Arg
        195                 200                 205
```

<210> SEQ ID NO 7
<211> LENGTH: 669
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(669)

<400> SEQUENCE: 7

```
atg aat cac aaa gtg cat cat cat cat cat cat atg gag ctc ggt acc       48
Met Asn His Lys Val His His His His His His Met Glu Leu Gly Thr
1               5                   10                  15 gaa ttc aag ccc acc gag aac aac gaa gac ttc aac atc gtg gcc gtg       96
Glu Phe Lys Pro Thr Glu Asn Asn Glu Asp Phe Asn Ile Val Ala Val
            20                  25                  30 gcc agc aac ttc gcg acc acg gat ctc gat gct gac cgc ggg aag ttg      144
Ala Ser Asn Phe Ala Thr Thr Asp Leu Asp Ala Asp Arg Gly Lys Leu
        35                  40                  45 ccc ggc aag aag ctg ccg ctg gag gtg ctc aaa gag atg gaa gcc aat      192
Pro Gly Lys Lys Leu Pro Leu Glu Val Leu Lys Glu Met Glu Ala Asn
    50                  55                  60 gcc cgg aaa gct ggc tgc acc agg ggc tgt ctg atc tgc ctg tcc cac      240
Ala Arg Lys Ala Gly Cys Thr Arg Gly Cys Leu Ile Cys Leu Ser His
65                  70                  75                  80 atc aag tgc acg ccc aag atg aag aag ttc atc cca gga cgc tgc cac      288
Ile Lys Cys Thr Pro Lys Met Lys Lys Phe Ile Pro Gly Arg Cys His
                85                  90                  95
```

| | | | | | | | | | | | | | | | | |
|---|---|---|---|---|---|---|---|---|---|---|---|---|---|---|---|---|
| acc | tac | gaa | ggc | gac | aaa | gag | tcc | gca | cag | ggc | gga | ata | ggc | gag | gcg | 336 |
| Thr | Tyr | Glu | Gly | Asp | Lys | Glu | Ser | Ala | Gln | Gly | Gly | Ile | Gly | Glu | Ala | |
| | | | 100 | | | | 105 | | | | 110 | | | | | |
| atc | gtc | gac | att | cct | gag | att | cct | ggg | ttc | aag | gac | ttg | gag | ccc | atg | 384 |
| Ile | Val | Asp | Ile | Pro | Glu | Ile | Pro | Gly | Phe | Lys | Asp | Leu | Glu | Pro | Met | |
| | | 115 | | | | | 120 | | | | | 125 | | | | |
| gag | cag | ttc | atc | gca | cag | gtc | gat | ctg | tgt | gtg | gac | tgc | aca | act | ggc | 432 |
| Glu | Gln | Phe | Ile | Ala | Gln | Val | Asp | Leu | Cys | Val | Asp | Cys | Thr | Thr | Gly | |
| | 130 | | | | | 135 | | | | | 140 | | | | | |
| tgc | ctc | aaa | ggg | ctt | gcc | aac | gtg | cag | tgt | tct | gac | ctg | ctc | aag | aag | 480 |
| Cys | Leu | Lys | Gly | Leu | Ala | Asn | Val | Gln | Cys | Ser | Asp | Leu | Leu | Lys | Lys | |
| 145 | | | | | 150 | | | | | 155 | | | | | 160 | |
| tgg | ctg | ccg | caa | cgc | tgt | gcg | acc | ttt | gcc | agc | aag | atc | cag | ggc | cag | 528 |
| Trp | Leu | Pro | Gln | Arg | Cys | Ala | Thr | Phe | Ala | Ser | Lys | Ile | Gln | Gly | Gln | |
| | | | | 165 | | | | | 170 | | | | | 175 | | |
| gtg | gac | aag | atc | aag | ggg | gcc | ggt | ggt | gac | ctg | cag | agc | tta | tcc | acc | 576 |
| Val | Asp | Lys | Ile | Lys | Gly | Ala | Gly | Gly | Asp | Leu | Gln | Ser | Leu | Ser | Thr | |
| | | | 180 | | | | | 185 | | | | | 190 | | | |
| ccg | acc | ccg | tcc | ccg | tcc | acc | ccg | ccg | tgc | ctc | gag | ggt | ctg | aac | | 624 |
| Pro | Pro | Thr | Pro | Ser | Pro | Ser | Thr | Pro | Pro | Cys | Leu | Glu | Gly | Leu | Asn | |
| | | 195 | | | | | 200 | | | | | 205 | | | | |
| gac | atc | ttc | gaa | gct | cag | aaa | atc | gaa | tgg | cac | gaa | tct | aga | tag | | 669 |
| Asp | Ile | Phe | Glu | Ala | Gln | Lys | Ile | Glu | Trp | His | Glu | Ser | Arg | | | |
| | 210 | | | | | 215 | | | | | 220 | | | | | |

<210> SEQ ID NO 8
<211> LENGTH: 222
<212> TYPE: PRT
<213> ORGANISM: Artificial sequence
<220> FEATURE:
<223> OTHER INFORMATION: Synthetic Construct

<400> SEQUENCE: 8

Met Asn His Lys Val His His His His His Met Glu Leu Gly Thr
1               5                   10                  15

Glu Phe Lys Pro Thr Glu Asn Asn Glu Asp Phe Asn Ile Val Ala Val
            20                  25                  30

Ala Ser Asn Phe Ala Thr Thr Asp Leu Asp Ala Asp Arg Gly Lys Leu
        35                  40                  45

Pro Gly Lys Lys Leu Pro Leu Glu Val Leu Lys Glu Met Glu Ala Asn
    50                  55                  60

Ala Arg Lys Ala Gly Cys Thr Arg Gly Cys Leu Ile Cys Leu Ser His
65                  70                  75                  80

Ile Lys Cys Thr Pro Lys Met Lys Lys Phe Ile Pro Gly Arg Cys His
                85                  90                  95

Thr Tyr Glu Gly Asp Lys Glu Ser Ala Gln Gly Gly Ile Gly Glu Ala
            100                 105                 110

Ile Val Asp Ile Pro Glu Ile Pro Gly Phe Lys Asp Leu Glu Pro Met
        115                 120                 125

Glu Gln Phe Ile Ala Gln Val Asp Leu Cys Val Asp Cys Thr Thr Gly
    130                 135                 140

Cys Leu Lys Gly Leu Ala Asn Val Gln Cys Ser Asp Leu Leu Lys Lys
145                 150                 155                 160

Trp Leu Pro Gln Arg Cys Ala Thr Phe Ala Ser Lys Ile Gln Gly Gln
                165                 170                 175

Val Asp Lys Ile Lys Gly Ala Gly Gly Asp Leu Gln Ser Leu Ser Thr
            180                 185                 190

Pro Pro Thr Pro Ser Pro Ser Thr Pro Pro Cys Leu Glu Gly Leu Asn
        195                 200                 205

Asp Ile Phe Glu Ala Gln Lys Ile Glu Trp His Glu Ser Arg
    210                 215                 220

<210> SEQ ID NO 9
<211> LENGTH: 54
<212> TYPE: DNA
<213> ORGANISM: Artificial sequence
<220> FEATURE:
<223> OTHER INFORMATION: synthetic DNA

<400> SEQUENCE: 9
tcgaaaaaag agaggctgaa gctggtaccg aattcctgca gctcgagtct agag        54

<210> SEQ ID NO 10
<211> LENGTH: 54
<212> TYPE: DNA
<213> ORGANISM: Artificial sequence
<220> FEATURE:
<223> OTHER INFORMATION: synthetic DNA

<400> SEQUENCE: 10
tcgactctag actcgagctg caggaattcg gtaccagctt cagcctctct tttt        54

<210> SEQ ID NO 11
<211> LENGTH: 59
<212> TYPE: DNA
<213> ORGANISM: Artificial sequence
<220> FEATURE:
<223> OTHER INFORMATION: synthetic DNA

<400> SEQUENCE: 11
gagcttatcc accccgccga ccccgtcccc gtccaccccg ccgtgcctcg agtctagag    59

<210> SEQ ID NO 12
<211> LENGTH: 67
<212> TYPE: DNA
<213> ORGANISM: Artificial sequence
<220> FEATURE:
<223> OTHER INFORMATION: synthetic DNA

<400> SEQUENCE: 12
tcgactctag actcgaggca cggcggggtg acggggacg gggtcggcgg ggtggataag   60
ctctgca                                                            67

<210> SEQ ID NO 13
<211> LENGTH: 30
<212> TYPE: DNA
<213> ORGANISM: Artificial sequence
<220> FEATURE:
<223> OTHER INFORMATION: synthetic DNA

<400> SEQUENCE: 13
gccgaattca agcccaccga gaacaacgaa                                   30

<210> SEQ ID NO 14
<211> LENGTH: 30
<212> TYPE: DNA
<213> ORGANISM: Artificial sequence
<220> FEATURE:
<223> OTHER INFORMATION: synthetic DNA

<400> SEQUENCE: 14
ggcctgcagg tcaccaccgg cccccttgat                                   30

<210> SEQ ID NO 15

```
<211> LENGTH: 51
<212> TYPE: DNA
<213> ORGANISM: Artificial sequence
<220> FEATURE:
<223> OTHER INFORMATION: synthetic DNA

<400> SEQUENCE: 15
tcgagggtct gaacgacatc ttcgaagctc agaaaatcga atggcacgaa t          51

<210> SEQ ID NO 16
<211> LENGTH: 51
<212> TYPE: DNA
<213> ORGANISM: Artificial sequence
<220> FEATURE:
<223> OTHER INFORMATION: synthetic DNA

<400> SEQUENCE: 16
ctagattcgt gccattcgat tttctgagcc tcgaagatgt cgttcagacc c          51

<210> SEQ ID NO 17
<211> LENGTH: 504
<212> TYPE: DNA
<213> ORGANISM: Gaussia princeps
<220> FEATURE:
<221> NAME/KEY: CDS
<222> LOCATION: (1)..(504)

<400> SEQUENCE: 17 aag ccc acc gag aac aac gaa gac ttc aac atc gtg gcc gtg gcc agc      48
Lys Pro Thr Glu Asn Asn Glu Asp Phe Asn Ile Val Ala Val Ala Ser
 1               5                  10                  15 aac ttc gcg acc acg gat ctc gat gct gac cgc ggg aag ttg ccc ggc      96
Asn Phe Ala Thr Thr Asp Leu Asp Ala Asp Arg Gly Lys Leu Pro Gly
             20                  25                  30 aag aag ctg ccg ctg gag gtg ctc aaa gag atg gaa gcc aat gcc cgg     144
Lys Lys Leu Pro Leu Glu Val Leu Lys Glu Met Glu Ala Asn Ala Arg
         35                  40                  45 aaa gct ggc tgc acc agg ggc tgt ctg atc tgc ctg tcc cac atc aag     192
Lys Ala Gly Cys Thr Arg Gly Cys Leu Ile Cys Leu Ser His Ile Lys
     50                  55                  60 tgc acg ccc aag atg aag aag ttc atc cca gga cgc tgc cac acc tac     240
Cys Thr Pro Lys Met Lys Lys Phe Ile Pro Gly Arg Cys His Thr Tyr
 65                  70                  75                  80 gaa ggc gac aaa gag tcc gca cag ggc ggc ata ggc gag gcg atc gtc     288
Glu Gly Asp Lys Glu Ser Ala Gln Gly Gly Ile Gly Glu Ala Ile Val
                 85                  90                  95 gac att cct gag att cct ggg ttc aag gac ttg gag ccc atg gag cag     336
Asp Ile Pro Glu Ile Pro Gly Phe Lys Asp Leu Glu Pro Met Glu Gln
            100                 105                 110 ttc atc gca cag gtc gat ctg tgt gtg gac tgc aca act ggc tgc ctc     384
Phe Ile Ala Gln Val Asp Leu Cys Val Asp Cys Thr Thr Gly Cys Leu
        115                 120                 125 aaa ggg ctt gcc aac gtg cag tgt tct gac ctg ctc aag aag tgg ctg     432
Lys Gly Leu Ala Asn Val Gln Cys Ser Asp Leu Leu Lys Lys Trp Leu
    130                 135                 140 ccg caa cgc tgt gcg acc ttt gcc agc aag atc cag ggc cag gtg gac     480
Pro Gln Arg Cys Ala Thr Phe Ala Ser Lys Ile Gln Gly Gln Val Asp
145                 150                 155                 160 aag atc aag ggg gcc ggt ggt gac                                     504
Lys Ile Lys Gly Ala Gly Gly Asp
                165

<210> SEQ ID NO 18
<211> LENGTH: 168
```

```
<212> TYPE: PRT
<213> ORGANISM: Gaussia princeps

<400> SEQUENCE: 18

Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
            20                  25                  30

Lys Lys Leu Pro Leu Glu Val Leu Lys Glu Met Glu Ala Asn Ala Arg
        35                  40                  45

Lys Ala Gly Cys Thr Arg Gly Cys Leu Ile Cys Leu Ser His Ile Lys
    50                  55                  60

Cys Thr Pro Lys Met Lys Lys Phe Ile Pro Gly Arg Cys His Thr Tyr
65              70                  75                  80

Glu Gly Asp Lys Glu Ser Ala Gln Gly Ile Gly Glu Ala Ile Val
                85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
        115                 120                 125

Lys Gly Leu Ala Asn Val Gln Cys Ser Asp Leu Leu Lys Lys Trp Leu
    130                 135                 140

Pro Gln Arg Cys Ala Thr Phe Ala Ser Lys Ile Gln Gly Gln Val Asp
145             150                 155                 160

Lys Ile Lys Gly Ala Gly Gly Asp
                165

<210> SEQ ID NO 19
<211> LENGTH: 45
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(45)

<400> SEQUENCE: 19 agc tta tcc acc ccg ccg acc ccg tcc ccg tcc acc ccg ccg tgc      45
Ser Leu Ser Thr Pro Pro Thr Pro Ser Pro Ser Thr Pro Pro Cys
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Synthetic Construct

<400> SEQUENCE: 20

Ser Leu Ser Thr Pro Pro Thr Pro Ser Pro Ser Thr Pro Pro Cys
1               5                   10                  15

<210> SEQ ID NO 21
<211> LENGTH: 30
<212> TYPE: DNA
<213> ORGANISM: Artificial sequence
<220> FEATURE:
<223> OTHER INFORMATION: synthetic DNA

<400> SEQUENCE: 21
ccgctcgaga catcagactt cgacaaccca                                  30
```

```
<210> SEQ ID NO 22
<211> LENGTH: 21
<212> TYPE: DNA
<213> ORGANISM: Artificial sequence
<220> FEATURE:
<223> OTHER INFORMATION: synthetic DNA

<400> SEQUENCE: 22
atcttcgcat gattggatga t                                              21

<210> SEQ ID NO 23
<211> LENGTH: 21
<212> TYPE: DNA
<213> ORGANISM: Artificial sequence
<220> FEATURE:
<223> OTHER INFORMATION: synthetic DNA

<400> SEQUENCE: 23
caatcatgcg aagattgcga g                                              21

<210> SEQ ID NO 24
<211> LENGTH: 36
<212> TYPE: DNA
<213> ORGANISM: Artificial sequence
<220> FEATURE:
<223> OTHER INFORMATION: synthetic DNA

<400> SEQUENCE: 24
cggctgcagt tagggacag ctccaccgta gagctt                               36

<210> SEQ ID NO 25
<211> LENGTH: 33
<212> TYPE: DNA
<213> ORGANISM: Artificial sequence
<220> FEATURE:
<223> OTHER INFORMATION: synthetic DNA

<400> SEQUENCE: 25
ggcggtaccg aattcaagcc caccgagaac aac                                 33

<210> SEQ ID NO 26
<211> LENGTH: 30
<212> TYPE: DNA
<213> ORGANISM: Artificial sequence
<220> FEATURE:
<223> OTHER INFORMATION: synthetic DNA

<400> SEQUENCE: 26
ccgctcgagg tcaccaccgg cccccttgat                                     30

<210> SEQ ID NO 27
<211> LENGTH: 1137
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(1137)

<400> SEQUENCE: 27 atg aat cac aaa gtg cat cat cat cat cat cat atg gag ctc ggt acc    48
Met Asn His Lys Val His His His His His His Met Glu Leu Gly Thr
1               5                   10                  15 ctc gag gga tcc gaa ttc aag ccc acc gag aac aac gaa gac ttc aac    96
Leu Glu Gly Ser Glu Phe Lys Pro Thr Glu Asn Asn Glu Asp Phe Asn
            20                  25                  30
```

```
atc gtg gcc gtg gcc agc aac ttc gcg acc acg gat ctc gat gct gac      144
Ile Val Ala Val Ala Ser Asn Phe Ala Thr Thr Asp Leu Asp Ala Asp
         35                  40                  45 cgc ggg aag ttg ccc ggc aag aag ctg ccg ctg gag gtg ctc aaa gag      192
Arg Gly Lys Leu Pro Gly Lys Lys Leu Pro Leu Glu Val Leu Lys Glu
 50                  55                  60 atg gaa gcc aat gcc cgg aaa gct ggc tgc acc agg ggc tgt ctg atc      240
Met Glu Ala Asn Ala Arg Lys Ala Gly Cys Thr Arg Gly Cys Leu Ile
65                  70                  75                  80 tgc ctg tcc cac atc aag tgc acg ccc aag atg aag aag ttc atc cca      288
Cys Leu Ser His Ile Lys Cys Thr Pro Lys Met Lys Lys Phe Ile Pro
                 85                  90                  95 gga cgc tgc cac acc tac gaa ggc gac aaa gag tcc gca cag ggc ggc      336
Gly Arg Cys His Thr Tyr Glu Gly Asp Lys Glu Ser Ala Gln Gly Gly
            100                 105                 110 ata ggc gag gcg atc gtc gac att cct gag att cct ggg ttc aag gac      384
Ile Gly Glu Ala Ile Val Asp Ile Pro Glu Ile Pro Gly Phe Lys Asp
        115                 120                 125 ttg gag ccc atg gag cag ttc atc gca cag gtc gat ctg tgt gtg gac      432
Leu Glu Pro Met Glu Gln Phe Ile Ala Gln Val Asp Leu Cys Val Asp
    130                 135                 140 tgc aca act ggc tgc ctc aaa ggg ctt gcc aac gtg cag tgt tct gac      480
Cys Thr Thr Gly Cys Leu Lys Gly Leu Ala Asn Val Gln Cys Ser Asp
145                 150                 155                 160 ctg ctc aag aag tgg ctg ccg caa cgc tgt gcg acc ttt gcc agc aag      528
Leu Leu Lys Lys Trp Leu Pro Gln Arg Cys Ala Thr Phe Ala Ser Lys
                165                 170                 175 atc cag ggc cag gtg gac aag atc aag ggg gcc ggt ggt gac ctc gag      576
Ile Gln Gly Gln Val Asp Lys Ile Lys Gly Ala Gly Gly Asp Leu Glu
            180                 185                 190 aca tca gac ttc gac aac cca aga tgg att gga cga cac aag cat atg      624
Thr Ser Asp Phe Asp Asn Pro Arg Trp Ile Gly Arg His Lys His Met
        195                 200                 205 ttc aat ttc ctt gat gtc aac cac aat gga aaa atc tct ctt gac gag      672
Phe Asn Phe Leu Asp Val Asn His Asn Gly Lys Ile Ser Leu Asp Glu
    210                 215                 220 atg gtc tac aag gca tct gat att gtc atc aat aac ctt gga gca aca      720
Met Val Tyr Lys Ala Ser Asp Ile Val Ile Asn Asn Leu Gly Ala Thr
225                 230                 235                 240 cct gag caa gcc aaa cga cac aaa gat gct gta gaa gcc ttc ttc gga      768
Pro Glu Gln Ala Lys Arg His Lys Asp Ala Val Glu Ala Phe Phe Gly
                245                 250                 255 gga gct gga atg aaa tat ggt gtg gaa act gat tgg cct gca tat att      816
Gly Ala Gly Met Lys Tyr Gly Val Glu Thr Asp Trp Pro Ala Tyr Ile
            260                 265                 270 gaa gga tgg aaa aaa ttg gct act gat gaa ttg gag aaa tac gcc aaa      864
Glu Gly Trp Lys Lys Leu Ala Thr Asp Glu Leu Glu Lys Tyr Ala Lys
        275                 280                 285 aac gaa cca acg ctc atc cgt ata tgg ggt gat gct ttg ttt gat atc      912
Asn Glu Pro Thr Leu Ile Arg Ile Trp Gly Asp Ala Leu Phe Asp Ile
    290                 295                 300 gtt gac aaa gat caa aat gga gcc att aca ctg gat gaa tgg aaa gca      960
Val Asp Lys Asp Gln Asn Gly Ala Ile Thr Leu Asp Glu Trp Lys Ala
305                 310                 315                 320 tac acc aaa gct gct ggt atc atc caa tca tgc gaa gat tgc gag gaa     1008
Tyr Thr Lys Ala Ala Gly Ile Ile Gln Ser Cys Glu Asp Cys Glu Glu
                325                 330                 335 aca ttc aga gtg tgc gat att gat gaa agt gga caa ctc gat gtt gat     1056
Thr Phe Arg Val Cys Asp Ile Asp Glu Ser Gly Gln Leu Asp Val Asp
            340                 345                 350
```

-continued

```
gag atg aca aga caa cat tta gga ttt tgg tac acc atg gat cct gct    1104
Glu Met Thr Arg Gln His Leu Gly Phe Trp Tyr Thr Met Asp Pro Ala
        355                 360                 365 tgc gaa aag ctc tac ggt gga gct gtc ccc taa                        1137
Cys Glu Lys Leu Tyr Gly Gly Ala Val Pro
        370                 375
```

<210> SEQ ID NO 28
<211> LENGTH: 378
<212> TYPE: PRT
<213> ORGANISM: Artificial sequence
<220> FEATURE:
<223> OTHER INFORMATION: Synthetic Construct

<400> SEQUENCE: 28

```
Met Asn His Lys Val His His His His His Met Glu Leu Gly Thr
1               5                   10                  15

Leu Glu Gly Ser Glu Phe Lys Pro Thr Glu Asn Asn Glu Asp Phe Asn
                20                  25                  30

Ile Val Ala Val Ala Ser Asn Phe Ala Thr Thr Asp Leu Asp Ala Asp
                35                  40                  45

Arg Gly Lys Leu Pro Gly Lys Lys Leu Pro Leu Glu Val Leu Lys Glu
        50                  55                  60

Met Glu Ala Asn Ala Arg Lys Ala Gly Cys Thr Arg Gly Cys Leu Ile
65                  70                  75                  80

Cys Leu Ser His Ile Lys Cys Thr Pro Lys Met Lys Lys Phe Ile Pro
                85                  90                  95

Gly Arg Cys His Thr Tyr Glu Gly Asp Lys Glu Ser Ala Gln Gly Gly
                100                 105                 110

Ile Gly Glu Ala Ile Val Asp Ile Pro Glu Ile Pro Gly Phe Lys Asp
            115                 120                 125

Leu Glu Pro Met Glu Gln Phe Ile Ala Gln Val Asp Leu Cys Val Asp
        130                 135                 140

Cys Thr Thr Gly Cys Leu Lys Gly Leu Ala Asn Val Gln Cys Ser Asp
145                 150                 155                 160

Leu Leu Lys Lys Trp Leu Pro Gln Arg Cys Ala Thr Phe Ala Ser Lys
                165                 170                 175

Ile Gln Gly Gln Val Asp Lys Ile Lys Gly Ala Gly Gly Asp Leu Glu
            180                 185                 190

Thr Ser Asp Phe Asp Asn Pro Arg Trp Ile Gly Arg His Lys His Met
        195                 200                 205

Phe Asn Phe Leu Asp Val Asn His Asn Gly Lys Ile Ser Leu Asp Glu
    210                 215                 220

Met Val Tyr Lys Ala Ser Asp Ile Val Ile Asn Asn Leu Gly Ala Thr
225                 230                 235                 240

Pro Glu Gln Ala Lys Arg His Lys Asp Ala Val Glu Ala Phe Phe Gly
                245                 250                 255

Gly Ala Gly Met Lys Tyr Gly Val Glu Thr Asp Trp Pro Ala Tyr Ile
            260                 265                 270

Glu Gly Trp Lys Lys Leu Ala Thr Asp Glu Leu Glu Lys Tyr Ala Lys
        275                 280                 285

Asn Glu Pro Thr Leu Ile Arg Ile Trp Gly Asp Ala Leu Phe Asp Ile
    290                 295                 300

Val Asp Lys Asp Gln Asn Gly Ala Ile Thr Leu Asp Glu Trp Lys Ala
305                 310                 315                 320

Tyr Thr Lys Ala Ala Gly Ile Ile Gln Ser Cys Glu Asp Cys Glu Glu
```

-continued

```
                        325                     330                       335
Thr Phe Arg Val Cys Asp Ile Asp Glu Ser Gly Gln Leu Asp Val Asp
            340                     345                 350

Glu Met Thr Arg Gln His Leu Gly Phe Trp Tyr Thr Met Asp Pro Ala
            355                     360                 365

Cys Glu Lys Leu Tyr Gly Gly Ala Val Pro
    370                 375
```

FUSION PROTEIN HAVING LUMINESCENCE ACTIVITY

This application is a Divisional of U.S. application Ser. No. 13/763,212, filed on Feb. 8, 2013 now U.S. Pat. No. 8,481,702, which is a Divisional of U.S. application Ser. No. 12/975,710, filed on Dec. 22, 2010 now U.S. Pat. No. 8,399,616, which claims priority under 35 U.S.C. §119(a) on Patent Application No. 2009-292779 filed in Japan on Dec. 24, 2009; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a fusion protein, a polynucleotide, a recombinant vector, a transformant, a method for producing the fusion protein, a complex of the fusion protein to which other useful compound is bound, etc., which are described below.

BACKGROUND ART

Gaussia luciferase is a secretory enzyme produced from the deep-sea copepoda, Gaussia princeps, and the luminescence system catalyzed by Gaussia luciferase is simple and the luminescence reaction is performed only under the presence of oxygen and a substrate (a luciferin such as a coelenterazine, etc.).

By comparison with the luminescence reaction catalyzed by firefly luciferase, the luminescence reaction catalyzed by Gaussia luciferase is simple and emits strong blue light. On the other hand, firefly luciferase requires ATP and magnesium ions for the luminescence reaction. From this reason, Gaussia luciferase expects to be used in various applications in the future.

Gaussia luciferase is a simple protein having the signal peptide sequence of 17 amino acid residues at the amino terminus for secretion and the catalytic domain consisting of 168 amino acid residues. Gaussia luciferase is a unique luciferase having 10 cysteine residues in a molecule, in which the content of cysteines is approximately 6% in the total amino acid. It has been reported that an intramolecular —S—S— bond is critical to retain the catalytic ability for the luminescence activity of Gaussia luciferase. By treatment of Gaussia luciferase with reducing agents such as mercaptoethanol, dithiothreitol, etc., the luminescence activity of Gaussia luciferase was lost completely (Inouye, S. & Sahara, Y. (2008) Biochem. Biophys. Res. Commun. 365, 96-101.). However, there is little information on the positions of the intramolecular —S—S— bond or free thiol groups in Gaussia luciferase.

By the chemical modification of Gaussia luciferase with a ligand using the intramolecular thiol groups of Gaussia luciferase, namely, by introducing a ligand into Gaussia luciferase via thiol groups of amino acid residue in Gaussia luciferase, the ligand-conjugated Gaussia luciferase can be obtained. Using the ligand-conjugated Gaussia luciferase and relying on the luminescence reaction of Gaussia luciferase, it is considered to detect a substance capable of specifically binding to the ligand. However, there is no report so far on such a case that Gaussia luciferase was directly conjugated with the ligand by chemical modification.

The present inventors found that when a ligand is introduced into Gaussia luciferase via the thiol groups from the amino acids which constitute Gaussia luciferase, the catalytic ability of the ligand-conjugated Gaussia luciferase for the luminescence activity is markedly reduced. The inventors also attempted to introduce a ligand into Gaussia luciferase via amino groups or carboxyl groups, other than the thiol groups, derived from the amino acids which constitute Gaussia luciferase. However, the catalytic ability of Gaussia luciferase for the luminescence activity was likewise markedly reduced. As such, it was impossible to obtain the ligand-conjugated Gaussia luciferase by chemical modification while maintaining the original luminescence intensity of Gaussia luciferase. This is considered to be because the protein catalytic domains associated with the luminescence reaction of Gaussia luciferase would be affected by introducing the ligand via the thiol, amino or carboxyl groups derived from the amino acids in the molecule of Gaussia luciferase, and the luminescence reaction would be inhibited.

On the other hand, it is considered that when cysteine residues are introduced into the molecule or at the amino or carboxyl terminus of Gaussia luciferase, the formation of correct intramolecular —S—S— bonds by refolding of a protein expressed in cells would be hindered.

The only ligand-conjugated Gaussia luciferase reported is biotinylated Gaussia luciferase modified with a biotinylation enzyme. This luciferase was prepared by expressing the fused Gaussia luciferase gene having a modifiable biotin recognition sequence in *Escherichia coli* followed by biotinylation with an enzyme present in *E. coli* (Verhaegen, M. & Christopoulos, T. K. (2002) Anal. Chem. 74, 4378-4385.). According to an enzymatic modification in living cells as in this method, however, it is difficult to supply biotinylated Gaussia luciferase uniformly in large amounts. Furthermore, according to this method the ligand which can be introduced into Gaussia luciferase is biotin alone, but other ligands such as avidin, streptavidin, enzymes, antibodies, antigens, nucleic acids, polysaccharides, receptors or the like or fluorescent substances, etc. cannot be introduced into Gaussia luciferase. The ligand which can be introduced is biotin alone and its application is limited.

DISCLOSURE OF THE INVENTION

Under the circumstances described above, a luciferase which can be modified through chemical modification, has a high catalytic ability for the luminescence activity and is highly available for general purposes has been desired.

As a result of extensive studies to solve the foregoing problems, the present inventors found that a fusion protein comprising Gaussia luciferase and a polypeptide having at least one cysteine residue for binding to other useful compound via the thiol group is a luciferase which can be modified by chemical modification and has high availability for general purposes, while retaining the catalytic ability of Gaussia luciferase for the luminescence activity. Based on these findings, the inventors have continued further investigations and come to accomplish the present invention.

More specifically, the present invention provides a fusion protein, a polynucleotide, a recombinant vector, a transformant, a method for producing the fusion protein, a complex of the fusion protein and other useful compound, etc., which are described below.

[1] A fusion protein comprising:
(1) a first region selected from the group consisting of (a) to (d) below:
(a) a region consisting of the amino acid sequence of SEQ ID NO: 18;
(b) a region consisting of the amino acid sequence of SEQ ID NO: 18 wherein 1 or more amino acids are deleted, substituted, inserted and/or added and having a catalytic ability for a luminescence activity with a luciferin which is a substrate;
(c) a region consisting of an amino acid sequence having at least 70% homology to the amino acid sequence of SEQ ID NO: 18 and having a catalytic ability for a luminescence activity with a luciferin which is a substrate; and,
(d) a region consisting of an amino acid sequence encoded by a polynucleotide which hybridizes under stringent conditions to a polynucleotide consisting of a nucleotide sequence complementary to the nucleotide sequence of SEQ ID NO: 17 and having a catalytic ability for a luminescence activity with a luciferin which is a substrate; and,
(2) a second region consisting of an amino acid sequence for a polypeptide having at least one cysteine residue for binding to other useful compound via its thiol group.

[2] The fusion protein according to [1] above, wherein the second region is selected from the group consisting of (e) to (h) below:
(e) a region consisting of the amino acid sequence of SEQ ID NO: 20;
(f) a region comprising the amino acid sequence of SEQ ID NO: 20 wherein 1 or more amino acids are deleted, substituted, inserted and/or added and having at least one cysteine residue for binding to other useful compound via the thiol group;
(g) a region comprising an amino acid sequence having at least 70% homology to the amino acid sequence of SEQ ID NO: 20 and having at least one cysteine residue for binding to other useful compound via the thiol group; and,
(h) a region comprising an amino acid sequence encoded by a polynucleotide which hybridizes under stringent conditions to a polynucleotide consisting of a nucleotide sequence complementary to the nucleotide sequence of SEQ ID NO: 19 and having at least one cysteine residue for binding to other useful compound via the thiol group.

[3] The fusion protein according to [2] above, wherein the second region is selected from the group consisting of (e) to (h) below:
(e) a region consisting of the amino acid sequence of SEQ ID NO: 20;
(f) a region comprising the amino acid sequence of SEQ ID NO: 20 wherein 1 to 3 amino acids are deleted, substituted, inserted and/or added and having at least one cysteine residue for binding to other useful compound via the thiol group;
(g) a region comprising an amino acid sequence having at least 90% homology to the amino acid sequence of SEQ ID NO: 20 and having at least one cysteine residue for binding to other useful compound via the thiol group; and,
(h) a region comprising an amino acid sequence encoded by a polynucleotide which hybridizes under high stringent conditions to a polynucleotide consisting of a nucleotide sequence complementary to the nucleotide sequence of SEQ ID NO: 19 and having at least one cysteine residue for binding to other useful compound via the thiol group.

[4] The fusion protein according to any one of [1] to [3] above, wherein the first region is selected from the group consisting of (a) to (d) below:
(a) a region consisting of the amino acid sequence of SEQ ID NO: 18;
(b) a region consisting of the amino acid sequence of SEQ ID NO: 18 wherein 1 to 10 amino acids are deleted, substituted, inserted and/or added and having a catalytic ability for a luminescence activity with a luciferin which is a substrate;
(c) a region consisting of an amino acid sequence having at least 90% homology to the amino acid sequence of SEQ ID NO: 18 and having a catalytic ability for a luminescence activity with a luciferin which is a substrate; and,
(d) a region consisting of an amino acid sequence encoded by a polynucleotide which hybridizes under high stringent conditions to a polynucleotide consisting of a nucleotide sequence complementary to the nucleotide sequence of SEQ ID NO: 17 and having a catalytic ability for a luminescence activity with a luciferin which is a substrate.

[5] The fusion protein according to [4] above, wherein:
(1) the first region is a region consisting of the amino acid sequence of SEQ ID NO: 18, and,
(2) the second region is a region consisting of the amino acid sequence of SEQ ID NO: 20.

[6] The fusion protein according to any one of [1] to [5] above, further comprising an amino acid sequence for promoting translation and/or an amino acid sequence for purification.

[7] A fusion protein consisting of an amino acid sequence of SEQ ID NO: 4, 6 or 8.

[8] A polynucleotide comprising a polynucleotide encoding the fusion protein according to any one of [1] to [7] above.

[9] A polynucleotide comprising:
(1) a first coding sequence selected from the group consisting of (a) to (d) below:
(a) a coding sequence consisting of a polynucleotide consisting of the nucleotide sequence of SEQ ID NO: 17;
(b) a coding sequence consisting of a polynucleotide which hybridizes under stringent conditions to a polynucleotide consisting of a nucleotide sequence complementary to the nucleotide sequence of SEQ ID NO: 17 and encodes a region having a catalytic ability for a luminescence activity with a luciferin which is a substrate;
(c) a coding sequence consisting of a polynucleotide encoding a region consisting of the amino acid sequence of SEQ ID NO: 18; and,
(d) a coding sequence consisting of a polynucleotide encoding a region consisting of the amino acid sequence of SEQ ID NO: 18 wherein 1 or more amino acids are deleted, substituted, inserted and/or added and having a catalytic ability for a luminescence activity with a luciferin which is a substrate; and,
(2) a second coding sequence consisting of a polynucleotide encoding a polypeptide having at least one cysteine residue for binding to other useful compound via the thiol group.

[10] The polynucleotide according to [9] above, wherein the second coding sequence is selected from the group consisting of (e) to (h) below:
(e) a coding sequence consisting of a polynucleotide encoding a region consisting of the nucleotide sequence of SEQ ID NO: 19;
(f) a coding sequence consisting of a polynucleotide which hybridizes under stringent conditions to a polynucleotide complementary to a nucleotide sequence consisting of the nucleotide sequence of SEQ ID NO: 19 and encodes a region having at least one cysteine residue for binding to other useful compound via the thiol group;
(g) a coding region consisting of a polynucleotide encoding a region consisting of the amino acid sequence of SEQ ID NO: 20; and, (h) a coding region consisting of a polynucleotide encoding a region consisting of the amino acid sequence of SEQ ID NO: 20 wherein 1 or more amino acids are deleted, substituted, inserted and/or added and having at least one cysteine residue for binding to other useful compound via the thiol group.

[11] The polynucleotide according to [10] above, wherein the second coding sequence is selected from the group consisting of (e) to (h) below:

(e) a coding sequence consisting of a polynucleotide encoding a region consisting of the nucleotide sequence of SEQ ID NO: 19;

(f) a coding sequence consisting of a polynucleotide which hybridizes under high stringent conditions to a polynucleotide consisting of a nucleotide sequence complementary to the nucleotide sequence of SEQ ID NO: 19 and encodes a region having at least one cysteine residue for binding to other useful compound via the thiol group;

(g) a coding sequence consisting of a polynucleotide encoding a region consisting of the amino acid sequence of SEQ ID NO: 20; and, (h) a coding sequence consisting of a polynucleotide encoding a region consisting of the amino acid sequence of SEQ ID NO: 20 wherein 1 to 3 amino acids are deleted, substituted, inserted and/or added and having at least one cysteine residue for binding to other useful compound via the thiol group.

[12] The polynucleotide according to any one of [9] to [11] above, wherein the first coding sequence is selected from the group consisting of (a) to (d) below:

(a) a coding sequence consisting of a polynucleotide consisting of the nucleotide sequence of SEQ ID NO: 17;

(b) a coding sequence consisting of a polynucleotide which hybridizes under high stringent conditions to a polynucleotide consisting of a nucleotide sequence complementary to the nucleotide sequence of SEQ ID NO: 17 and encodes a region having a catalytic ability for a luminescence activity with a luciferin which is a substrate;

(c) a coding sequence consisting of a polynucleotide encoding a region consisting of the amino acid sequence of SEQ ID NO: 18; and, (d) a coding sequence consisting of a polynucleotide encoding a region consisting of the amino acid sequence of SEQ ID NO: 18 wherein 1 to 10 amino acids are deleted, substituted, inserted and/or added and having a catalytic ability for a luminescence activity with a luciferin which is a substrate.

[13] The polynucleotide according to [12] above, wherein:

(1) the first coding sequence is a coding sequence consisting of a polynucleotide consisting of the nucleotide sequence of SEQ ID NO: 17; and, (2) the second coding sequence is a coding sequence consisting of a polynucleotide consisting of the nucleotide sequence of SEQ ID NO: 19.

[14] A polynucleotide comprising a polynucleotide consisting of the nucleotide sequence of SEQ ID NO: 3, 5 or 7.

[15] A recombinant vector comprising the polynucleotide according to any one of [8] to [14] above.

[16] A transformant transformed with the recombinant vector according to [15] above.

[17] A method for producing the fusion protein according to any one of [1] to [7] above, which comprises culturing the transformant of [16] above and producing the fusion protein according to any one of [1] to [7] above.

[18] A complex comprising the fusion protein according to any one of [1] to [7] above and other useful compound bound to the fusion protein via the thiol group of the cysteine residue in the second region.

[19] The complex according to [18] above, wherein other useful compound is a fluorescent substance and/or a ligand specific to an analyte.

[20] A kit comprising the fusion protein according to any one of [1] to [7] above.

[21] A kit comprising the polynucleotide according to any one of [8] to [14] above, the recombinant vector according to [15] above or the transformant according to [16] above.

[22] A kit comprising the complex of [18] or [19] above.

[23] The kit according to any one of [20] to [22] above, further comprising a luciferin.

[24] The kit according to [23] above, wherein the luciferin is a coelenterazine analogue.

[25] The kit according to [24] above, wherein the coelenterazine analogue is coelenterazine.

[26] A method for performing a luminescence reaction, which comprises contacting the fusion protein according to any one of [1] to [7] above or the complex according to [18] or [19] above with a luciferin.

[27] A method for analyzing a physiological function or determining an enzyme activity, which comprises performing bioluminescence resonance energy transfer (BRET) using the fusion protein according to any one of [1] to [7] above or the complex according to [18] or [19] above as a donor protein.

[28] A method for determining a substance specific to the ligand, which comprises using the complex according to [19] above.

The fusion protein of the present invention is a luciferase which can be modified by chemical modification and is highly available for general purposes. In a preferred embodiment of the present invention, the fusion protein retains the catalytic ability of Gaussia luciferase for the luminescence activity.

BRIEF DESCRIPTION OF THE DRAWINGS

FIG. 1 A-B are a schematic view showing the expression vector pPICZα-hgLinker having a hinge sequence and a multicloning site used in the present invention.

FIG. 2 A-B are a schematic view showing the expression vector pPICZα-hgGL-H for hg-Gaussia luciferase to express in yeast, which is used in the present invention.

FIG. 4 A-B are a schematic view showing the expression vector pCold-hgA-GL for hgA-Gaussia luciferase to express in E. coli, which is used in the present invention.

BEST MODE FOR CARRYING OUT THE INVENTION

Figure 3:
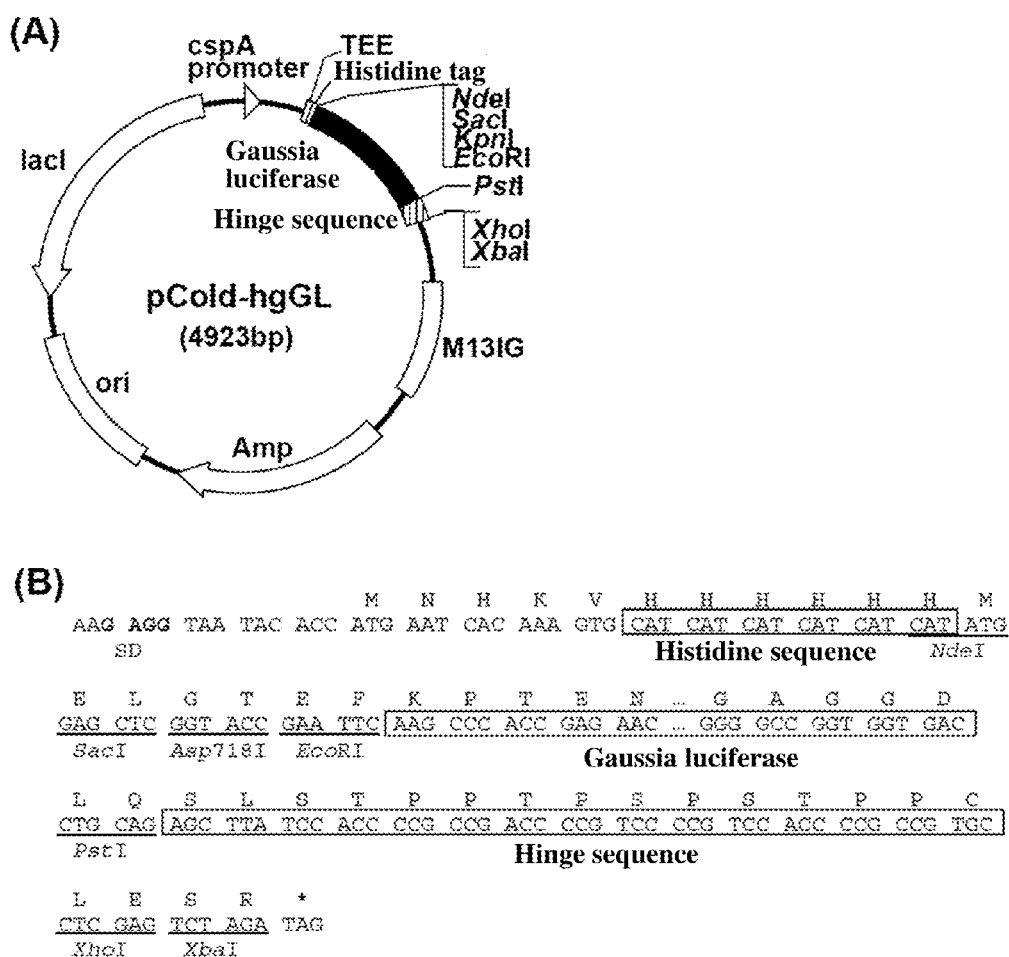
FIG. 3 A-B are a schematic view showing the expression vector pCold-hgGL for hg-Gaussia luciferase to express in E. coli, which is used in the present invention.

Hereinafter, the present invention will be described in detail.

1. Fusion Protein of the Invention

The fusion protein of the present invention is a fusion protein comprising (1) a first region selected from the group consisting of a region consisting of the amino acid sequence of SEQ ID NO: 18 and a region having substantially the same activity or function as the region consisting of the amino acid sequence of SEQ ID NO: 18, and (2) a second region consisting of an amino acid sequence for a polypeptide having at least one cysteine residue for binding to other useful compound via the thiol group.

In the fusion protein of the present invention, the first region and the second region may be arranged either in the order of "the N terminus-the first region-the second region-the C terminus" or in the order of "the N terminus-the second region-the first region-the C terminus." In the fusion protein in a preferred embodiment of the present invention, the first region and the second region are arranged in the order of "the N terminus-the first region-the second region-the C terminus."

(1) First Region

The first region is intended to mean a region consisting of the amino acid sequence of SEQ ID NO: 18 or a region having substantially the same activity or function as the region consisting of the amino acid sequence of SEQ ID NO: 18.

The term substantially the same activity or function is intended to mean a catalytic ability for a luminescence activity with a luciferin (e.g., a coelenterazine analogue) which is a substrate (hereinafter sometimes referred to as "luminescence activity"), namely, an activity of catalyzing the reaction where luciferin (e.g., coelenterazine analogue) is oxidized by oxygen molecules to form oxyluciferin in its excited state. The oxyluciferin formed in the excited state emits visible light and turns to the ground state.

The catalytic ability for the luminescence activity described above can be determined by the method described in, e.g., Inouye, S. & Sahara, Y. (2008) Biochem. Biophys. Res. Commun. 365, 96-101, etc. Specifically, the fusion protein of the present invention is mixed with a luciferin to initiate a luminescence reaction and the catalytic ability for the luminescence activity can be determined using an apparatus for measuring luminescence, e.g., Luminescencer-PSN AB2200 (manufactured by Atto), Centro 960 luminometer (manufactured by Berthold), etc.

The luciferin used in the present invention may be any luciferin as long as it serves as a substrate for the fusion protein of the present invention. Specifically, the luciferin used in the present invention includes a coelenterazine analogue.

As used herein, the coelenterazine analogue is intended to mean coelenterazine and a coelenterazine derivative. Examples of the coelenterazine derivative include h-coelenterazine, hcp-coelenterazine, cp-coelenterazine, f-coelenterazine, fcp-coelenterazine, n-coelenterazine, Bis-coelenterazine, MeO-coelenterazine, e-coelenterazine, cl-coelenterazine, ch-coelenterazine, and the like. Of these coelenterazine analogues, coelenterazine is particularly preferred in the present invention. These coelenterazine analogues may be synthesized by publicly known methods or may also be commercially available.

The coelenterazine analogues can be synthesized by the methods described in, e.g., Shimomura et al. (1988) Biochem. J. 251, 405-410, Shimomura et al. (1989) Biochem. J. 261, 913-920, Shimomura et al. (1990) Biochem. J. 270, 309-312, etc. or modifications thereof.

The coelenterazine analogues which are commercially available include, for example, coelenterazine and h-coelenterazine manufactured by Chisso Corporation; hcp-coelenterazine, cp-coelenterazine, f-coelenterazine, fcp-coelenterazine and n-coelenterazine manufactured by Sigma Inc., and the like.

Specifically, the first region is selected from the group consisting of (a) to (d) below:

(a) a region consisting of the amino acid sequence of SEQ ID NO: 18;

(b) a region consisting of the amino acid sequence of SEQ ID NO: 18 wherein 1 or more amino acids are deleted, substituted, inserted and/or added and having a catalytic ability for a luminescence activity with a luciferin which is a substrate;

(c) a region consisting of an amino acid sequence having at least 70% homology to the amino acid sequence of SEQ ID NO: 18 and having a catalytic ability for a luminescence activity with a luciferin which is a substrate; and, (d) a region consisting of an amino acid sequence encoded by a polynucleotide which hybridizes under stringent conditions to a polynucleotide consisting of a nucleotide sequence complementary to the nucleotide sequence of SEQ ID NO: 17 and having a catalytic ability for a luminescence activity with a luciferin which is a substrate.

In the first region, the "deletion, substitution, insertion and/or addition of one or more amino acid residues" means that one or a plurality of amino acid residues are deleted, substituted, inserted and/or added at an optional position(s) in the same sequence and at a position(s) in one or a plurality of amino acid sequences.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and,

Group G: phenylalanine and tyrosine.

In the first region, the range of "1 or more" in "the amino acid sequence in which 1 or more amino acids are deleted, substituted, inserted and/or added" is, for example, 1 to 20, 1 to 15, 1 to 10, 1 to 9, 1 to 8, 1 to 7, 1 to 6 (1 to several), 1 to 5, 1 to 4, 1 to 3, 1 to 2, and 1. In general, the less the number of amino acids deleted, substituted, inserted or added, the more preferable. In the deletion, substitution, insertion and addition of the amino acid residues described above, two or more may occur concurrently. Such domains can be acquired site-directed mutagenesis described in Sambrook J. et al., Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985); Proc. Natl. Acad. Sci. USA, 82, 488 (1985); etc.

In the first region, the range of "at least 70%" in the "amino acid sequence having at least 70% homology" is, for example, 70% or more, 75% or more, 80% or more, 85% or more, 88% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value of the homology described above is more preferable as the number becomes larger. The homology of nucleotide sequences or amino acid sequences can be determined using a sequencing program such as BLAST (see, e.g., Altzchul, S. F. et al., J. Mol. Biol., 215, 403 (1990), etc.) or the like. When BLAST is used, the default parameters for the respective programs are employed.

In the first region, the "polynucleotide which hybridizes under stringent conditions" is intended to mean a polynucleotide (e.g., DNA) which is obtained by, for example, colony hybridization, plaque hybridization or Southern hybridization using as a probe all or part of the polynucleotide consisting of a nucleotide sequence complementary to the nucleotide sequence of SEQ ID NO: 17 or the polynucleotide encoding the amino acid sequence of SEQ ID NO: 18. Specific examples include a polynucleotide which can be identified by performing hybridization at 65° C. in the presence of 0.7 to 1.0 mol/L NaCl using a filter on which the polynucleotide from a colony or plaque is immobilized, then washing the filter at 65° C. with an SSC (saline-sodium citrate) solution having a concentration of 0.1 to 2 times (1×SSC solution is composed of 150 mmol/L sodium chloride and 15 mmol/L sodium citrate).

Hybridization may be performed in accordance with modifications of the methods described in laboratory manuals, e.g., Sambrook, J. et al.: Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Glover D. M. and Hames B. D., DNA Cloning 1: Core Techniques, A practical Approach, Second Edition, Oxford University Press (1995); etc.

As used herein, the "stringent conditions" may be any of low stringent conditions, moderate stringent conditions or high stringent conditions. The "low-stringent conditions" are, for example, conditions of 5×SSC, 5×Denhardt's solution, 0.5% (w/v) SDS, 50% (v/v) formamide and 32° C. The "moderate stringent conditions" are, for example, conditions of 5×SSC, 5×Denhardt's solution, 0.5% (w/v) SDS, 50% (v/v) formamide and 42° C. The "high-stringent conditions" are, for example, 5×SSC, 5×Denhardt's solution, 0.5% (w/v) SDS, 50% (v/v) formamide and 50° C. The more stringent the conditions are, the higher the complementarity required for double-strand formation. Specifically, for example, under these conditions, a polynucleotide (e.g., DNA) of higher homology is expected to be obtained efficiently as the temperature becomes higher, although multiple factors are involved in hybridization stringency, including temperature, probe concentration, probe length, ionic strength, time, salt concentration, etc. One skilled in the art may achieve a similar stringency by appropriately choosing these factors.

When a commercially available kit is used for hybridization, for example, Alkphos Direct Labeling Reagents (manufactured by Amersham Pharmacia) can be used. In this case, according to the attached protocol, a membrane is incubated with a labeled probe overnight, the membrane is washed with a primary wash buffer containing 0.1% (w/v) SDS under conditions at 55° C. and then the hybridized DNA can be detected.

Other hybridizable polynucleotides include, as calculated by a sequencing program such as BLAST or the like using the default parameters, DNAs having the homology of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8%, or 99.9% or more, to the polynucleotide consisting of the nucleotide sequence of SEQ ID NO: 17 or the polynucleotide encoding the amino acid sequence of SEQ ID NO: 18. The homology of nucleotide sequences or amino acid sequences can be determined using the method described above.

In a preferred embodiment of the present invention, the first region is selected from the group consisting of (a) to (d) below:

(a) a region consisting of the amino acid sequence of SEQ ID NO: 18;

(b) a region consisting of the amino acid sequence of SEQ ID NO: 18 wherein 1 to 10 amino acids are deleted, substituted, inserted and/or added and having a catalytic ability for a luminescence activity with a luciferin which is a substrate;

(c) a region consisting of an amino acid sequence having at least 90% homology to the amino acid sequence of SEQ ID NO: 18 and having a catalytic ability for a luminescence activity with a luciferin which is a substrate; and, (d) a region consisting of an amino acid sequence encoded by a polynucleotide which hybridizes under high stringent conditions to a polynucleotide consisting of a nucleotide sequence complementary to the nucleotide sequence of SEQ ID NO: 17 and having a catalytic ability for a luminescence activity with a luciferin which is a substrate.

More preferably, the first region is a region consisting of the amino acid sequence of SEQ ID NO: 18.

(2) Second Region

The second region is a region consisting of an amino acid sequence for a polypeptide having at least one cysteine residue for binding to other useful compound via the thiol group. The term "1 or more" in the term "having at least one cysteine residue for binding to other useful compound via the thiol group" is used to mean, for example, 1, 2 or 3, preferably 1 or 2 and more preferably 1. Other useful compound can be introduced into the fusion protein of the present invention by chemical modification via the thiol group derived from cysteine residues contained in the second region. In a preferred embodiment of the present invention, other useful compound can be introduced into the fusion protein of the present invention by chemical modification via the thiol group derived from cysteine residues contained in the second region, without any significant loss of the catalytic ability for the luminescence activity in the first region.

In the second region, the polypeptide has a length of, e.g., 2 to 40 amino acids, preferably 5 to 35 amino acids, more preferably 7 to 30 amino acids, much more preferably 10 to 20 amino acids and most preferably 15 amino acids.

Other useful compounds for binding to the second region include fluorescent substances, ligands specific to analytes (e.g., biotin, biotin-conjugated proteins, enzymes, substrates, antibodies, antigens, nucleic acids, polysaccharides, receptors or compounds capable of binding thereto, etc.), and the like.

The "fluorescent substances" and "ligands" are those described below.

In some embodiments of the present invention, the second region is selected from the group consisting of (e) to (h) below:

(e) a region consisting of the amino acid sequence of SEQ ID NO: 20;

(f) a region comprising the amino acid sequence of SEQ ID NO: 20 wherein 1 or more amino acids are deleted, substituted, inserted and/or added and having at least one cysteine residue for binding to other useful compound via the thiol group;

(g) a region comprising an amino acid sequence having at least 70% homology to the amino acid sequence of SEQ ID NO: 20 and having at least one cysteine residue for binding to other useful compound via the thiol group; and, (h) a region comprising an amino acid sequence encoded by a polynucleotide which hybridizes under stringent conditions to a polynucleotide consisting of a nucleotide sequence complementary to the nucleotide sequence of SEQ ID NO: 19 and having at least one cysteine residue for binding to other useful compound via the thiol group.

In the second region, "the deletion, substitution, insertion and/or addition of one or more amino acid residues" means that one or a plurality of amino acid residues are deleted, substituted, inserted and/or added at an optional position(s) in the same sequence and at a position(s) in one or a plurality of amino acid sequences.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and,

Group G: phenylalanine and tyrosine.

In the second region, the range of "1 or more" in "the amino acid sequence in which 1 or more amino acids are deleted, substituted, inserted and/or added" is, for example, 1 to 5, 1 to 4, 1 to 3, 1 to 2, and 1. In general, the less the number of amino acids deleted, substituted, inserted or added, the more preferable. In the deletion, substitution, insertion and addition of the amino acid residues described above, two or more may occur concurrently. Such domains can be acquired site-directed mutagenesis described in Sambrook J. et al., Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985); Proc. Natl. Acad. Sci. USA, 82, 488 (1985); etc.

In the second region, the range of "at least 70%" in the "amino acid sequence having at least 70% homology" is, for example, 70% or more, 75% or more, 80% or more, 85% or more, 88% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value of the homology described above is more preferable as the number becomes larger. The homology of nucleotide sequences or amino acid sequences can be determined using a sequencing program such as BLAST (see, e.g., Altzchul, S. F. et al., J. Mol. Biol., 215, 403 (1990), etc.) or the like. When BLAST is used, the default parameters for the respective programs are employed.

In the second region, the "polynucleotide which hybridizes under stringent conditions" is intended to mean a polynucleotide (e.g., DNA) which is obtained by, for example, colony hybridization, plaque hybridization or Southern hybridization using as a probe all or part of the polynucleotide consisting of a nucleotide sequence complementary to the nucleotide sequence of SEQ ID NO: 19 or the polynucleotide encoding the amino acid sequence of SEQ ID NO: 20. Specific examples include a polynucleotide which can be identified by performing hybridization at 65° C. in the presence of 0.7 to 1.0 mol/L NaCl using a filter on which the polynucleotide from a colony or plaque is immobilized, then washing the filter at 65° C. with an SSC (saline-sodium citrate) solution having a concentration of 0.1 to 2 times (1×SSC solution is composed of 150 mmol/L sodium chloride and 15 mmol/L sodium citrate).

Hybridization may be performed in accordance with modifications of the methods described in laboratory manuals, e.g., Sambrook, J. et al.: Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Glover D. M. and Hames B. D., DNA Cloning 1: Core Techniques, A practical Approach, Second Edition, Oxford University Press (1995); etc.

As used herein, the "stringent conditions" may be any of low stringent conditions, moderate stringent conditions or high stringent conditions. The "low-stringent conditions" are, for example, conditions of 5×SSC, 5×Denhardt's solution, 0.5% (w/v) SDS, 50% (v/v) formamide and 32° C. The "moderate stringent conditions" are, for example, conditions of 5×SSC, 5×Denhardt's solution, 0.5% (w/v) SDS, 50% (v/v) formamide and 42° C. The "high-stringent conditions" are, for example, 5×SSC, 5×Denhardt's solution, 0.5% (w/v) SDS, 50% (v/v) formamide and 50° C. The more stringent the conditions are, the higher the complementarity required for double-strand formation. Specifically, for example, under these conditions, a polynucleotide (e.g., DNA) of higher homology is expected to be obtained efficiently as the temperature becomes higher, although multiple factors are involved in hybridization stringency, including temperature, probe concentration, probe length, ionic strength, time, salt concentration, etc. One skilled in the art may achieve a similar stringency by appropriately choosing these factors.

When a commercially available kit is used for hybridization, for example, Alkphos Direct Labeling Reagents (manufactured by Amersham Pharmacia) can be used. In this case, according to the attached protocol, a membrane is incubated with a labeled probe overnight, the membrane is washed with a primary wash buffer containing 0.1% (w/v) SDS under conditions at 55° C. and then the hybridized DNA can be detected.

Other hybridizable polynucleotides include, as calculated by a sequencing program such as BLAST or the like using the default parameters, DNAs having the homology of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8%, or 99.9% or more, to the polynucleotide consisting of the nucleotide sequence of SEQ ID NO: 19 or the polynucleotide encoding the amino acid sequence of SEQ ID NO: 20. The homology of nucleotide sequences or amino acid sequences can be determined using the method described above.

In a preferred embodiment of the present invention, the second region is selected from the group consisting of (e) to (h) below:

(e) a region consisting of the amino acid sequence of SEQ ID NO: 20;

(f) a region comprising the amino acid sequence of SEQ ID NO: 20 wherein 1 to 3 amino acids are deleted, substituted, inserted and/or added and having at least one cysteine residue for binding to other useful compound via the thiol group;

(g) a region comprising an amino acid sequence having at least 90% homology to the amino acid sequence of SEQ ID NO: 20 and having at least one cysteine residue for binding to other useful compound via the thiol group; and, (h) a region comprising an amino acid sequence encoded by a polynucleotide which hybridizes under high stringent conditions to a polynucleotide consisting of a nucleotide sequence complementary to the nucleotide sequence of SEQ ID NO: 19 and having at least one cysteine residue for binding to other useful compound via the thiol group.

In a more preferred embodiment of the present invention, the second region is a region consisting of the amino acid sequence of SEQ ID NO: 20.

In a preferred embodiment of the present invention, the fusion protein is a fusion protein comprising:

(1) a first region consisting of the amino acid sequence of SEQ ID NO: 18 and (2) a second region consisting of the amino acid sequence of SEQ ID NO: 20.

In a more preferred embodiment of the present invention, the fusion protein includes, for example, a fusion protein consisting of the amino acid sequence of SEQ ID NO: 4, 6 or 8.

The fusion protein of the present invention may further contain an additional peptide sequence at the N terminus and/or C terminus, preferably at the N terminus, as in the amino acid sequences of SEQ ID NOS: 4, 6 and 8. The additional peptide sequence includes, for example, at least one peptide sequence selected from the group consisting of a peptide sequence for promoting translation, a peptide sequence for purification, a secretory signal peptide sequence, a peptide sequence for expressing the fusion protein of the present invention as a soluble protein, an epitope sequence capable of recognizing an antibody, etc. The additional peptide sequence is preferably a peptide sequence for purification and/or a secretory signal peptide sequence. In a still more preferred embodiment of the present invention, the additional peptide sequence is at least one sequence selected from the group consisting of a peptide sequence for purification, a secretory signal peptide sequence and a peptide sequence for expressing the fusion protein of the present invention as a soluble protein.

The fusion protein of the present invention may further contain a linker sequence for restriction enzyme sites, as in the amino acid sequences of SEQ ID NOS: 4, 6 and 8.

Peptide sequences used in the art can be employed as the peptide sequence for promoting translation. Examples of the peptide sequence for promoting translation are a TEE sequence, and the like.

Peptide sequences employed in the art can be used as the peptide sequence for purification. The peptide sequence for purification includes, for example, a histidine tag sequence having a consecutive amino acid sequence of at least 4 and preferably at least 6 histidine residues, an amino acid sequence with a binding domain of glutathione S-transferase into glutathione, the amino acid sequence of Protein A, an avidin tag sequence, etc.

The secretory signal peptide is intended to mean a peptide region which has the role of transporting a polypeptide bound to the secretory signal peptide across a cell membrane. Amino acid sequences of such secretory signal peptides and nucleotide sequences encoding the same are well known in the art and reported (see, e.g., von Heijine, G., Biochim. Biophys. Acta, 947: 307-333 (1988); von Heijine, G., J. Membr. Biol., 115, 195-201 (1990); etc.). Specific examples of secretory signal peptides include the secretory signal peptide from the outer membrane protein A of *E. coli* (OmpA) (Ghrayeb, J. et al., (1984) EMBO J. 3:2437-2442), the secretory signal peptide from cholera toxin obtained from *Vibrio cholerae*, etc.

The peptide used to express the fusion protein of the present invention as a soluble protein includes, for example, polypeptides represented by formula $(Z)_n$. The amino acid sequences for the polypeptides represented by formula $(Z)_n$ and the nucleic acid sequences encoding the same are described in, e.g., JPA KOKAI No. 2008-99669.

As the linker sequences for restriction enzyme sites, peptide sequences used in the art can be employed.

In the fusion protein of the present invention in which the first region and the second region are arranged in the order of "the N terminus-the first region-the second region-the C terminus," the length of the portion between the first region and the C terminus except for the first region is, for example, 4 to 50 amino acids, preferably 7 to 45 amino acids, more preferably 14 to 43 amino acids, much more preferably 17 to 40 amino acids and most preferably 21 to 36 amino acids.

In the fusion protein of the present invention in which the first region and the second region are arranged in the order of "the N terminus-the second region-the first region-the C terminus," the length of the portion between the first region and the N terminus except for the first region is, for example, 4 to 50 amino acids, preferably 7 to 45 amino acids, more preferably 14 to 43 amino acids, much more preferably 17 to 40 amino acids and most preferably 21 to 36 amino acids.

The method for acquiring the fusion protein of the invention is not particularly limited. The fusion protein of the invention may be a fusion protein synthesized by chemical synthesis, or a recombinant protein produced by a genetic engineering technique. If the fusion protein of the invention is to be chemically synthesized, synthesis may be carried out by, for example, the Fmoc (fluorenylmethyloxycarbonyl) method or the tBoc (t-butyloxycarbonyl) method. In addition, peptide synthesizers available from, for example, Advanced ChemTech, PerkinElmer, Pharmacia, Protein Technology Instrument, Synthecell-Vega, PerSeptive, Shimadzu Corporation, etc. may also be used for chemical synthesis. If the fusion protein of the invention is to be produced by a genetic engineering technique, the fusion protein may be produced by a conventional genetic recombination technique. More specifically, the fusion protein of the invention may be produced by inserting a polynucleotide (e.g., DNA) encoding the fusion protein of the invention into a suitable expression system. The polynucleotide encoding the fusion protein of the invention and expression of the fusion protein of the invention in an expression system will be later described.

2. Polynucleotide of the Invention

The present invention also provides a polynucleotide encoding the fusion protein of the invention described above. The polynucleotide of the invention may be any polynucleotide as long as it has a nucleotide sequence encoding the fusion protein of the invention, although a DNA is preferred. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a reverse transcription polymerase chain reaction (hereinafter abbreviated as RT-PCR) using the total RNA or mRNA fraction prepared from the cell or tissue described above.

Specifically, the polynucleotide of the present invention includes a polynucleotide comprising:

(1) a first coding sequence selected from the group consisting of (a) to (d) below:

(a) a coding sequence consisting of a polynucleotide consisting of the nucleotide sequence of SEQ ID NO: 17;

(b) a coding sequence consisting of a polynucleotide which hybridizes under stringent conditions to a polynucleotide consisting of a nucleotide sequence complementary to the nucleotide sequence of SEQ ID NO: 17 and encodes a region having a catalytic ability for a luminescence activity with a luciferin which is a substrate;

(c) a coding sequence consisting of a polynucleotide encoding a region consisting of the amino acid sequence of SEQ ID NO: 18; and, (d) a coding sequence consisting of a polynucleotide encoding a region consisting of the amino acid sequence of SEQ ID NO: 18 wherein 1 or more amino acids are deleted, substituted, inserted and/or added and having a catalytic ability for a luminescence activity with a luciferin which is a substrate; and, (2) a second coding sequence consisting of a polynucleotide encoding a polypeptide having at least one cysteine residue for binding to other useful compound via the thiol group.

Preferably, the second coding sequence described above is selected from the group consisting of (e) to (h) below:

(e) a coding sequence consisting of a polynucleotide encoding a region consisting of the nucleotide sequence of SEQ ID NO: 19;

(f) a coding sequence consisting of a polynucleotide which hybridizes under stringent conditions to a polynucleotide complementary to a nucleotide sequence consisting of the nucleotide sequence of SEQ ID NO: 19 and encodes a region having at least one cysteine residue for binding to other useful compound via the thiol group;

(g) a coding region consisting of a polynucleotide encoding a region consisting of the amino acid sequence of SEQ ID NO: 20; and, (h) a coding region consisting of a polynucleotide encoding a region consisting of the amino acid sequence of SEQ ID NO: 20 wherein 1 or more amino acids are deleted, substituted, inserted and/or added and having at least one cysteine residue for binding to other useful compound via the thiol group.

As used herein, the "polynucleotide which hybridizes under stringent conditions" in the first and second coding sequences refers to a polynucleotide (e.g., DNA) which is obtained by, for example, colony hybridization, plaque hybridization or Southern hybridization using as a probe all or part of the polynucleotide consisting of a nucleotide sequence complementary to the nucleotide sequence of SEQ ID NO: 17 or 19 or the polynucleotide encoding the amino acid sequence of SEQ ID NO: 18 or 20. Specific examples are polynucleotides which can be identified by performing hybridization at 65° C. in the presence of 0.7 to 1.0 mol/L NaCl using a filter on which a polynucleotide derived from a colony or plaque is immobilized, then washing the filter at 65° C. with an SSC (saline-sodium citrate) solution having a concentration in a range of 0.1 to 2 times (a 1-fold SSC solution is composed of 150 mmol/L of sodium chloride and 15 mmol/L of sodium citrate).

Hybridization can be carried out based on the methods described in laboratory manuals such as Sambrook J. et al., Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Glover D. M. and Hames B. D., DNA Cloning 1: Core Techniques, A Practical Approach, Second Edition, Oxford University Press (1995); etc.

As used herein, the "stringent conditions" may be any of low stringent conditions, moderate stringent conditions or high stringent conditions. The "low-stringent conditions" are, for example, conditions of 5×SSC, 5×Denhardt's solution, 0.5% (w/v) SDS, 50% (v/v) formamide and 32° C. The "moderate stringent conditions" are, for example, conditions of 5×SSC, 5×Denhardt's solution, 0.5% (w/v) SDS, 50% (v/v) formamide and 42° C. The "high-stringent conditions" are, for example, 5×SSC, 5×Denhardt's solution, 0.5% (w/v) SDS, 50% (v/v) formamide and 50° C. The more stringent the conditions are, the higher the complementarity required for double-strand formation. Specifically, for example, under these conditions, a polynucleotide (e.g., DNA) of higher homology is expected to be obtained efficiently as the temperature becomes higher, although multiple factors are involved in hybridization stringency, including temperature, probe concentration, probe length, ionic strength, time, salt concentration, etc. One skilled in the art may achieve a similar stringency by appropriately choosing these factors.

When a commercially available kit is used for hybridization, for example, Alkphos Direct Labeling Reagents (manufactured by Amersham Pharmacia) can be used. In this case, according to the attached protocol, a membrane is incubated with a labeled probe overnight, the membrane is washed with a primary wash buffer containing 0.1% (w/v) SDS under conditions at 55° C. and then the hybridized DNA can be detected.

Other hybridizable polynucleotides include, as calculated by a sequencing program such as BLAST or the like using the default parameters, DNAs having the homology of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8%, or 99.9% or more, to the polynucleotide consisting of the nucleotide sequence of SEQ ID NO: 17 or 19, or the polynucleotide encoding the amino acid sequence of SEQ ID NO: 18 or 20. The homology of nucleotide sequences or amino acid sequences can be determined using the method described above.

In the first and second coding sequences, "the amino acid sequence in which 1 or more amino acids are deleted, substituted, inserted and/or added" is the same as explained for the first and second regions, respectively.

A polynucleotide encoding a region having a given amino acid sequence, in which one or more amino acids are deleted, substituted, inserted and/or added, can be obtained by using a site-specific mutagenesis technique (see, e.g., Gotoh, T. et al., Gene 152, 271-275 (1995); Zoller, M. J., and Smith, M., Methods Enzymol. 100, 468-500 (1983); Kramer, W. et al., Nucleic Acids Res. 12, 9441-9456 (1984); Kramer W, and Fritz H. J., Methods. Enzymol. 154, 350-367 (1987); Kunkel, T. A., Proc. Natl. Acad. Sci. USA. 82, 488-492 (1985); Kunkel, Methods Enzymol. 85, 2763-2766 (1988); etc.), the methods utilizing amber mutation (see, e.g., the gapped duplex method, Nucleic Acids Res., 12, 9441-9456 (1984), etc.), etc.

Alternatively, a mutation can be introduced into the polynucleotide by means of a polymerase chain reaction (PCR) using a set of primers bearing on the respective 5' ends a sequence in which the target mutation (deletion, addition, substitution and/or insertion) has been introduced (see, e.g., Ho, S. N. et al., Gene, 77, 51 (1989), etc.).

Also, a polynucleotide encoding a partial protein fragment, which is one type of deletion mutant, can be obtained using as the primers an oligonucleotide having a sequence which matches the nucleotide sequence at the 5' end of the region encoding the partial fragment to be produced in the polynucleotide encoding the target protein and an oligonucleotide having a sequence complementary to the nucleotide sequence at the 3' end thereof, and performing PCR in which the polynucleotide encoding the target protein serves as a template.

In the polynucleotide in a preferred embodiment of the present invention, the first coding sequence is selected from the group consisting of (a) to (d) below:

(a) a coding sequence consisting of a polynucleotide consisting of the nucleotide sequence of SEQ ID NO: 17;

(b) a coding sequence consisting of a polynucleotide which hybridizes under high stringent conditions to a polynucleotide consisting of a nucleotide sequence complementary to the nucleotide sequence of SEQ ID NO: 17 and encodes a region having a catalytic ability for a luminescence activity with a luciferin which is a substrate;

(c) a coding sequence consisting of a polynucleotide encoding a region consisting of the amino acid sequence of SEQ ID NO: 18; and, (d) a coding sequence consisting of a polynucleotide encoding a region consisting of the amino acid sequence of SEQ ID NO: 18 wherein 1 to 10 amino acids are deleted, substituted, inserted and/or added and having a catalytic ability for a luminescence activity with a luciferin which is a substrate.

In the polynucleotide in a preferred embodiment of the present invention, the second coding sequence is selected from the group consisting of (e) to (h) below:

(e) a coding sequence consisting of a polynucleotide encoding a region consisting of the nucleotide sequence of SEQ ID NO: 19;

(f) a coding sequence consisting of a polynucleotide which hybridizes under high stringent conditions to a polynucleotide consisting of a nucleotide sequence complementary to the nucleotide sequence of SEQ ID NO: 19 and encodes a region having at least one cysteine residue for binding to other useful compound via the thiol group;

(g) a coding sequence consisting of a polynucleotide encoding a region consisting of the amino acid sequence of SEQ ID NO: 20; and, (h) a coding sequence consisting of a polynucleotide encoding a region consisting of the amino acid sequence of SEQ ID NO: 20 wherein 1 to 3 amino acids are deleted, substituted, inserted and/or added and having at least one cysteine residue for binding to other useful compound via the thiol group.

In a more preferred embodiment of the present invention, the polynucleotide is a polynucleotide comprising (1) the first coding sequence consisting of a polynucleotide consisting of the nucleotide sequence of SEQ ID NO: 17; and, (2) the second coding sequence consisting of a polynucleotide consisting of the nucleotide sequence of SEQ ID NO: 19.

The polynucleotide in a particularly preferred embodiment of the present invention includes, for example, a polynucleotide comprising a polynucleotide encoding the fusion protein consisting of the amino acid sequence of SEQ ID NO: 4, 6 or 8, and the like. The polynucleotide comprising a polynucleotide encoding the fusion protein consisting of the amino acid sequence of SEQ ID NO: 4 includes, for example, a polynucleotide comprising a polynucleotide consisting of the nucleotide sequence of SEQ ID NO: 3, etc. The polynucleotide comprising a polynucleotide encoding the fusion protein consisting of the amino acid sequence of SEQ ID NO: 6 includes, for example, a polynucleotide comprising a polynucleotide consisting of the nucleotide sequence of SEQ ID NO: 5, etc. The polynucleotide comprising a polynucleotide encoding the fusion protein consisting of the amino acid sequence of SEQ ID NO: 8 includes, for example, a polynucleotide comprising a polynucleotide consisting of the nucleotide sequence of SEQ ID NO: 7, etc.

The polynucleotide of the present invention may further contain a polynucleotide comprising a polynucleotide encoding an additional peptide sequence, as in the polynucleotide comprising the polynucleotide consisting of the nucleotide sequence of SEQ ID NO: 3, 5 or 7. The additional peptide sequence includes, for example, at least one peptide sequence selected from the group consisting of a peptide sequence for promoting translation, a peptide sequence for purification, a secretory signal peptide sequence, a peptide sequence for expressing the fusion protein of the present invention as a soluble protein, an epitope sequence capable of recognizing an antibody, etc.

The polynucleotide of the present invention may further contain a linker sequence for a restriction enzyme site, as in the polynucleotide comprising a polynucleotide consisting of the nucleotide sequence of SEQ ID NO: 3, 5 or 7.

A polynucleotide comprising a polynucleotide encoding the peptide sequence for promoting translation employed in the art can be used as the polynucleotide comprising a polynucleotide encoding the peptide sequence for promoting translation. Examples of the peptide sequence for promoting translation include those described above.

Polynucleotides comprising nucleotide sequences encoding the peptide sequence for purification employed in the art can be used as the polynucleotide encoding the peptide sequence for purification. Examples of the peptide sequence for purification include those as described above.

Polynucleotides comprising nucleic acids encoding secretory signal peptides known in the art can be used as the secretory signal peptide-encoding polynucleotide. Examples of the secretory signal peptide are those as described above.

The polynucleotide encoding the peptide sequence used to express the fusion protein of the present invention as a soluble protein includes, for example, polypeptides represented by formula $(Z)_n$. The amino acid sequences for the polypeptides represented by formula $(Z)_n$ and the nucleic acid sequences encoding the same are those as described above.

The linker sequences for restriction enzyme sites employed in the art can be used as the linker sequences for restriction enzyme sites.

3. Recombinant Vector and Transformant of the Invention

The present invention further provides recombinant vectors and transformants comprising the polynucleotides of the present invention described above.

Preparation of Recombinant Vector

The recombinant vector of the invention can be obtained by ligating (inserting) the polynucleotide (DNA) of the invention to (into) an appropriate vector. Specifically, the recombinant vector can be obtained by digesting the purified polynucleotide (DNA) with a suitable restriction enzyme, then inserting into a suitable vector at the restriction enzyme site or multicloning site, and ligating to the vector. The vector for inserting the polynucleotide of the invention is not particularly limited as long as it is replicable in a host. Vectors which may be used for this purpose include plasmids, bacteriophages, animal viruses, etc. Examples of plasmids include plasmids from *E. coli* (e.g., pBR322, pBR325, pUC118, pUC119, etc.), plasmids from *Bacillus subtilis* (e.g., pUB110, pTP5, etc.), plasmids from yeast (e.g., YEp13, YEp24, YCp50, etc.), and so on. Examples of bacteriophages include λ phage, etc. Examples of animal viruses include retroviruses, vaccinia viruses, insect viruses (e.g., baculoviruses), etc. In addition, the pCold I vector, pCold II vector, pCold III vector and pCold IV vector (all are manufactured by Takara-Bio), the PICZ α vector (manufactured by Invitrogen) and the like can also be suitably used.

The polynucleotide of the present invention is generally ligated in an expressible manner downstream from a promoter in a suitable vector. When the host used for transformation is an animal cell, the promoter is preferably an SV40-derived promoter, retrovirus promoter, metallothionein promoter, heat shock promoter, cytomegalovirus promoter, SRα promoter, and so on. When the host is a bacterium of the genus *Escherichia*, Trp promoter, T7 promoter, lac promoter, recA promoter, λPL promoter, lpp promoter, etc. are preferred. When the host is a bacterium of the genus *Bacillus*, SPO1 promoter, SPO2 promoter, penP promoter, etc. are preferred. When the host is yeast, PHO5 promoter, PGK promoter, GAP promoter, ADH1 promoter, GAL promoter, etc. are preferred. When the host is an insect cell, polyhedrin promoter, P10 promoter, etc. are preferred.

A low-temperature expression-inducible promoter may also be suitably used. Examples of the low-temperature expression-inducible promoter include promoter sequences for cold shock genes, and the like. The cold shock gene includes, for example, *Escherichia coli* cold shock genes (e.g., cspA, cspB, cspG, cspI, csdA, etc.), *Bacillus caldolyticus* cold shock genes (e.g., Bc-Csp, etc.), *Salmonella enterica* cold shock genes (e.g., cspE, etc.), *Erwinia carotovora* cold shock genes (e.g., cspG, etc.), and the like. Among others, cspA promoter, cspB promoter, cspG promoter, cspI promoter, csdA promoter and the like can be suitably used as the low-temperature expression-inducible promoter.

In addition to the foregoing, the recombinant vector of the invention may further contain, if desired, an enhancer, a splicing signal, a polyA addition signal, a ribosome binding sequence (SD sequence), a selection marker, etc., and can be provided for use. The selection marker includes, for example, a dihydrofolate reductase gene, an ampicillin resistance gene, a neomycin resistance gene, etc.

Preparation of Transformant

The thus obtained recombinant vector comprising the polynucleotide of the invention (i.e., the polynucleotide encoding the fusion protein of the invention) is introduced into an appropriate host, and the transformant can be prepared. The host is not particularly limited as long as it is capable of expressing the polynucleotide (DNA) of the invention. For example, the host may be bacteria of the genera *Escherichia*, *Bacillus*, *Pseudomonas* and *Rhizobium*, yeast, animal cells or insect cells, etc. Bacteria of the genus *Escherichia* include *Escherichia coli*, etc. Bacteria of the genus *Bacillus* include *Bacillus subtilis*, etc. Bacteria of the genus *Pseudomonas* include, for example, *Pseudomonas putida*, etc. Bacteria of the genus *Rhizobium* include, for example, *Rhizobium meliloti*, etc. Yeast includes, for example, *Saccharomyces cerevisiae*, *Schizosaccharomyces pombe*, etc. Animal cells include, for example, COS cells, CHO cells, etc. Insect cells include, for example, Sf9, Sf21, etc.

The method of transfecting the recombinant vector into the host and the method of transformation thereby can be performed according to various general methods. The method for transfecting the recombinant vector into the host cell includes, for example, the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes, for example, the method described in Molecular & General Genetics, 168, 111 (1979), etc. The method for transforming yeast includes, for example, the method described in Proc. Natl. Acad. Sci. USA, 75, 1929 (1978), etc. The method for transformation of animal cells includes, for example, the method described in Virology, 52, 456 (1973), etc. The method for transformation of insect cells includes, for example, the method described in Bio/Technology, 6, 47-55 (1988), etc. Thus, the transformant transformed with the recombinant vector comprising the polynucleotide encoding the protein of the invention (i.e., the polynucleotide of the invention) can be obtained.

Expression Vector and Transformant Comprising Low-Temperature Expression-Inducible Promoter Sequence Among others, the expression vector comprising the low-temperature expression-inducible promoter sequence is preferred as the expression vector.

Specifically, the expression vector comprising the low-temperature expression-inducible promoter sequence is intended to mean an expression vector comprising the following promoter sequence and coding sequence:

(1) a low-temperature expression-inducible promoter sequence; and, (2) a coding sequence comprising the polynucleotide of the invention.

The low-temperature expression-inducible promoter sequence is intended to mean a promoter sequence which is capable of inducing expression of the fusion protein by lowering the temperature from the culture conditions under which host cells can grow. Examples of the low-temperature expression-inducible promoter are promoters for genes which encode cold shock proteins (cold shock genes). Examples of the cold shock gene promoters include those as described above.

The temperature at which the low-temperature expression-inducible promoter used in the invention is expression-inducible is generally 30° C. or less, preferably 25° C. or less, more preferably 20° C. or less, and most preferably 15° C. or less. In order to induce the expression more efficiently, however, the expression induction is generally performed at 5° C. or more, preferably at 10° C. or more, and most preferably at approximately 15° C.

In preparing the expression vector of the invention comprising the low-temperature expression-inducible promoter sequence, the pCold I vector, pCold II vector, pCold III vector, and pCold IV vector (all manufactured by Takara-Bio) can be suitably used as the vector for insertion of the polynucleotide of the invention. The fusion protein of the invention can be produced as a soluble protein in the cytoplasm serving as a host when expression is performed in a prokaryotic host cell using these vectors.

Prokaryotic cells are preferred for the host into which the expression vector comprising the low-temperature expression-inducible promoter sequence is introduced, *Escherichia coli* being more preferred, the BL21 and JM109 strains being particularly preferred. Among others, the BL21 strain is most preferred.

Temperatures for incubation at which cell growth is achieved for the transformant wherein the expression vector comprising the low-temperature expression-inducible promoter sequence is introduced are generally 25 to 40° C. and preferably 30 to 37° C. Temperatures for the expression induction are generally 4 to 25° C., preferably 10 to 20° C., more preferably 12 to 18° C., and most preferably 15° C.

4. Production of Fusion Protein of the Invention

The present invention further provides a method for producing the fusion protein of the invention, which comprises the steps of culturing the transformant described above and producing the fusion protein of the invention. The fusion protein of the invention can be produced, for example, by culturing the transformant described above under conditions where the polynucleotide (DNA) encoding the fusion protein of the invention can be expressed, producing/accumulating the fusion protein of the invention and then separating/purifying the protein.

Incubation of Transformant

The transformant of the invention can be incubated in a conventional manner used for incubation of a host. By the incubation, the fusion protein of the invention is produced by the transformant and accumulated within the transformant or in the culture medium.

The medium for culturing the transformant using bacteria of the genus *Escherichia* or the genus *Bacillus* as a host may be any of a natural medium and a synthetic medium as far as it is a medium which contains carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed by the expression vector using an inducible promoter as the promoter is cultured, an inducer may also be added to the medium, if necessary. For example, when the transformant transformed by an expression vector using a Lac promoter is cultured, isopropyl-β-D-thiogalactopyranoside (IPTG), etc. may be added to the medium and indoleacrylic acid (IAA), etc. may be added to the medium when the transformant transformed by an expression vector using a trp promoter is cultured.

When the host is bacteria of the genus *Escherichia*, incubation is performed generally at approximately 15 to 43° C. for approximately 3 to 24 hours. If necessary, aeration and agitation may be applied. When the host is bacteria of the genus *Bacillus*, incubation is performed generally at approximately 30 to 40° C. for approximately 6 to 24 hours. If necessary, aeration and agitation may be applied.

Media for incubation of the transformant when the host is yeast include Burkholder's minimal medium (Proc. Natl. Acad. Sci. USA, 77, 4505 (1980)) and an SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20 to 35° C. for approximately 24 to 72 hours. If necessary, aeration and agitation may be applied.

Media for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30 to 40° C. for approximately 15 to 60 hours. If necessary, aeration and agitation may be applied.

Media for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 hours. If necessary, aeration and agitation may be applied.

Temperatures for incubation at which the transformant transformed by the expression vector comprising the low-temperature expression-inducible promoter sequence and temperatures for expression induction are as described above.

Separation/Purification of Fusion Protein of the Invention

The fusion protein of the present invention can be obtained by separating/purifying the fusion protein of the present invention from the culture described above. As used herein, the culture is intended to mean any one of a culture broth, cultured cells or cultured bacteria and a cell lysate of the cultured cells or cultured bacteria. The fusion protein of the present invention can be separated/purified in a conventional manner.

Specifically, when the fusion protein of the present invention accumulates in the cultured bacteria or cultured cells, after completion of the incubation, the bacteria or cells are disrupted in a conventional manner (e.g., ultrasonication, lysozyme, freezing and thawing, etc,) and then a crude extract of the fusion protein of the invention can be obtained in a conventional manner (e.g., centrifugation, filtration, etc.). When the fusion protein of the invention accumulates in the periplasmic space, after completion of the incubation, the extract containing the fusion protein of the invention can be obtained in a conventional manner (e.g., the osmotic shock method, etc.). When the fusion protein of the invention accumulates in the culture broth, after completion of the incubation, the culture supernatant containing the fusion protein of the invention can be obtained by separating the bacteria or cells and the culture supernatant in a conventional manner (e.g., centrifugation, filtration, etc.).

The fusion protein of the invention contained in the extract or culture supernatant thus obtained can be purified by conventional methods of separation and purification. Examples of these separation and purification methods which may be used include ammonium sulfate precipitation, gel filtration chromatography, ion-exchange chromatography, affinity chromatography, reversed-phase high-performance liquid chromatography, dialysis, ultrafiltration, etc., alone or in a suitable combination thereof. If the fusion protein of the invention contains the peptide sequence for purification described above, it is preferred to perform the purification using the same. Specifically, when the fusion protein of the invention contains a histidine tag sequence, nickel chelate affinity chromatography may be used; when the fusion protein of the invention contains the binding domain of S-transferase to glutathione, affinity chromatography with a glutathione-binding gel may be used; when the fusion protein of the invention contains the amino acid sequence of Protein A, antibody affinity chromatography may be used.

5. Complex of the Invention

The fusion protein of the invention (hereinafter sometimes referred to as "the luciferase of the invention") can bind to other useful compound (e.g., a fluorescent substance, a ligand specific to an analyte to be detected, etc.) to form a complex.

The complex of the present invention comprises the luciferase of the invention and other useful compound bound to the second region of the luciferase via the thiol group of the cysteine residues. In some embodiments of the present invention, the complex comprises the luciferase of the invention bound to a fluorescent substance or a ligand specific to an analyte. In the complex in some embodiments of the present invention, the binding ratio of the thiol group of the luciferase to the fluorescent substance or ligand is 1:1 or a ratio close thereto.

Among the other useful compounds, the fluorescent substance includes an organic compound such as Hoechist3342, Indo-1, DAP1, etc.; a fluorescent protein such as a green fluorescent protein (GFP), a blue fluorescent protein (BFP), a mutant GFP fluorescent protein, phycobilin, etc.

The ligand specific to an analyte may be any one of a substance directly binding to the analyte and a substance indirectly binding to the analyte. The ligand includes, for example, biotin, biotin-conjugated proteins, enzymes, substrates, antibodies, antigens, nucleic acids, polysaccharides, receptors and compounds capable of binding to these substances.

Among them, the biotin-conjugated proteins include avidin, streptavidin, mutant avidin (NeutrAvidin), etc. These biotin-conjugated proteins may also be obtained from commercially available ones. Also, the biotin-conjugated proteins which are commercially available may be prepared so as to be modifiable.

Antigens against a variety of substances (e.g., trace components of human, animal or plant origin in vivo such as tumor markers, hormones, etc., environmental trace pollutants, etc.) and antibodies against these antigens have been commercially marketed so far. Antibodies that an analyte to be determined is an antigen can be obtained appropriately depending upon necessity and provided for use.

As markers which increase in blood serum or urine accompanied by tumor growth, inter alia, there are known so far markers which specifically increase in each organ accompanied by tumor formation, such as fetal antigen, CA19-9, sialyl Lex-i antigen, sialyl Tn antigen, thymidine kinase activity, tissue polypeptide antigen, basic fetoprotein, immunosuppressive acidic protein, CA72-4, CA125, DUPAN-2, SPan-1, elastase 1, BCA-225, CA15-3, SCC antigen, cytokeratin 19 fragment, prostate specific antigen, γ-seminoprotein, prostate acidic phosphatase, α-fetoprotein, AFP lectin fraction, PIVKA-II, neuron specific enolase, NCC-ST-439, CA130, type I collagen-C-telopeptide, and the like. These antigens are commercially available and may be suitably used as the standard substance in monitoring these markers in blood serum or urine. In addition, antibodies from various classes or subclasses against these antigens are commercially available and can be appropriately used.

The nucleic acids may be optional complementary DNAs and RNAs, and include, for example, DNAs and RNAs having nucleotide sequences which can be used for pathogenic gene detection, gene diagnosis, etc. These nucleic acids can be chemically synthesized appropriately in a conventional manner.

Taking into account the molecular size of the luciferase of the invention and steric hindrance with the other useful compound, the other useful compound is bound to the luciferase of the invention directly or via a linker or spacer, though it varies depending upon physicochemical properties or the like.

The linker or spacer used in the present invention is not particularly limited as far as it is capable of specifically reacting with the —SH groups, but preferably has a length of 20 angstroms or more. Various reagents for modifying —SH groups which can be used as the linker or spacer are commercially available and can be appropriately utilized.

The crosslinking reagents with a functional group reactive with the thiol group (also called as "sulfhydryl group") of cysteines are not particularly limited. Specific examples are N-(4-[p-azidosalicylamido]butyl]-3'-(2'-pyridyldithio)pro-pionamide (APDP), 1,4-di-(3'-[2'-pyridyldithio]propiona-mide)butane, 1,6-hexane-bis-vinylsulfone (HBVS), succin-imidyl 3-(bromoacetamide)propionate (SBAP), N-succinimidyl 3-(2-pyridyldithio)propionate (SPDP), N-[α-maleimidoacetoacetoxy]succinimide ester (AMAS), succinimidyl 4-(N-maleimidomethyl)cyclohexane (SMCC), sulfonated derivatives of SMCC (sulfo-SMCC), m-maleimi-dobenzoyl-N-hydroxysuccinimide ester (MBS), sulfonated derivatives of MBS (sulfo-MBS), succinimidyl 4-(p-maleimidophenyl)butyrate (SMPB), sulfonated derivatives of SMPB (sulfo-SMPB), succinimidyl 6-(N-maleimido-n-hexanoate), succinimidyl (4-iodoacetyl)aminobenzoate (SIAB), N-hydroxysuccinimidyl bromoacetate, bis-(maleimido)methyl ester, bis-maleimidohexane (BMH), etc. Among the reagents above, crosslinking reagents having a maleimide group as the functional group capable of reacting with the sulfhydryl group are particularly preferred in the present invention.

The reaction of binding the luciferase of the invention to the other useful compound can be carried out by known methods in the art, e.g., by the method described in Hermanson G. T., Bioconjugate Techniques, 2nd Edition (2008), Elsevier Inc., etc. More specifically, when the ligand specific to an analyte is used, it is desired to perform the reaction at 30° C. or less and preferably 25° C. or less, in pH 6 to 8 and preferably pH 7 to 7.5. In the case of the fluorescent substance, it is desired to perform the reaction at 25° C. or less and preferably 4° C. or less, in pH 6 to 8, and preferably pH 7 to 7.5.

Especially when the biotin-conjugated protein is used, it is desired to perform the reaction at 25° C. or less and preferably 4° C. or less, in pH 6 to 8 and preferably pH 7 to 7.5. In the case of the antibody, it is desired to perform the reaction at 25° C. or less and preferably 4° C. or less, in pH 6 to 8 and preferably pH 7 to 7.5. In the case of the nucleic acid, it is desired to perform the reaction at 25° C. or less and preferably 4° C. or less, in pH 6 to 8 and preferably pH 7 to 7.5.

6. Use of Fusion Protein and Complex of the Invention

Use as Detection Marker by Luminescence

The fusion protein of the invention or the complex of the invention can be utilized as a detection marker which emits luminescence in the presence of a luciferin. The detection marker of the present invention can be utilized for detection of the target substance in, e.g., an immunoassay, a hybridization assay, etc. When the complex of the invention is used as a detection marker, the other useful compound in the complex of the invention is a ligand specific to the analyte to be detected.

When the complex of the invention is used in an immunoassay, the ligand to the complex of the invention includes, for example, a primary antibody which specifically recognizes the target substance. The primary antibody in the complex of the invention specifically binds to an analyte (antigen) present in a sample. Thus, the site or amount of the analyte in the sample can be detected by monitoring luminescence of the fusion protein in the complex of the invention.

In order to enhance the detection sensitivity, there is also well known a method of using a secondary antibody which specifically recognizes the primary antibody. In this case, the ligand in the complex of the invention is, e.g., a secondary antibody.

Alternatively, a biotin-conjugated secondary antibody formed by conjugating biotin to a secondary antibody can be reacted with avidin or streptavidin conjugated with the fusion protein of the invention. In this case, the ligand in the complex of the invention is avidin or streptavidin.

Furthermore, the property of binding 1 molecule of avidin or 1 molecule of streptavidin to 4 molecules of biotin can be utilized. More specifically, a biotinylated secondary antibody is reacted with avidin or streptavidin, which is in turn reacted with biotin conjugated to the fusion protein of the invention. In this case, the ligand in the complex of the invention is biotin.

When a receptor is detected using the complex of the invention, a signal peptide (hormones such as insulin, cytokines, TNF, Fas ligands, etc.) can be used as a ligand in the complex of the invention. On the other hand, when the signal peptide is detected, a protein which constitutes the receptor can be used as a ligand in the complex of the invention. That is, in detecting a receptor to which a drug is bound, the drug can be used as the ligand in the complex of the invention, and in detecting a drug bound to a receptor, the receptor can be used as a ligand in the complex of the invention.

When an enzyme is detected using the complex of the invention, a substrate to the enzyme can be used as a ligand in the complex of the invention. On the other hand, when a substrate to the enzyme is detected, the enzyme can be used as a ligand in the complex of the invention.

When the complex of the invention is utilized in a hybridization assay, in order to detect another nucleic acid specifically binding to a certain nucleic acid, a nucleic acid complementary to the nucleic acid to be detected can be used as a ligand in the complex of the invention.

When another substance specifically binding to a polysaccharide is detected using the complex of the invention, the polysaccharide can be used as a ligand in the complex of the invention.

In addition to the foregoing, lectin capable of specifically binding to a blood coagulation factor or a DNA-binding protein such as a transcription factor, etc. can also be used as a ligand in the complex of the invention.

The complex of the invention can be bound directly or indirectly to the target substance via a ligand, as described above, and can thus be utilized as a detection marker which emits light in the presence of a luciferin. Detection of the target substance using such a detection marker can be performed in a conventional manner.

Furthermore, the fusion protein of the invention can be expressed, e.g., as a fusion protein with a target protein, and introduced into cells by means of the microinjection method, etc., and the resulting product can be used to determine distribution of the target protein described above. The distribution of such a target protein or the like can be determined by using detection methods such as luminescence imaging. In addition to the introduction into cells by means of the microinjection method or the like, the fusion protein of the invention can be expressed in cells and provided for use.

Use as Reporter Protein

The fusion protein of the invention may also be used as a reporter protein to assay the transcription activity of promoters, etc. The polynucleotide encoding the fusion protein of the invention (i.e., the polynucleotide of the invention) is fused to a target promoter or some other expression control sequence (e.g., an enhancer, etc.) to construct a vector. By introducing the vector into a host cell and detecting the luminescence from the fusion protein of the invention in the presence of a luciferin, the activity of the target promoter or some other expression control sequence can be assayed.

The polynucleotide of the invention can be used as a reporter gene in such a manner as described above.

Material for Amusement Supplies

The fusion protein of the invention has the activity of catalyzing the reaction where luciferin is oxidized with oxygen molecules to form oxyluciferin in its excited state. The oxyluciferin in the excited state emits visible light to decay to the ground state. Accordingly, the fusion protein, etc. of the invention can be used preferably as a luminescent material for amusement supplies. Examples of such amusement supplies are luminescent soap bubbles, luminescent ice bars, luminescent candies, luminescent color paints, etc. These amusement supplies can be prepared in a conventional manner.

Bioluminescence Resonance Energy Transfer (BRET) Method

By utilizing the principle of interaction between molecules by the bioluminescence resonance energy transfer (BRET) method, the fusion protein of the invention or the complex of the invention is available for analytical methods such as analysis of physiological functions, assay of enzyme activities, etc.

For instance, when the fusion protein of the invention or the complex of the invention (sometimes referred to as "the luciferase of the invention") is used as a donor and the fluorescent substance (e.g., an organic compound, a fluorescent protein, etc.) is used as an acceptor, the interactions between the donor and acceptor above can be detected by causing bioluminescence resonance energy transfer (BRET) between them.

In an embodiment of the present invention, the organic compound used as an acceptor includes Hoechist3342, Indo-1, DAP1, etc. In another embodiment of the present invention, the fluorescent protein used as an acceptor includes a green fluorescent protein (GFP), a blue fluorescent protein (BFP), a mutant GFP fluorescent protein, phycobilin, etc.

In a preferred embodiment of the present invention, the physiological functions to be analyzed include an orphan receptor (especially, a G protein-coupled receptor), apoptosis, transcription regulation by gene expression, etc. Further in a preferred embodiment of the present invention, the enzyme to be analyzed is protease, esterase, kinase, or the like.

Analysis of the physiological functions by the BRET method can be performed by known methods, for example, by modifications of the methods described in Biochem. J. 2005, 385, 625-637, Expert Opin. Ther Tarets, 2007 11: 541-556, etc. Measurement of enzyme activities may also be performed by known methods, for example, by modifications of the methods described in Nature Methods 2006, 3:165-174, Biotechnol. J. 2008, 3:311-324, etc.

In the complex of some embodiments of the present invention, the fusion protein of the invention is conjugated with the fluorescent substance as the other useful compound. The fluorescent substance includes those described above. When the fusion protein is used as a donor in the complex of the invention and the fluorescent substance is used as an acceptor in the same complex, BRET can also be caused between them.

7. Kit of the Invention

The present invention further provides a kit comprising any one selected from the fusion protein of the invention, the polynucleotide of the invention, the recombinant vector of the invention, the transformant of the invention and the complex of the invention. The kit of the present invention may further contain a luciferin (e.g., a coelenterazine analogue). The kit of the present invention can be prepared with conventional materials by conventional methods. The kit of the present invention may further contain sample tubes, plates, instructions for the kit user, solutions, buffers, reagents, and samples suitable for standardization or control samples. The kit of the present invention may further contain salts including halide ions.

The kit of the present invention can be used for the aforesaid measurement using a reporter protein or a reporter gene, the analysis of physiological functions or measurement of enzyme activities by the BRET method.

8. Method for Luminescence Reaction

Catalytic Ability for Luminescence Activity

The fusion protein of the invention or the complex of the invention (hereinafter sometimes referred to as "the fusion protein, etc. of the invention") has the ability of catalyzing the reaction in which a luciferin (e.g., a coelenterazine analogue) is oxidized with oxygen molecules to form an oxyluciferin in its excited state. The oxyluciferin in the excited state emits light on returning to the ground state. That is, the fusion protein, etc. of the invention catalyzes the luminescence reaction in which a luciferin (e.g., a coelenterazine analogue) serves as a substrate to cause luminescence. This activity is sometimes referred to as "the catalytic ability for the luminescence activity."

Luminescence Reaction

The luminescence reaction using the fusion protein, etc. of the invention in which a luciferin (e.g., a coelenterazine analogue) serves as a substrate can be performed by contacting the fusion protein, etc. of the invention with the luciferin. The reaction can be carried out under conditions conventionally used for the luminescence reaction using Gaussia luciferase or under those modified therefrom (see, e.g., WO 99/49019, J. Biol. Chem. 279, 3212-3217 (2004) and the documents cited therein, etc.).

Specifically, solvents for the reaction which are employed are, for example, a buffer solution such as Tris-HCl buffer, sodium phosphate buffer, etc., water, and the like.

Temperatures for the reaction are generally at approximately 4° C. to 40° C. and preferably approximately 4° C. to 25° C.

In the reaction solution, pH is generally approximately 5 to 10, preferably approximately 6 to 9, more preferably approximately 7 to 8 and most preferably approximately 7.5

Coelenterazine analogues are preferred as the luciferin, with particular preference being coelenterazine.

The luciferin may also be added to the reaction system in the form of a solution in a polar solvent such as dimethylformamide, dimethylsulfoxide, etc., or in an alcohol such as methanol, ethanol, butanol, etc.

Activation of Luminescence Activity

The luminescence activity of the fusion protein, etc. of the invention where the luciferin (e.g., coelenterazine analogue) serves as a substrate is activated by halide ions.

Examples of the halide ions are fluorine ions, chlorine ions, bromine ions and iodine ions; preferred are chlorine ions, bromine ions and iodine ions.

The concentration of the halide ions is generally approximately 10 µM to 100 mM, preferably approximately 100 µM to 50 mM and particularly preferably approximately 1 mM to 20 mM.

To add the halide ions to the reaction system, there is a method which comprises adding them in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI, KF, KCl, KBr, KI, $CaF_2$, $CaCl_2$, $CaBr_2$, $CaI_2$, $MgF_2$, $MgCl_2$, $MgBr_2$, $MgI_2$, etc.

Unless otherwise indicated with respect to the embodiments and working examples, the methods described in standard sets of protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., or modifications or variations thereof are used. When commercially available reagent kits or measuring apparatuses are used, protocols attached to them are used unless otherwise indicated.

Regardless of their purposes, all of the documents and publications described in the specification are incorporated herein by reference, each in its respective entirety.

The objects, characteristics and advantages of the present invention as well as the idea thereof are apparent to those skilled in the art from the descriptions given herein. Based on the description given herein, those skilled in the art can easily work the present invention. It is to be understood that the best mode for carrying out the invention, specific working examples, etc. are to be taken as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to EXAMPLES below but is not deemed to limit the invention thereto.

Example 1

Construction of Novel Expression Vector having Hinge Sequence in Yeast

A novel expression vector having a hinge sequence was constructed as follows. First, the following linkers, pPICZα Linker-F and pPICZα Linker-R having chemically synthesized multicloning sequences were inserted into the restriction enzyme XhoI/SalI sites in pPICZα A (Invitrogen) to construct the novel vector pPICZα-Linker.

pPICZα Linker-F (5' TC GAA AAA AGA GAG GCT GAA GCT GGT ACC GAA TTC CTG CAG CTC GAG TCT AGA G 3') (SEQ ID NO: 9)

pPICZα Linker-R (5' TC GAC TCT AGA CTC GAG CTG CAG GAA TTC GGT ACC AGC TTC AGC CTC TCT TTT T 3') (SEQ ID NO: 10)

Next, the following linkers: hinge Linker-F and hinge Linker-R containing a chemically synthesized multicloning sequence were inserted into the restriction enzyme PstI/SalI sites of the pPICZα-Linker vector to construct the novel expression vector pPICZα-hgLinker having a hinge sequence, which is shown in FIG. 1.

hinge Linker-F (5' G AGC TTA TCC ACC CCG CCG ACC CCG TCC CCG TCC ACC CCG CCG TGC CTC GAG TCT AGA G 3'; the new cysteine residue underlined) (SEQ ID NO: 11)

hinge Linker-R (5' TC GAC TCT AGA CTC GAG GCA CGG CGG GGT GGA CGG GGA CGG GGT CGG CGG GGT GGA TAA GCT CTG CA 3'; the newly introduced cysteine residue underlined) (SEQ ID NO: 12)

The insert DNA was confirmed by nucleotide sequencing on a DNA Sequencer (manufactured by ABI). The DNA sequence of the expression vector pPICZα-hgLinker is shown by SEQ ID NO: 1. The amino acid sequence of a protein encoded by the DNA sequence of the expression vector pPICZα-hgLinker is shown by SEQ ID NO: 2.

Example 2

Construction and Gaussia Luciferase Expression Vector in Yeast

The Gaussia luciferase expression vector with a hinge sequence for the purpose of expression in yeast was constructed as follows. Using pcDNA3-hGL as a template, PCR was performed (cycle conditions of 25 cycles: 1 min/94° C., 1 min/50° C. and 1 min/72° C.) using the two PCR primers shown below to amplify the desired DNA region.

Primer: GL6-N/EcoRI (5' gcc GAA TTC AAG CCC ACC GAG AAC AAC GAA 3') (SEQ ID NO: 13)

Primer: GL26C-TAA/PstI (5' ggc CTGCAG GTC ACC ACC GGC CCC CTT GAT 3') (SEQ ID NO: 14)

The resulting fragment was purified by a PCR Purification Kit (manufactured by Qiagen). After digestion with restriction enzymes EcoRI/PstI in a conventional manner, the fragment was ligated to the pPICZα-hgLinker constructed in EXAMPLE 1 at the restriction enzyme EcoRI/PstI sites. The yeast expression vector pPICZα-hgGL-H shown in FIG. 2 was thus constructed.

The insert DNA was confirmed by nucleotide sequencing on a DNA Sequencer (manufactured by ABI). The DNA sequence encoding the hg-Gaussia luciferase fusion protein inserted into the expression vector pPICZα-hgGL-His shown by SEQ ID NO: 3. The amino acid sequence of the hg-Gaussia luciferase fusion protein inserted into the expression vector pPICZα-hgGL-His shown by SEQ ID NO: 4.

For expression in yeast, the expression vector pPICZα-hgGL-H was introduced into yeast X33 strain (manufactured by Invitrogen) on a conventional electroporation apparatus (manufactured by Bio-Rad) and cultured at 30° C. for 2 days on agar of YM medium (manufactured by Difco) containing Zeocin (100 mg/ml) to obtain the transformant. The transformant was cultured at 30° C. for 18 hours in liquid YM medium (manufactured by Difco) containing 10 ml of Zeocin (100 mg/ml). After centrifugation, the bacterial cells were isolated. Coelenterazine (Chisso Corporation, hereinafter the same) as a luminescence substrate was added to the supernatant to confirm the luminescence activity.

Example 3

Construction of Gaussia Luciferase Expression Vector in E. coli

The Gaussia luciferase expression vector with a hinge sequence for the purpose of expression in E. coli was constructed as follows. The expression vector pPICZα-hgGL-H constructed in EXAMPLE 2 was digested with restriction enzymes Asp718I/XbaI in a conventional manner. The resulting fragment was inserted into pColdII (manufactured by Takara-Bio) at the restriction enzyme Asp718I/XbaI sites to construct the expression vector pCold-hgGL shown in FIG. 3.

The insert DNA was confirmed by nucleotide sequencing on a DNA Sequencer (manufactured by ABI). The DNA sequence encoding the hg-Gaussia luciferase fusion protein, which was inserted into the expression vector pCold-hgGL, is shown by SEQ ID NO: 5. The amino acid sequence of the hg-Gaussia luciferase fusion protein, which was inserted into the expression vector pCold-hgGL, is shown by SEQ ID NO: 6.

Example 4

Construction of Gaussia Luciferase Expression Vector having a Hinge Sequence and an Avidin Tag Sequence in E. coli Gaussia luciferase expression vector having a hinge sequence and an avidin tag sequence was constructed as follows. The following linkers Avitag-Xho/Xba-F and Avi-Tag-Xho/Xba-R having a chemically synthesized multicloning site were inserted into the XhoI/XbaI sites, which are the restriction enzyme sites for the expression vector pColdhgGL constructed in EXAMPLE 3. Thus, novel expression vector pCold-hgA-GL shown in FIG. 4 was constructed.

Avitag-Xho/Xba-F (5' TC GAG GGT CTG AAC GAC ATC TTC GAA GCT CAG AAA ATC GAA TGG CAC GAA T 3') (SEQ ID NO: 15)

AviTag-Xho/Xba-R (5' CT AGA TTC GTG CCA TTC GAT TTT CTG AGC CTC GAA GAT GTC GTT CAG ACC C 3') (SEQ ID NO: 16)

The insert DNA was confirmed by nucleotide sequencing on a DNA Sequencer (manufactured by ABI). The DNA sequence encoding the hg-Gaussia luciferase fusion protein, which was inserted into the expression vector pCold-hgA-GL, is shown by SEQ ID NO: 7. The amino acid sequence of the hg-Gaussia luciferase fusion protein, which was inserted into the expression vector pCold-hgA-GL, is shown by SEQ ID NO: 8.

Example 5

Expression and Purification of Recombinant Gaussia Luciferase having the Hinge Sequence from E. coli The recombinant hg-Gaussia luciferase having the hinge sequence (hg-Gaussia luciferase) was expressed in E. coli using the expression vector pCold-hgGL. The recombinant hg-Gaussia luciferase was purified by nickel-chelate column chromatography and then hydrophobic column chromatography.

1) Expression of Recombinant hg-Gaussia Luciferase Having the Hinge Sequence in E. coli To express the recombinant hg-Gaussia luciferase in E. coli, the Gaussia luciferase gene expression vector pCold-hgGL constructed in EXAMPLE 3 was used. The expression vector was transformed into the E. coli BL21 strain in a conventional manner. The transformant obtained was inoculated in 10 ml of LB liquid medium (10 g of bactotryptone, 5 g of yeast extract and 5 g of sodium chloride per 1 liter of water, pH 7.2) containing ampicillin (50 μg/ml) and incubated at 37° C. for 18 hours. Subsequently, the culture broth was added to 400 ml×5 (2000 ml in total) of a fresh LB liquid medium. After culturing at 37° C. for 5 hours, the mixture was cooled on an ice water. Isopropyl-β-D(−)-thiogalactopyranoside (IPTG, manufactured by Wako Pure Chemical Industry) was added to the culture to a final concentration of 0.1 mM, followed by incubation at 15° C. for 17 hours. The cells were recovered by centrifugation (5,000 rpm, 5 mins.) and provided for use as the starting material for protein extraction.

2) Extraction of hg-Gaussia Luciferase from Supernatant of Cultured Cells and Nickel-Chelate Gel Column Chromatography The cultured cells collected were suspended in 200 ml of 50 mM Tris-HCl (pH 7.6) and disrupted by ultrasonication (manufactured by Branson, Sonifier Model Cycle 250) 3 times each for 3 minutes under ice cooling. The cell lysate was centrifuged at 10,000 rpm (12,000×g) at 4° C. for 20 minutes. The resultant soluble fractions were applied on a nickel-chelate column (Amersham Bioscience, column size: diameter 2.5×6 cm) equilibrated with 50 mM Tris-HCl (pH 7.6) to adsorb hg-Gaussia luciferase. After washing with 300 ml of 50 mM Tris-HCl (pH 7.6), hg-Gaussia luciferase was eluted with 0.1M imidazole (manufactured by Wako Pure Chemical Industry). From 800 ml of the cultured cells, 50.4 mg of hgGL was obtained. As a result of SDS-PAGE analysis, the purity was estimated to be over 95%

3) Purification of hg-Gaussia Luciferase by Hydrophobic Column Chromatography

After $(NH_4)_2SO_4$ was added to 63 ml of the fraction (50.4 mg as the protein) eluted from the nickel-chelate gel column to a final concentration of 1.2 M, the mixture was centrifuged at 10,000 rpm (12,000×g) at 4° C. for 20 minutes. The resultant soluble fractions were applied to a butyl-Sepharose column (Amersham Bioscience, column size: diameter 2.5×5.5 cm) equilibrated with 10 mM Tris-HCl (pH 7.6) to adsorb hg-Gaussia luciferase thereto. After washing with 110 ml of 10 mM Tris-HCl (pH 7.6) containing 1.2 M $(NH_4)_2SO_4$ and 2 mM EDTA, hg-Gaussia luciferase was eluted with 10 mM Tris-HCl (pH 7.6) containing 0.4M $(NH_4)_2SO_4$ and 2 mM EDTA, and 6.5 mg of hg-Gaussia luciferase was obtained. As a result of SDS-PAGE analysis, the purity was estimated to be over 95%.

4) Quantification of Protein Concentration

Protein concentration was determined by the method of Bradford using a commercially available kit (manufactured by Bio-Rad) and bovine serum albumin (manufactured by Pierce) as a standard.

Figure 5:
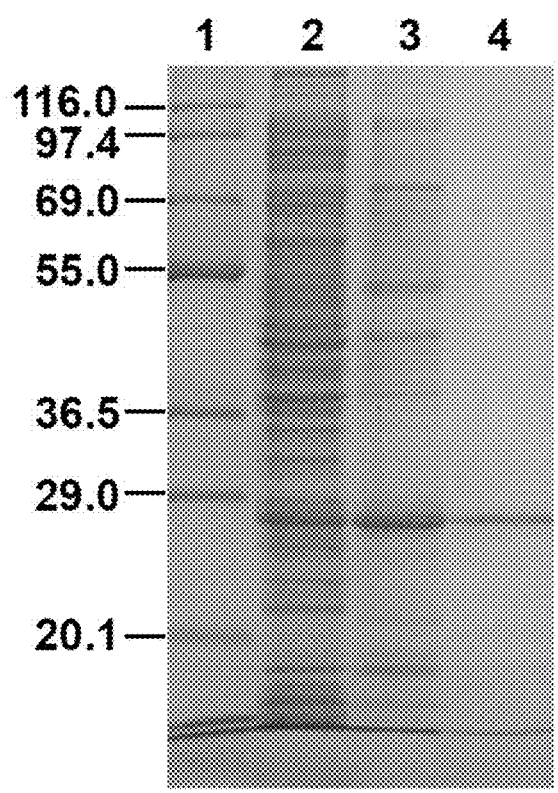
FIG. 5 shows the results of SDS-PAGE analysis in the process of purification from the soluble fractions of hg-Gaussia luciferase. Lane 1: protein molecular weight marker (Tefco), Lane 2: supernatant obtained by centrifuging the ultrasonicated lysate of the transformant from pCold-hg-Gaussia luciferase-expressed E. coli at 12,000 g for 20 minutes (protein concentration, 18.5 µg), Lane 3: fraction eluted from a nickel-chelate column (protein concentration, 7.4 µg), Lane 4: fraction eluted from a butyl column (protein concentration, 1.1 µg).

For the fraction in each purification step, SDS-PAGE analysis was performed on a 12% polyacrylamide gel under reducing conditions. As shown in FIG. 5, the results revealed that a single band corresponding to the protein of 22 kDa molecular weight was detected and the purity was over 95%. The activity recovery of hg-Gaussia luciferase from the soluble fraction obtained from 2000 ml of cultured cells was 38.4% and the yield was 6.5 mg.

5) Determination of Luminescence Activity

After 1 μl of a Gaussia luciferase solution was added to 0.1 ml of PBS (manufactured by Sigma; 0.137M sodium chloride and 0.0027M potassium chloride, pH 7.4) supplemented with 0.01% Tween 20 and 10 mM EDTA (manufactured by Wako Pure Chemical Industry) (hereinafter referred to as PBST-E), which contained 0.5 μg of substrate coelenterazine, the luminescence activity of Gaussia luciferase was measured for 10 seconds using a luminescence luminometer: Luminescencer-PSN AB2200 (manufactured by Atto). The luminescence activity is shown in terms of the maximum intensity (Imax).

TABLE 1

| | Purification of hg-Gaussia Luciferase | | | | | |
|---|---|---|---|---|---|---|
| | Total amount | Total protein concentration | Total activity | Specific activity | Recovery rate (%) | |
| Step | (ml) | (mg) | ($\times 10^9$ rlu) | ($\times 10^9$/mg) | Protein | Activity |
| Crude extract from the soluble fractions | 200 | 760 | 178.4 | 0.24 | 100 | 100 |
| Nickel-chelate gel | 63 | 50.4 | 111.5 | 2.21 | 6.6 | 62.5 |
| Butyl-Sepharose gel | 39 | 6.5 | 68.5 | 10.6 | 0.9 | 38.4 |

Example 6

Expression and Purification of Recombinant Gaussia Luciferase Having the Avidin Tag Sequence from E. coli The recombinant Gaussia luciferase having the avidin tag sequence (hgA-Gaussia luciferase) was expressed in E. coli using the expression vector pCold-hgA-GL. The hgA-Gaussia luciferase was purified by nickel-chelate column chromatography and then hydrophobic chromatography.

1) Expression of Recombinant hgA-Gaussia Luciferase having the Avidin Tag Sequence in E. Coli The Gaussia luciferase gene expression vector pCold-hgA-GL constructed in EXAMPLE 4 was used to express the recombinant hgA-Gaussia luciferase in E. coli. The expression vector was transformed into the E. coli BL21 strain in a conventional manner. The transformant obtained was inoculated into 10 ml×2 tubes of LB liquid medium (10 g of bactotryptone, 5 g of yeast extract and 5 g of sodium chloride per 1 liter of water, pH 7.2) containing ampicillin (50 µg/ml), followed by incubation at 37° C. for 18 hours. Next, the culture broth was added to 400 ml×2 tubes of fresh LB liquid medium (800 ml in total). After incubation at 37° C. for 3 hours, the culture broth was cooled in ice water. Isopropyl-β-D(-)-thiogalactopyranoside (IPTG, manufactured by Wako Pure Chemical Industry) was added to the culture broth to a final concentration of 0.1 mM, followed by incubation at 15° C. for 19 hours. After the incubation, the cells were recovered by centrifugation (5,000 rpm, 5 mins.) and provided for use as the starting material for protein extraction.

2) Extraction of hgA-Gaussia Luciferase from Supernatant of Cultured Cells and Nickel-Chelate Column Chromatography The cultured cells collected were suspended in 80 ml of 50 mM Tris-HCl (pH 7.6) and disrupted by ultrasonication (manufactured by Branson, Sonifier Model Cycle 250) 4 times each for 3 minutes under ice cooling. The cell lysate was centrifuged at 10,000 rpm (12,000×g) at 4° C. for 20 minutes. The resultant soluble fractions were applied onto a nickel-chelate column (Amersham Bioscience, column size: diameter 2.5×6 cm) equilibrated with 50 mM Tris-HCl (pH 7.6) to adsorb hgA-Gaussia luciferase. After washing with 50 mM Tris-HCl (pH 7.6), hgA-Gaussia luciferase was eluted with 0.1M imidazole (manufactured by Wako Pure Chemical Industry). From 800 ml of the cultured cells, 19.9 mg of hgA-Gaussia luciferase was obtained.

3) Purification of hgA-Gaussia Luciferase by Hydrophobic Column Chromatography

After $(NH_4)_2SO_4$ was added to 39 ml of the fraction (19.9 mg as the protein) eluted from the nickel-chelate column to a final concentration of 1.2 M, the mixture was centrifuged at 10,000 rpm (12,000×g) at 4° C. for 20 minutes. The resultant soluble fractions were applied to a butyl-Sepharose column (Amersham Bioscience, column size: diameter 2.5×5.5 cm) equilibrated with 10 mM Tris-HCl (pH 7.6) to adsorb hgA-Gaussia luciferase. After washing with 10 mM Tris-HCl (pH 7.6) containing 1.2 M $(NH_4)_2SO_4$ and 2 mM EDTA, hgA-Gaussia luciferase was eluted with 10 mM Tris-HCl (pH 7.6) containing 0.4 M $(NH_4)_2SO_4$ and 2 mM EDTA to give 0.92 mg of hgA-Gaussia luciferase. As a result of SDS-PAGE analysis, the purity was estimated to be 95% or more.

4) Quantification of Protein Concentration

Protein concentration was determined by the method of Bradford using a commercially available kit (manufactured by Bio-Rad) and bovine serum albumin (manufactured by Pierce) as a standard.

Figure 6:
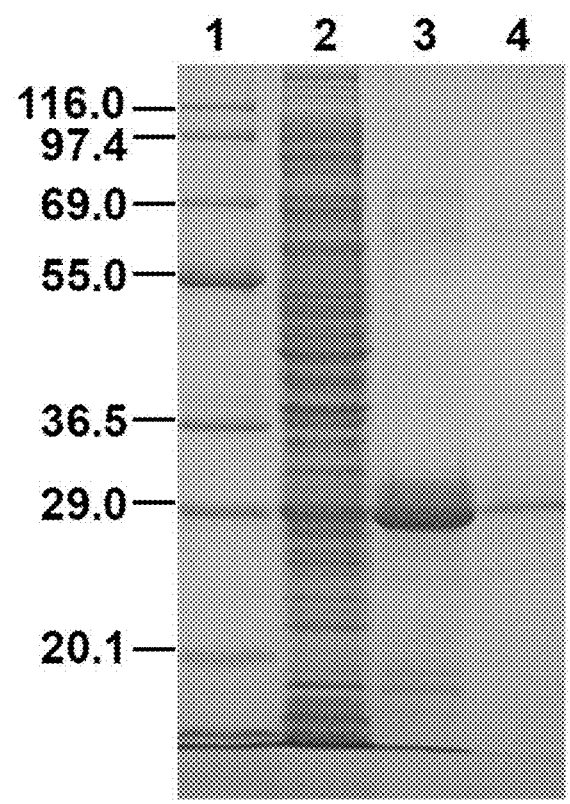
FIG. 6 shows the results of SDS-PAGE analysis in the process of purification from the soluble fractions of hgA-Gaussia luciferase. Lane 1: protein molecular weight marker (Tefco), Lane 2: supernatant obtained by centrifuging the ultrasonicated lysate of the transformant from pCold-hgA- Gaussia luciferase-expressed *E. coli* at 12,000 g for 20 minutes (protein concentration, 17.7 μg), Lane 3: fraction eluted from a nickel-chelate column (protein concentration, 14.5 μg), Lane 4: fraction eluted from a butyl column (protein concentration, 0.72 μg).

SDS-PAGE analysis of the fraction in each purification step was performed on a 12% polyacrylamide gel under reducing conditions. As shown in FIG. 6, the results revealed that a single band corresponding to the protein of 29 kDa molecular weight was detected and the purity was over 95%. The activity recovery rate of hgA-Gaussia luciferase from 800 ml of the cultured cells was 15.8% and the yield was 0.92 mg.

5) Determination of Luminescence Activity

After 1 µl of a Gaussia luciferase solution was added to 0.1 ml of PBS (manufactured by Sigma; 0.137 M sodium chloride and 0.0027 M potassium chloride, pH 7.4) supplemented with 0.01% Tween 20 and 10 mM EDTA (manufactured by Wako Pure Chemical Industry) (hereinafter referred to as PBST-E), which contained 0.5 µg of substrate coelenterazine, the luminescence activity was measured for 10 seconds using an apparatus for measuring luminescence: Luminescencer-PSN AB2200 (manufactured by Atto). The luminescence activity is shown in terms of the maximum intensity (Imax).

TABLE 2

Purification of hgA-Gaussia Luciferase

| Step | Total amount (ml) | Total protein concentration (mg) | Total activity (×10$^9$ rlu) | Specific activity (×10$^9$/mg) | Recovery rate (%) Protein | Recovery rate (%) Activity |
|---|---|---|---|---|---|---|
| Crude extract from the soluble fractions | 80 | 224 | 55.6 | 0.25 | 100 | 100 |
| Nickel-chelate gel | 39 | 19.9 | 63.4 | 3.19 | 8.9 | 114 |
| Butyl-Sepharose gel | 40 | 0.92 | 8.8 | 9.57 | 0.09 | 15.8 |

Example 7

Preparation of Biotinylated hg-Gaussia Luciferase by Maleimide-Activated Biotin To 500 µl of a PBS solution supplemented with 1 mM EDTA (hereinafter referred to as PBS-E), 4.4 µl (4.4 nmol) of maleimide-activated biotin (manufactured by Pierce, EZ-Link PEO-Maleimide-Activated Biotin; spacer length: 29.1 angstroms) adjusted to 1 mM with PBS-E, wad added and then 500 µl (2.2 nmol) of the purified hg-Gaussia luciferase was added to initiate a modification reaction. The reaction was conducted at 25° C. overnight in the dark. A cysteine solution was added thereto to a final concentration of 0.2 mM. The mixture was allowed to stand at room temperature for 30 minutes to inactivate the unreacted maleimide-activated biotin. The inactivated maleimide biotin reagent was removed using an Amicon Ultra column (manufactured by Millipore). The biotinylated hg-Gaussia luciferase was thus prepared.

The luminescence activity was compared between the biotinylated hg-Gaussia luciferase obtained as described above and hg-Gaussia luciferase before the reaction. As a result, there is no significant loss on the luminescence activity due to biotinylation; the biotinylated hg-Gaussia luciferase retained the luminescence activity of 98% or more.

Example 8

Figure 7:
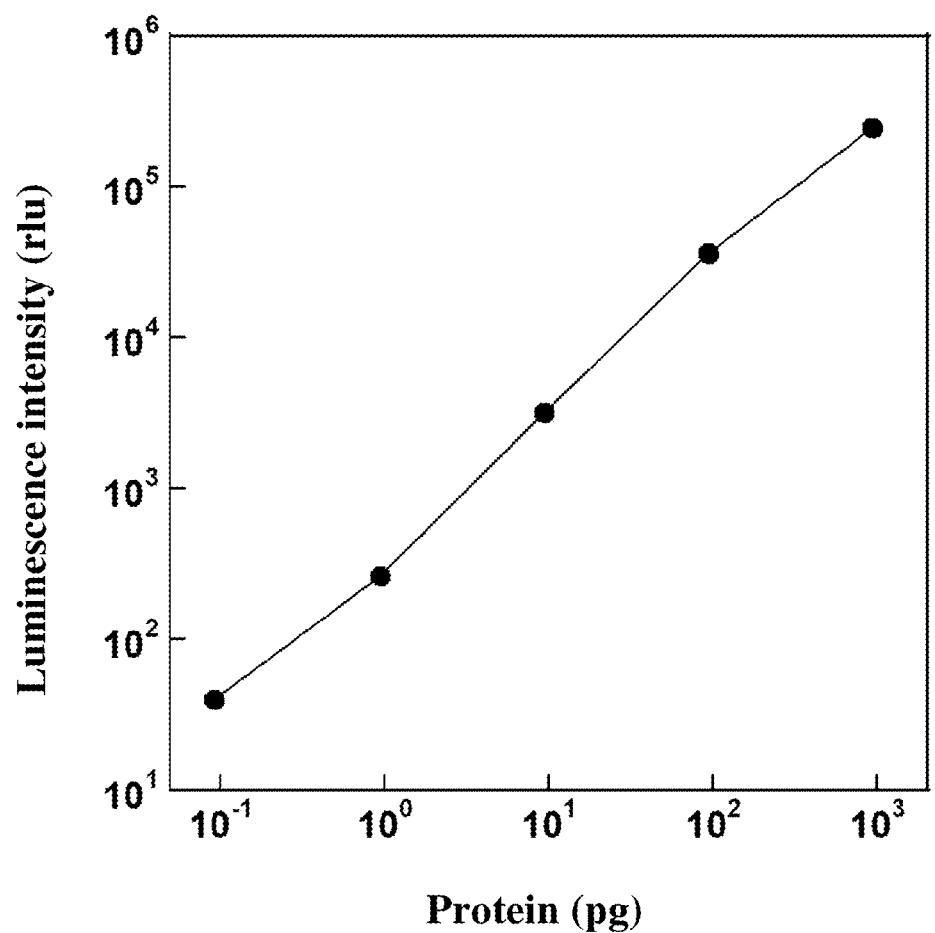
FIG. 7 shows the relationship between the concentration and luminescence intensity of biotinylated hg-Gaussia luciferase.

Correlation Between Protein Concentration and Luminescence Activity of Biotinylated hg-Gaussia Luciferase In order to use the biotinylated hg-Gaussia luciferase as a detection probe, it is required that the protein concentration and the luminescence activity are in a linear correlation. The biotinylated hg-Gaussia luciferase was diluted to a concentration in a range from 100 femtograms to 1 nanogram, 100 μl of substrate coelenterazine (0.5 ng/μl) was injected, and the luminescence activity was measured on an apparatus for measuring luminescence Centro LB960 (manufactured by Berthold). The correlation between the maximum luminescence intensity (Imax) and the protein concentration is shown in FIG. 7. The linear correlation was observed between the luminescence intensity and biotinylated hg-Gaussia luciferase. The results reveal that the amount of biotinylated hg-Gaussia luciferase can be quantitatively determined by luminescence.

Example 9

Luminescent Immunoassay of α-Fetoprotein (AFP) Using Biotinylated hg-Gaussia Luciferase 1) Coating of Anti-Fetoprotein Antibody (Anti-AFP Antibody)

The anti-AFP antibody (manufactured by Japan Clinical Laboratories, Inc., Clone No. 6D2, subclass IgG2a-κ, hereinafter referred to as "6D2") was prepared at a concentration of 5 μg/ml, using 50 mM carbonate buffer solution (pH 9.6) containing 0.05% sodium azide. The solution was dispensed into a 96-well microplate (manufactured by Nunc, #437796) in an amount of 100 μl/well and allowed to stand at room temperature overnight for coating. After the standing, the carbonate buffer solution was withdrawn, a solution of 150 mM NaCl (manufactured by Wako Pure Chemical Industry) and 20 mM Tris-HCl (manufactured by Wako Pure Chemical Industry) (hereinafter referred to as TBS) containing 1% bovine serum albumin (manufactured by Sigma, hereinafter referred to as BSA), 2 mM EDTA (EDTA.2Na, manufactured by Dojin Chemical Laboratory) and 0.05% sodium azide (manufactured by Wako Pure Chemical Industry) (hereinafter referred to as a post-coating solution) was dispensed in an amount of 200 μl/well, which was then allowed to stand at 4° C. overnight.

2) Detection of AFP by Biotinylated hg-Gaussia Luciferase

Figure 8:
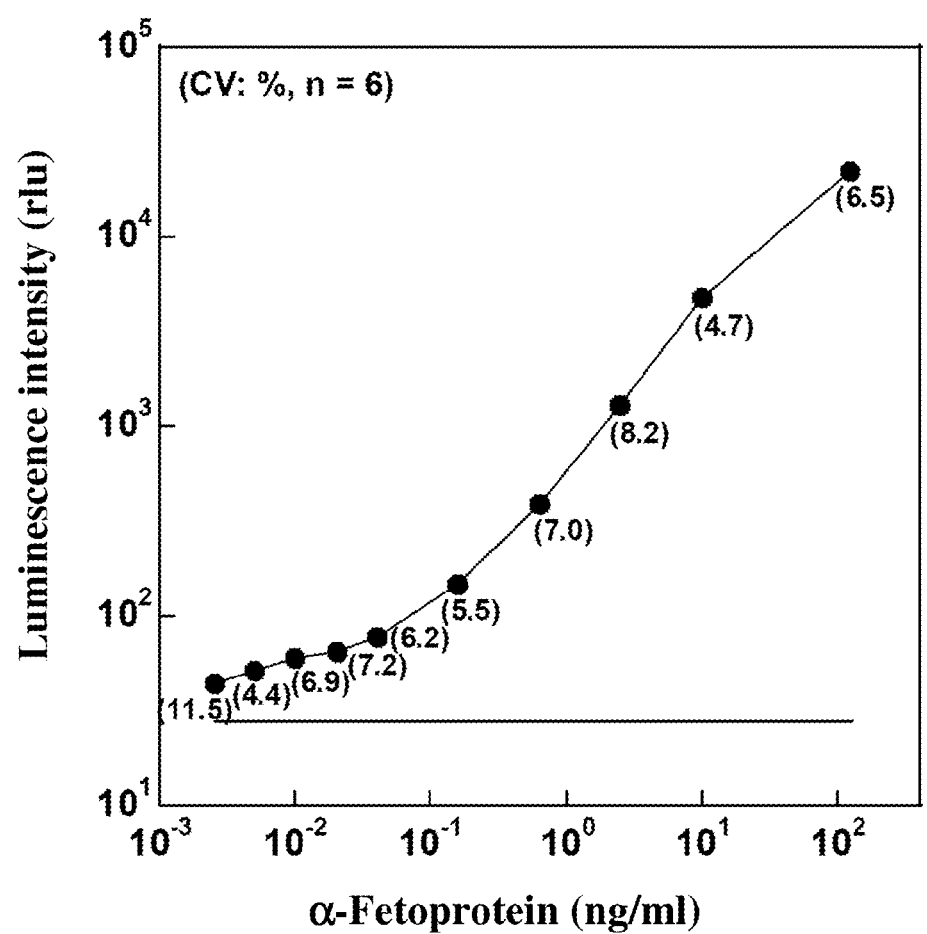
FIG. 8 shows the standard curve of AFP obtained using biotinylated hg-Gaussia luciferase, wherein the solid line represents the background concentration, indicating a mean value+3SD when the concentration of AFP is 0 ng/ml.

After the standing, the post-coating solution was removed. The wells were washed 3 times with 340 μl of TBS containing 0.01% Tween 20 and 2 mM EDTA (referred to as TBST-E), α-fetoprotein (manufactured by Dako, abbreviated as AFP), which was diluted from 0.0125 ng/ml to 125 ng/ml with TBS containing 10% Block Ace (manufactured by Snow Brand Milk Products) and 2 mM EDTA, was dispensed into a 96-well microplate in an amount of 50 μl/well. The biotinylated anti-AFP antibody (manufactured by Japan Clinical Laboratories, Inc., Clone No. 1D5, subclass IgG1-κ, hereinafter referred to as "1D5") diluted to 74.5 ng/ml, was further dispensed in an amount of 50 μl/well, which was then allowed to stand at 30° C. for an hour. The reaction solution was withdrawn from the plate described above and the wells were washed 3 times with 340 μl of TBST-E. Next, 50 μl of streptavidin diluted to 200 μmol/ml with PBS containing 10% Block Ace, 0.01% Tween 20 (manufactured by Bio-Rad) and 10 mM EDTA (hereinafter referred to as PBSE-TB) was mixed with 50 μl of the biotinylated hg-Gaussia luciferase diluted to 400 pmol/ml. The mixture was reacted at room temperature for 30 minutes. Thereafter, the solution diluted to 80-fold with PBSE-TB was dispensed onto the plate above in an amount of 100 μl/well. The mixture was allowed to stand at 30° C. for 30 minutes. The reaction solution was removed and the wells were washed 3 times with 340 μl of TBST-E. Then, substrate coelenterazine diluted with PBST-E to 0.5 ng/μl was injected into the wells in an amount of 100 μl/well. The luminescence intensity was measured on an apparatus for measuring luminescence Centro LB960 (manufactured by Berthold) for 10 seconds in 0.1 second intervals to determine the maximum luminescence intensity (Imax). The standard curve of AFP obtained from the Imax and AFP concentration is shown in FIG. 8.

Example 10

Preparation of Biotinylated hgA-Gaussia Luciferase by Maleimide-Activated Biotin To 650 μl of PBS-E, 4.2 μl (4.2 nmol) of maleimide-activated biotin (manufactured by Pierce, EZ-Link PEO-Maleimide-Activated Biotin; spacer length: 29.1 angstroms) adjusted to 1 mM with PBS-E, wad added and then 350 μl (2.1 nmol) of the purified hgA-Gaussia luciferase was added to initiate a modification reaction. The reaction was carried out at 25° C. for 2 hours in the dark. A cysteine solution was added thereto to a final concentration of 0.2 mM. The mixture was allowed to stand at room temperature for 30 minutes to inactivate the unreacted maleimide-activated biotin. The inactivated maleimide biotin reagent was removed using an Amicon Ultra column (manufactured by Millipore). The biotinylated hgA-Gaussia luciferase was thus prepared.

The luminescence activity was compared between the biotinylated hgA-Gaussia luciferase obtained as described above and hgA-Gaussia luciferase before the reaction. As a result, there is no significant effect on the luminescence activity due to biotinylation and the biotinylated hgA-Gaussia luciferase retained the luminescence activity of 98% or more.

Example 11

Quantitative Property of Biotinylated hgA-Gaussia Luciferase

Figure 9:
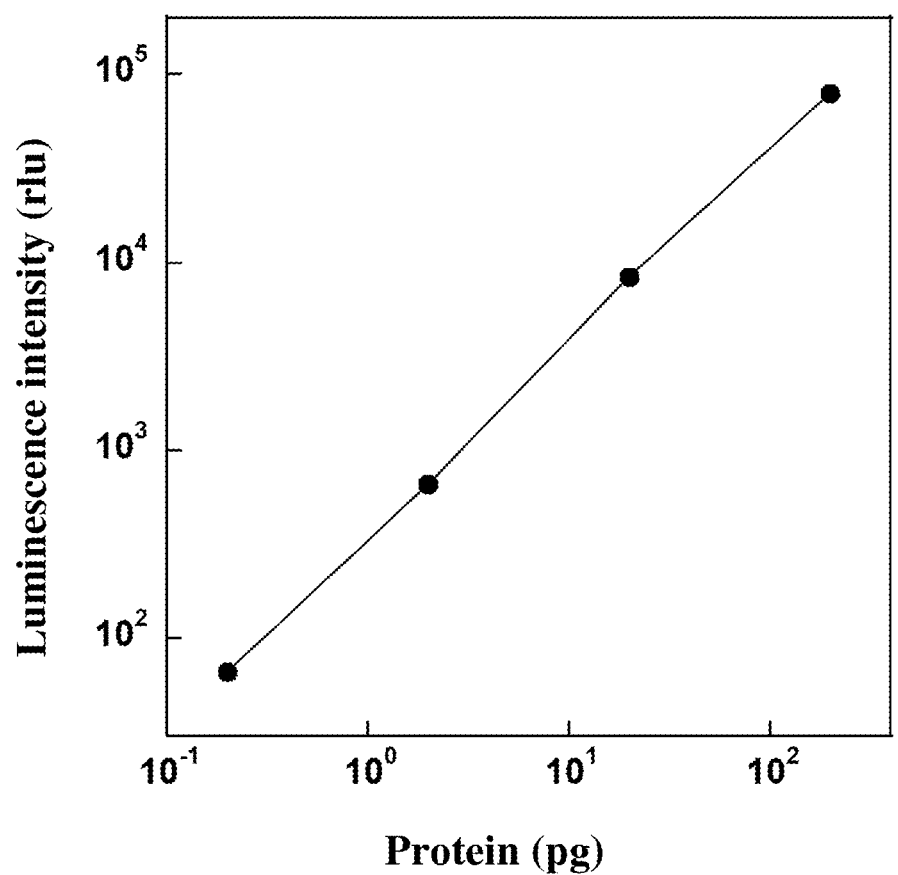
FIG. 9 shows the relationship between the concentration and luminescence intensity of biotinylated hgA-Gaussia luciferase.

In order to use the biotinylated hgA-Gaussia luciferase as a detection probe, it is required that the protein concentration and the luminescence activity are in a linear correlation. The biotinylated hgA-Gaussia luciferase mutant was diluted to a concentration in a range from 200 femtograms to 200 picograms, and 100 μl of substrate coelenterazine (0.5 ng/μl) was injected therein. The luminescence activity was measured with an apparatus for measuring luminescence Centro LB960 (manufactured by Berthold). The correlation between the maximum luminescence intensity (Imax) and the protein concentration is shown in FIG. 9. The linear correlation was observed between the luminescence intensity and the biotinylated hgA-Gaussia luciferase. The results reveal that the amount of the biotinylated hgA-Gaussia luciferase can be quantitatively determined by luminescence.

Example 12

Luminescent Immunoassay of α-Fetoprotein (AFP) Using Biotinylated hg-Gaussia Luciferase 1) Coating of Anti-Fetoprotein Antibody (Anti-AFP Antibody)

The anti-AFP antibody (6D2) was prepared in a concentration of 5 µg/ml, using 50 mM carbonate buffer solution (pH 9.6) containing 0.05% sodium azide. The solution was dispensed into a 96-well microplate (manufactured by Nunc, #437796) in an amount of 100 µl/well and allowed to stand at room temperature overnight for coating. After the standing, the carbonate buffer solution was withdrawn and the post-coating solution was dispensed in an amount of 200 µl/well, which was then allowed to stand at 4° C. overnight.

2) Detection of AFP by Biotinylated hgA-Gaussia Luciferase

Figure 10:
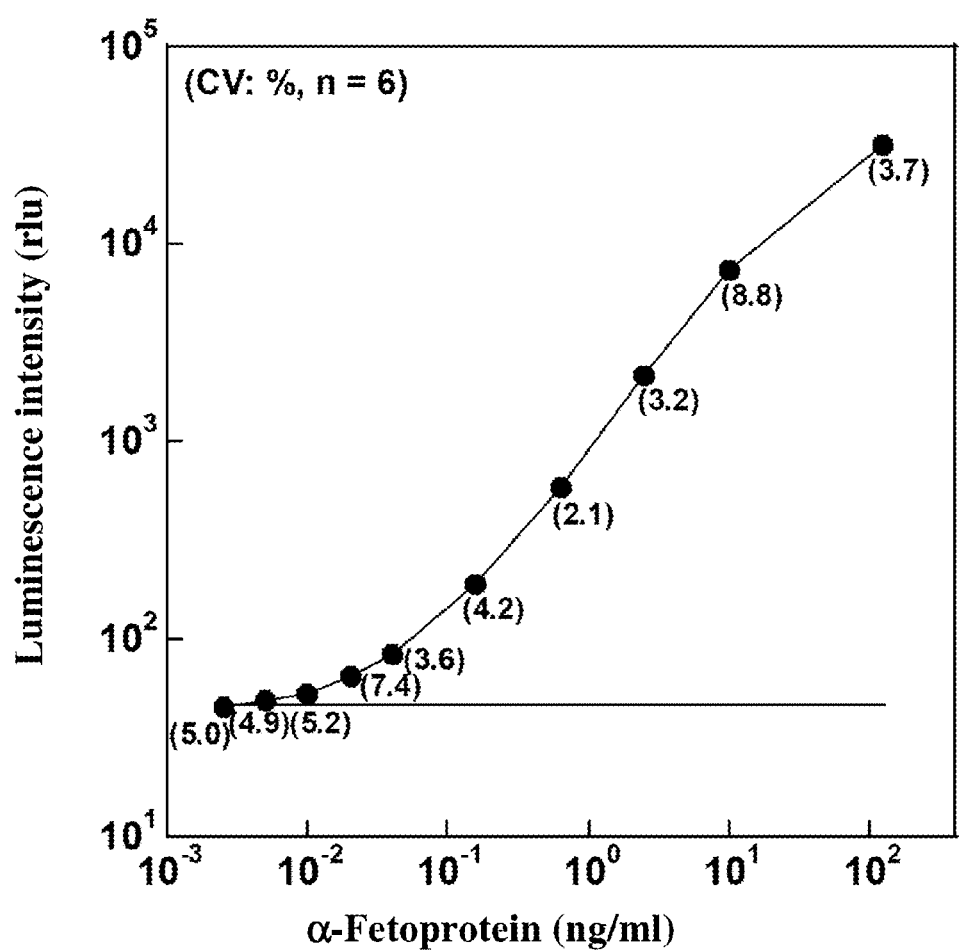
FIG. 10 shows the standard curve of AFP obtained using biotinylated hgA-Gaussia luciferase, wherein the solid line represents the background concentration, indicating a mean value+3SD when the concentration of AFP is 0 ng/ml.

After the standing, the post-coating solution was removed. The wells were washed 3 times with 340 µl of TBST-E. AFP, which was diluted in a range from 0.0125 ng/ml to 125 ng/ml with TBS containing 10% Block Ace and 2 mM EDTA, was dispensed into a 96-well microplate in an amount of 50 µl/well. The biotinylated anti-AFP antibody (1D5) diluted to 74.5 ng/ml was further dispensed in an amount of 50 µl/well, which was then allowed to stand at 30° C. for an hour. The reaction solution was withdrawn from the plate described above and the wells were washed 3 times with 340 µl of TBST-E. Next, 50 µl of streptavidin diluted to 200 µmol/ml with PBSE-TB was mixed with 50 µl of the biotinylated hgA-Gaussia luciferase diluted to 400 µmol/ml. The mixture was reacted at room temperature for 30 minutes. Thereafter, the solution diluted to 80-fold with PBSE-TB was dispensed onto the plate above in an amount of 100 µl/well, followed by allowing to stand at 30° C. for 30 minutes. The reaction solution was removed and the wells were washed 3 times with 340 µl of TBST-E. Then, substrate coelenterazine diluted to 0.5 ng/µl with PBST-E was injected into the wells in an amount of 100 µl/well. The luminescence intensity was measured on an apparatus for measuring luminescence Centro LB960 for 10 seconds in 0.1 second intervals to determine the maximum luminescence intensity (Imax). The standard curve of AFP obtained from the Imax and AFP concentration is shown in FIG. 10.

Example 13

Preparation of hgA-Gaussia Luciferase-Labeled Antibody

1) Preparation of Sulfhydryl Reactive Antibody (Maleimidated Antibody) (Conjugation of Anti-AFP Antibody and Crosslinking Reagent having Maleimide Group)

To a solution of 50 µg (0.3 nmol) of the anti-AFP antibody (manufactured by Japan Clinical Laboratories, Inc., Clone No. 1D5, subclass IgG1-κ, hereinafter referred to as "1D5") in 78.3 µl of 66 mM phosphate buffered saline containing 0.1 mM EDTA (pH 7.4, hereinafter referred to as "buffer A"), 3 µl of sulfosuccinimidyl 4-(N-maleimidomethyl)cyclohexane-1-carboxylate (sulfo-SMCC, PIERCE) was added (sulfo-SMCC, 3 nmol, 1D5/sulfo-SMCC=1/10). The mixture was reacted at 4° C. for 2 hours. After completion of the reaction, 1 µl (10 nmol) of 10 mM glycine was added to the reaction mixture and allowed to stand at 25° C. for at least 10 minutes to stop the reaction. The inactivated sulfo-SMCC was removed by centrifugation (manufactured by Hitachi, CR20B2) at 4° C. and 6,000 rpm for 15 minutes using an Amicon Ultra-4 Spin Column (manufactured by Millipore; molecular weight cutoff, 10,000) to give the conjugate of anti-AFP antibody and the crosslinking reagent having the maleimide group (hereinafter sometimes referred to as "maleimidated 1D5"). The recovery rate of the maleimidated 1D5 as calculated from $E^{1\%}_{280\ nm}$=14 was 70.6% (0.24 nmol, 35.3 µg).

2) Reaction of hgA-GL with Sulfhydryl Reactive Antibody (Maleimidated 1D5)

To 0.24 nmol of the maleimidated 1D5, 0.72 nmol of the purified hgA-Gaussia luciferase (hereinafter sometimes referred to as "hgA-GL") was added. The mixture was reacted at 4° C. overnight. After completion of the reaction, 1 µl (10 nmol) of 10 mM cysteine aqueous solution was added to the reaction mixture to give the conjugate of hgA-GL and the maleimidated 1D5 (hereinafter sometimes referred to as "hgA-GL-Ab1D5").

The hgA-GL-Ab1D5 retained the luminescence activity of 96%, without significant loss of the luminescence activity. The hgA-GL-Ab1D5 obtained was applied to SDS-PAGE analysis on a 12% separation gel under reducing conditions. As a result, a band was detected at 84 kDa, indicating the formation of conjugate of hgA-GL (29 kDa) with a heavy chain (55 kDa) of 1D5.

Example 14

Quantitative Property of hgA-GL-Ab1D5

Figure 11:
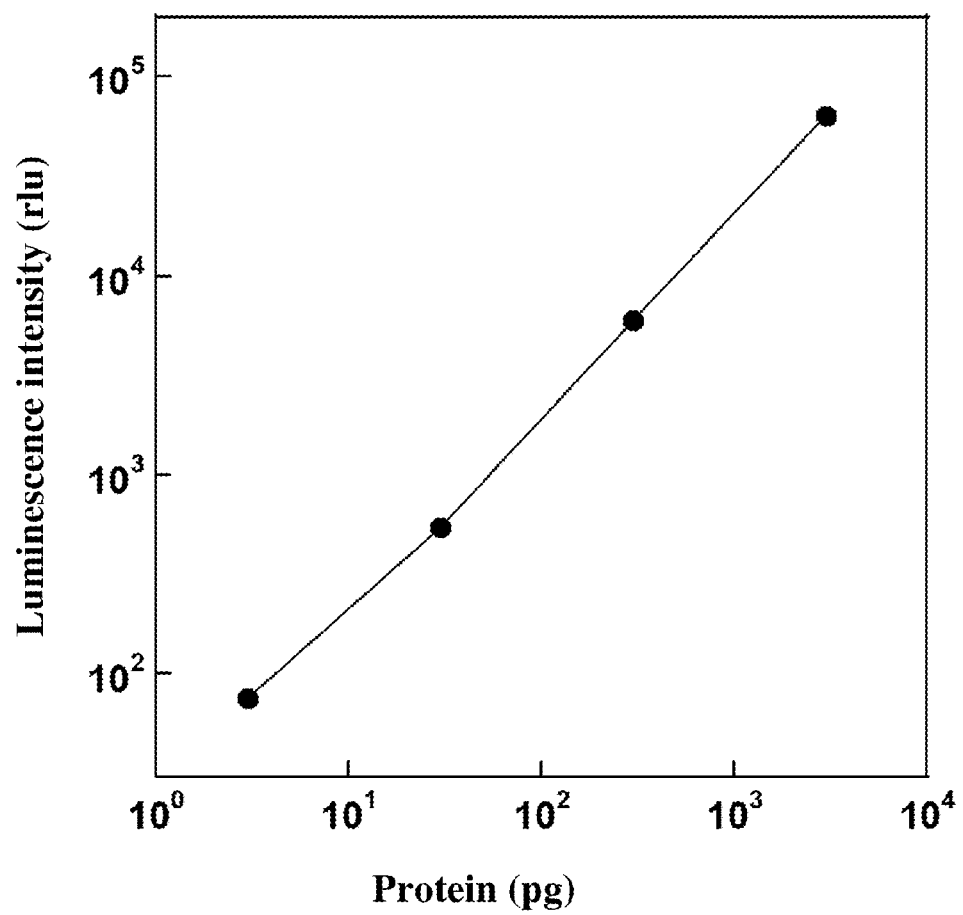
FIG. 11 shows the relationship between the concentration of hgA-GL-Ab1D5 and the luminescence intensity.

In order to use hgA-GL-Ab1D5 as a detection probe, it is required that the protein concentration and the luminescence activity are in a linear correlation. The concentration of hgA-GL-Ab1D5 was diluted in a range from 3 picograms to 3,000 picograms, 100 µl of substrate coelenterazine (0.5 ng/µl) was injected, and the luminescence activity was measured with an apparatus for measuring luminescence Centro LB960 (manufactured by Berthold). The correlation between the maximum luminescence intensity (Imax) and the protein concentration is shown in FIG. 11. The linear correlation was observed between the luminescence intensity and hgA-GL-Ab1D5. The results reveal that the amount of hgA-GL-Ab1D5 can be quantitatively determined by luminescence.

Example 15

Luminescent Immunoassay of AFP Using hgA-GL-Ab1D5

1) Coating of Anti-AFP Antibody

The anti-AFP antibody (Clone No. 6D2, subclass IgG2a-κ, manufactured by Japan Clinical Laboratories, Inc., hereinafter sometimes referred to as "6D2") was prepared in a concentration of 5 µg/ml, using 50 mM carbonate buffer solution (pH 9.6) containing 0.05% sodium azide. The solution was dispensed into a 96-well microplate (manufactured by Nunc, #437796) in an amount of 100 µl/well and allowed to stand at 25° C. overnight for coating.

2) Post-Coating

After the standing, the carbonate buffer solution was withdrawn and a solution of 150 mM NaCl (Wako Pure Chemical Industry) and 20 mM Tris-HCl (Wako Pure Chemical Industry) (hereinafter referred to as TBS) containing 1% bovine serum albumin (Sigma), 2 mM EDTA (EDTA.2Na, Dojin Chemical Laboratory) and 0.05% sodium azide (Wako Pure Chemical Industry) (hereinafter referred to as a post-coating solution) was dispensed in an amount of 200 μl/well, which was then allowed to stand at 4° C. overnight.

3) Reaction of AFP with hgA-GL-Ab1D5

The post-coating solution was removed. After the wells were washed 3 times with 340 μl of TBST-E, 110 μg/ml of AFP (Dako) was diluted in TBS containing 10% Block Ace (Dainippon Pharmaceutical) and 5 mM EDTA (hereinafter referred to as diluent) to prepare a serial dilution from 10 pg/ml to 200 ng/ml. The dilution was dispensed in an amount of 50 μl/well. Furthermore, hgA-GL-Ab1D5 diluted to 74.5 ng/ml with the diluent was dispensed in an amount of 50 μl/well, which was then allowed to stand at 25° C. for an hour.

4) Measurement of Luminescence

After the standing, the reaction solution was removed and the wells were washed 3 times with 340 μl of TBST-E. Then, substrate coelenterazine diluted to 0.5 ng/μl with PBST-E was injected into the wells in an amount of 100 μl/well. The luminescence intensity was measured on an apparatus for measuring luminescence Centro LB960 (manufactured by Berthold) for 10 seconds in 0.1 second intervals to determine the maximum luminescence intensity (Imax).

Figure 12:
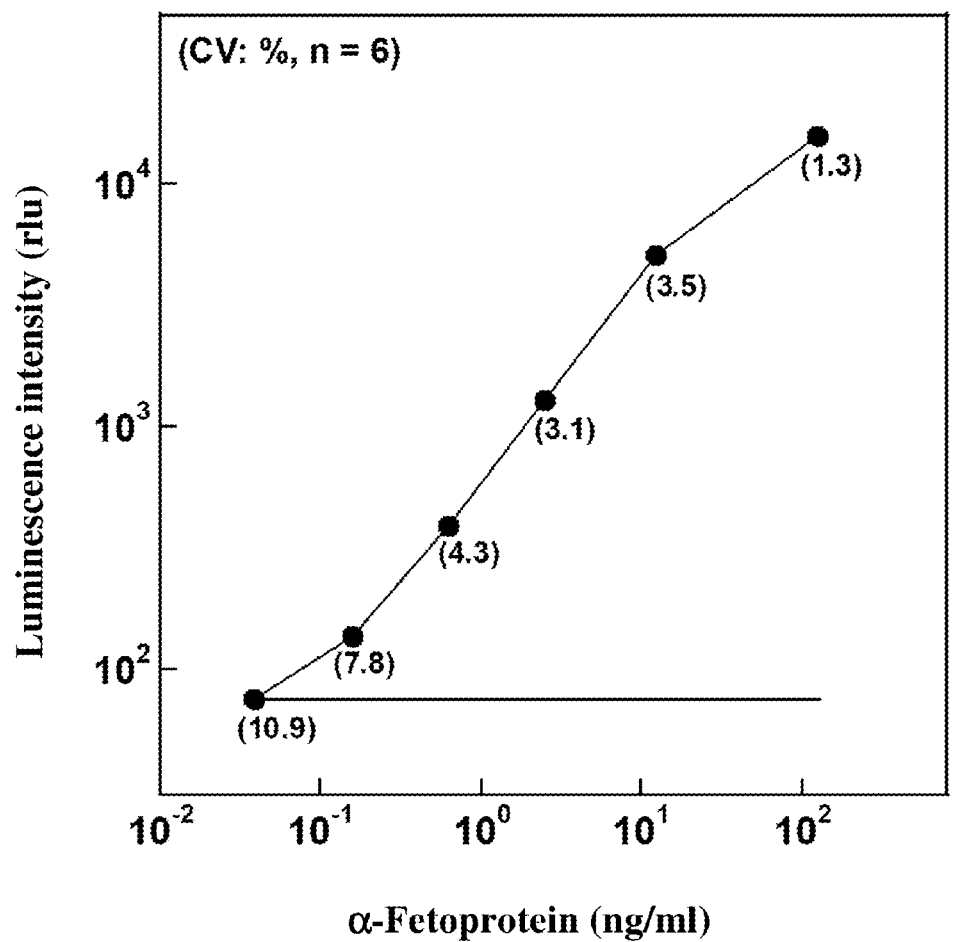
FIG. 12 shows the standard curve of AFP obtained using hgA-GL-Ab1D5, wherein the solid line represents the background concentration, indicating a mean value+3SD when the concentration of AFP is 0 ng/ml.

The standard curve of AFP obtained by bioluminescent immunoassay using hgA-GL-Ab1D5 is shown in FIG. 12. The results revealed that the detection limit of AFP was $4 \times 10^{-2}$ ng/ml and the dynamic range was $4 \times 10^{-2}$ to $10^2$ ng/ml, indicating that hgA-GL-Ab1D5 is excellent for immunoassays.

Example 16

Preparation of Fluorescence-Labeled Gaussia Luciferase

After 2.2 nmol of purified hg-Gaussia luciferase was dissolved in 1 ml of 10 mM EDTA-containing PBS (manufactured by Sigma; 0.137 M sodium chloride and 0.0027 M potassium chloride, pH 7.4), the mixture was added to 22 nmol of a solution of fluorescein-5-maleimide (manufactured by Pierce) in dimethylformamide. The mixture was then reacted at 4° C. for 16 hours. The reaction solution was centrifuged at 4° C. and 6,000 rpm for 10 minutes using an Amicon Ultra-4 Spin Column (manufactured by Millipore; molecular weight cutoff, 10,000). After concentration, the column was washed twice with 2 ml of PBS solution containing 10 mM EDTA and 0.01% Tween 20 and the total volume was made 1 ml. The recovery rate of the fluorescence-labeled Gaussia luciferase activity was 92%.

Example 17

Figure 13:
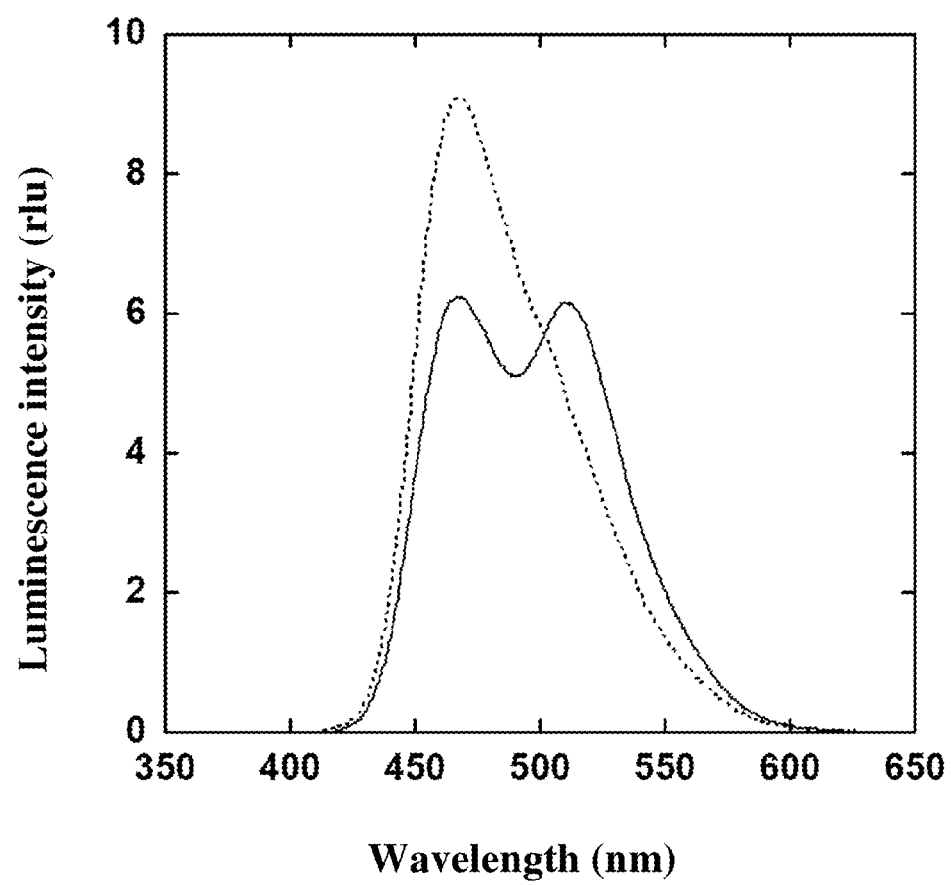
FIG. 13 shows the bioluminescence energy transfer by fluorescence-labeled Gaussia luciferase, wherein the dotted line represents the luminescence spectra of Gaussia luciferase and the solid line represents the luminescence spectra of fluorescence-labeled Gaussia luciferase.

Bioluminescence Resonance Energy Transfer (BRET) by Fluorescence-Labeled Gaussia Luciferase After 5 μg of coelenterazine dissolved in 5 μl of ethanol was added to 0.99 ml of PBS solution containing 10 mM EDTA and 0.01% Tween 20, 5 μl of the fluorescence-labeled Gaussia luciferase (1 μg) was added to the mixture to initiate a luminescence reaction. At the same time, luminescence emission spectra were measured on a Jasco FP-6500 (manufactured by JASCO Corporation) with the excitation light source turned off. The measurement was performed under the conditions: emission band width, 20 nm; response, 0.2 second; scan speed, 2000 nm/min at 22 to 25° C., using a quartz cuvette (10 mm light path). The results of the measured spectra are shown in FIG. 13. Light emission by Gaussia luciferase alone exhibits only the maximum at 467 nm; with the fluorescence-labeled Gaussia luciferase, a new peak is formed at 510 nm. This is because the luminescence energy produced as a result of the oxidation of coelenterazine by Gaussia luciferase occurs as a result of the energy transfer to a fluorescent dye fluorescein bound to Gaussia luciferase. The energy transfer efficiency is estimated to be approximately 50%.

Reference Example 1

Construction of Gaussia Luciferase-Apoaequorin-S142C Expression Vector

The Gaussia luciferase-apoaequorin-S142C fused gene expression vector having the Gaussia luciferase gene and the apoaequorin-S142C gene wherein the serine residue 142 of apoaequorin was replaced with cysteine residues was constructed as follows.

The Gaussia luciferase gene (hGL gene) was prepared from Gaussia luciferase gene-bearing pcDNA3-hGL (manufactured by LUX) by PCR. The apoaequorin-S142C gene wherein the serine residue 142 of apoaequorin was replaced with cysteine residues was prepared by PCR using pAM-HE obtained by subcloning the HindIII-EcoRI fragment of apoaequorin gene-bearing pAQ440 (cf., JPA 61-135586) into pUC9 vector. pCold II (Takara-Bio) was used as the expression vector.

The serine residue 142 of apoaequorin was replaced with cysteine residues according to the following procedures. Using pAM-HE as a template, PCR was performed (cycle conditions, 25 cycles; 1 min/94° C., 1 min/50° C. and 1 min/72° C.) with a PCR kit (manufactured by Takara-Bio) using the following two primers: AQ-20N/XhoI and AQ-S 142C-R, to amplify the desired DNA region.

AQ-20N/XhoI (5' ccg CTCGAG ACA TCA GAC TTC GAC AAC CCA 3'; the XhoI restriction enzyme site underlined) (SEQ ID NO: 21),

AQ-S142C-R(5' ATC TTC GCA TGA TTG GAT GAT 3') (SEQ ID NO: 22).

Similarly, PCR was performed (cycle conditions, 25 cycles; 1 min/94° C., 1 min/50° C. and 1 min/72° C.) with a PCR kit (manufactured by Takara-Bio) using the following two primers: AQ-S 142C-F and AEQ-C-PstI, to amplify the desired DNA region.

AQ-S142C-F (5' CAA TCA TGC GAA GAT TGC GAG 3') (SEQ ID NO: 23),

AEQ-C-PstI (5' cgg CTG CAGTTA GGG GAC AGC TCC ACC GTA GAG CTT 3'; the PstI restriction enzyme site underlined) (SEQ ID NO: 24)

Using the two PCR products obtained as templates, PCR was performed (cycle conditions, 25 cycles; 1 min/94° C., 1 min/50° C. and 1 min/72° C.) with a PCR kit (manufactured by Takara-Bio) using PCR primers: AQ-20N/XhoI (SEQ ID NO: 21) and AEQ-C-PstI (SEQ ID NO: 24) to give the apoaequorin gene with the cysteine residues replaced for the serine residue 142. The fragment obtained was purified by a PCR purification kit (manufactured by Qiagen). After digestion with restriction enzymes XhoI/PstI in a conventional manner, the fragment was ligated to pBluescript II SK (+) (Stratagene) at the restriction enzyme XhoI/PstI sites to construct the vector pBlue-AQ-S 142C.

Subsequently, PCR was performed (cycle conditions, 25 cycles; 1 min/94° C., 1 min/50° C. and 1 min/72° C.) for the Gaussia gene with a PCR kit (manufactured by Takara-Bio) using pcDNA3-hGL (manufactured by Prolume Ltd.) as a template and using the following two primers: GL-25N/Kpn-EcoRI and GL-24N-TAA/XhoI to amplify the Gaussia gene.

GL-25N/Kpn-EcoRI (5' ggc GGTACC GAA TTC AAG CCC ACC GAG AAC AAC 3'; the Asp718I restriction enzyme site underlined) (SEQ ID NO: 25), GL-24N-TAA/XhoI(5' ccg CTCGAG GTC ACC ACC GGC CCC CTT GAT 3'; the XhoI restriction enzyme site underlined) (SEQ ID NO: 26)

The fragment obtained was purified by a PCR Purification Kit (manufactured by Qiagen). After digestion with restriction enzymes Asp718I/XhoI in a conventional manner, the fragment was ligated to pBlue-AQ-S142C at the restriction enzyme Asp718I/XhoI sites to construct the vector pBlue-GL-AQ-S142C.

Figure 14:
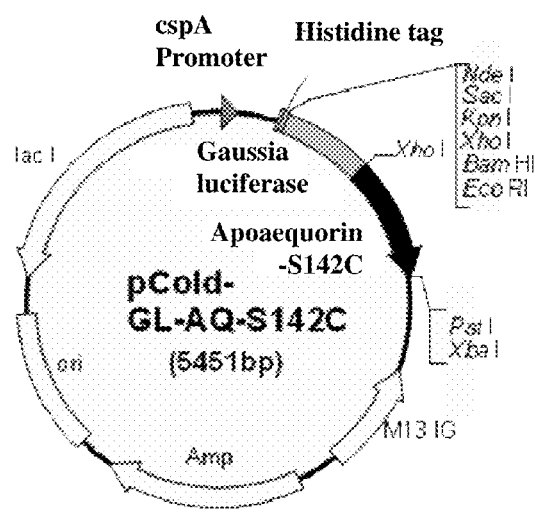
FIG. 14 shows the expression vector (pCold-GL-AQ-S 142C) for Gaussia luciferase-apoaequorin-S 142C and the fusion protein expressed; (a) is a schematic view of the expression vector and (b) is a schematic view of the amino acid sequence for the fusion protein expressed.

The vector pBlue-GL-AQ-S142C was digested with restriction enzymes EcoRI/PstI in a conventional manner and then ligated to pColdII at the restriction enzyme EcoRI/PstI sites to construct the expression vector pCold-GL-AQ-S142C (FIG. 14). The insert DNA was confirmed by nucleotide sequencing on a DNA Sequencer (manufactured by ABI).

The nucleotide sequence of the insert DNA is shown by SEQ ID NO: 27, and the amino acid sequence of a fusion protein encoded by the insert DNA is shown by SEQ ID NO: 28.

Reference Example 2

Purification of Recombinant Gaussia Luciferase-Aequorin-S142C Fusion Protein

The recombinant Gaussia luciferase-aequorin-S142C fusion protein was obtained as follows. The recombinant Gaussia luciferase-aequorin-S142C was expressed in *E. coli* using the expression vector pCold-GL-AQ-S142C and purified by nickel-chelate column chromatography, whereby the apoaequorin part is regenerated to give the recombinant Gaussia luciferase-aequorin-S142C.

1) Expression of Recombinant Gaussia Luciferase-Apoaequorin-S142C in *E. Coli*

The expression vector pCold-GL-AQ-S142C for the Gaussia luciferase-apoaequorin-S142C gene was used to express the recombinant Gaussia luciferase-apoaequorin-S142C in *E. coli*. This vector was introduced into the *E. coli* BL21 strain in a conventional manner. The transformant obtained was inoculated in 10 ml of LB liquid medium (10 g of bactotryptone, 5 g of yeast extract and 5 g of sodium chloride per 1 liter of water, pH 7.2) containing ampicillin (50 μg/ml), followed by incubation at 37° C. for 18 hours. Next, the culture broth was added to 400 ml×5 tubes of fresh LB liquid medium (2 L in total) and incubated at 37° C. for 5 hours. After cooling in an ice water, isopropyl-β-D(-)-thiogalactopyranoside (IPTG, manufactured by Wako Pure Chemical Industry) was added to the culture to a final concentration of 0.2 mM, followed by incubation at 15° C. for further 17 hours. After completion of the incubation, the cells were recovered by centrifugation (5,000 rpm, 5 mins.) and provided for use as the starting material for protein extraction.

2) Extraction of Gaussia Luciferase-Apoaequorin-S142C from Cultured Cells

The cultured cells collected were suspended in 100 ml of 50 mM Tris-HCl (pH 7.6) and disrupted by ultrasonication (manufactured by Branson, Sonifier Model Cycle 250) 3 times each for 3 minutes under ice cooling. The cell lysate was centrifuged at 10,000 rpm (12,000×g) at 4° C. for 20 minutes to give soluble fractions. The resultant soluble fractions were suspended in 100 ml of 50 mM Tris-HCl (pH 7.6) containing 6 M urea. The suspension was subjected to ultrasonic treatment under ice cooling, followed by centrifugation at 10,000 rpm (12,000×g) and 4° C. for 10 minutes. The urea soluble fraction obtained was used as the starting material for purification of the Gaussia luciferase-apoaequorin-S142C.

3) Purification of Recombinant Gaussia Luciferase-Apoaequorin-S142C from the Urea Soluble Fraction The recombinant expression protein has 6 histidine sequences at the amino terminus and can be purified by affinity chromatography on a nickel-chelate gel.

First, the 6M urea soluble fraction was applied on a nickel-chelate column (Amersham Bioscience, column size: diameter 2.5×6 cm) equilibrated with 50 mM Tris-HCl (pH 7.6) containing 6M urea to adsorb the Gaussia luciferase-apoaequorin-S142C. The column adsorbed with the Gaussia luciferase-apoaequorin-S142C was washed with 150 ml of 50 mM Tris-HCl (pH 7.6) containing 6M urea. The Gaussia luciferase-apoaequorin-S142C was then eluted by 50 mM Tris-HCl (pH 7.6) containing 6M urea and 0.1M imidazole (manufactured by Wako Pure Chemical Industry). Protein concentration was determined by the method of Bradford using a commercially available kit (manufactured by Bio-Rad) and bovine serum albumin (manufactured by Pierce) as a standard. From 2 L of the cultured cells, 106 mg of the Gaussia luciferase-apoaequorin-S142C was obtained.

4) Preparation of Gaussia Luciferase-aequorin-S142C from Gaussia Luciferase-Apoaequorin-S142C Regeneration of the Gaussia luciferase-aequorin-S142C from Gaussia luciferase-apoaequorin-S142C was carried out as follows. First, the Gaussia luciferase-apoaequorin-S142C was treated with a reducing agent, 2-mercaptoethanol, and then contacted with a luminescent substrate (coelenterazine) to regenerate aequorin. Thereafter, the reducing agent was removed by a dialysis treatment. Gaussia luciferase was converted into its active form by refolding to give the Gaussia luciferase-aequorin-S142C protein having the Gaussia luciferase activity and the aequorin activity.

Specifically, the Gaussia luciferase-apoaequorin-S142C solution (50 μg/10 eluted by 0.1 M imidazole and 6 M urea from the nickel-chelate column was dissolved in 990 μl of 30 mM Tris-HCl (pH 7.6) containing 10 mM EDTA. The solution was mixed with 2-mercaptoethanol in a final concentration of 0.35% (v/v). After the mixture was allowed to stand at 37° C. for 30 minutes, it was confirmed that the luminescence activity of Gaussia luciferase was inactivated. A solution of 5 μg of substrate coelenterazine (1 μg/μl) in ethanol was added and a reaction for regeneration of aequorin was carried out at 4° C. overnight. Next, the solution of the regenerated aequorin obtained was dialyzed at 4° C. overnight with 4 L of 100 mM ammonium carbonate solution (pH 8.0) containing 10 mM EDTA to give the recombinant Gaussia luciferase-aequorin-S142C protein (40 μg).

Example 18

Comparison of Luminescence Activity

With respect to hg-Gaussia luciferase obtained by the method described in EXAMPLE 5 3) above, hgA-Gaussia luciferase obtained by the method described in EXAMPLE 6 3) above and the recombinant Gaussia luciferase-aequorin-S142C protein obtained by the method described in REFERENCE EXAMPLE 2 4) above, the luminescence activity was compared between the respective fusion proteins. Specifically, the luminescence activity between the respective fusion proteins was compared according to modifications of the method described in EXAMPLE 5 5). The results are shown in TABLE 3 below.

From TABLE 3, it is found that hg-Gaussia luciferase and hgA-Gaussia luciferase in which the number of amino acid residues in the portion between the first region and the C terminus except for the first region is 21 to 36 residues show the specific luminescence activity higher by approximately 500 times than the recombinant Gaussia luciferase-aequorin-S142C protein in which the number of amino acid residues in the portion between the first region and the C terminus except for the first region is 188 residues.

TABLE 3

Comparison of Luminescence Activity between Respective Fusion Proteins

| Fusion protein | Number of amino acids in the first region | Number of amino acids in the second region | Number of amino acids in the portion between the first region and the C terminus except for the first region | Number of cysteines in the first region/ number of cysteines in the second region | Specific luminescence activity ($10^7$ rlu/mg) |
|---|---|---|---|---|---|
| Hg-Gaussia luciferase | 168 | 15 | 21 (2* + 15 + 4*) | 10/1 | 1055 |
| hgA-Gaussia luciferase | 168 | 15 | 36 (2* + 15 + 2* + 15 + 2*) | 10/1 | 957 |
| Recombinant Gaussia luciferase-aequorin-S142C protein | 168 | 186 | 188 (2* + 186) | 10/4 | 2 |

Symbol * denotes linker sequences for the restriction enzyme sites.

Based on EXAMPLES above, it is found that the luciferase (fusion protein) of the invention exhibits a high catalytic ability for a luminescence activity. It is also found that, since the luciferase is capable of binding to other useful substances (fluorescent substances; ligands such as biotin, antibodies, etc.) via the thiol group of cysteines introduced into the luciferase of the invention, the luciferase can be utilized for the bioluminescence energy transfer or the detection of substances specific to ligands.

Sequence Listing Free Text
SEQ ID NO: 1
　DNA sequence of the expression vector pPICZα-hgLinker having a hinge sequence and a multicloning site, prepared in EXAMPLE 1
SEQ ID NO: 2
　Amino acid sequence of the protein encoded by the DNA sequence of the expression vector pPICZα-hgLinker having a hinge sequence and a multicloning site, prepared in EXAMPLE 1
SEQ ID NO: 3
　DNA sequence encoding the hg-Gaussia luciferase fusion protein inserted into the expression vector pPICZα-hgGL-H prepared in EXAMPLE 2
SEQ ID NO: 4
　Amino acid sequence of the hg-Gaussia luciferase fusion protein inserted into the expression vector pPICZα-hgGL-H prepared in EXAMPLE 2
SEQ ID NO: 5
　DNA sequence encoding the hg-Gaussia luciferase fusion protein inserted into the expression vector pCold-hgGL prepared in EXAMPLE 3
SEQ ID NO: 6
　Amino acid sequence of the hg-Gaussia luciferase fusion protein inserted into the expression vector pCold-hgGL prepared in EXAMPLE 3
SEQ ID NO: 7
　DNA sequence encoding the hgA-Gaussia luciferase fusion protein inserted into the expression vector pCold-hgA-GL prepared in EXAMPLE 4
SEQ ID NO: 8
　Amino acid sequence of the hgA-Gaussia luciferase fusion protein inserted into the expression vector pCold-hgA-GL prepared in EXAMPLE 4
SEQ ID NO: 9
　Nucleotide sequence of the primer used in EXAMPLE 1
SEQ ID NO: 10
　Nucleotide sequence of the primer used in EXAMPLE 1
SEQ ID NO: 11
　Nucleotide sequence of the primer used in EXAMPLE 1
SEQ ID NO: 12
　Nucleotide sequence of the primer used in EXAMPLE 1
SEQ ID NO: 13
　Nucleotide sequence of the primer used in EXAMPLE 2
SEQ ID NO: 14
　Nucleotide sequence of the primer used in EXAMPLE 2
SEQ ID NO: 15
　Nucleotide sequence of the primer used in EXAMPLE 4
SEQ ID NO: 16
　Nucleotide sequence of the primer used in EXAMPLE 4
SEQ ID NO: 17
　DNA sequence encoding the catalytic domain of Gaussia luciferase
SEQ ID NO: 18
　Amino acid sequence of the catalytic domain of Gaussia luciferase
SEQ ID NO: 19
　DNA sequence encoding the hinge
SEQ ID NO: 20
　Amino acid sequence of the hinge
SEQ ID NO: 21
　Nucleotide sequence of the primer used in REFERENCE EXAMPLE 1
SEQ ID NO: 22
　Nucleotide sequence of the primer used in REFERENCE EXAMPLE 1
SEQ ID NO: 23
　Nucleotide sequence of the primer used in REFERENCE EXAMPLE 1
SEQ ID NO: 24
　Nucleotide sequence of the primer used in REFERENCE EXAMPLE 1
SEQ ID NO: 25
　Nucleotide sequence of the primer used in REFERENCE EXAMPLE 1

SEQ ID NO: 26

Nucleotide sequence of the primer used in REFERENCE EXAMPLE 1

SEQ ID NO: 27

DNA sequence encoding the Gaussia luciferase-apoaequorin-S142C fusion protein, inserted into the expression vector pCold-GL-AQ-S142 prepared in REFERENCE EXAMPLE 1

SEQ ID NO: 28

Amino acid sequence of the Gaussia luciferase-apoaequorin-S142C fusion protein, inserted into the expression vector pCold-GL-AQ-S142 prepared in REFERENCE EXAMPLE 1

The invention claimed is:

1. A method for determining a substance that specifically binds to a ligand, which comprises binding a test substance via the ligand to a complex comprising a fusion protein comprising:
(1) a first region selected from the group consisting of (a) to (d) below:
   (a) a region consisting of the amino acid sequence of SEQ ID NO: 18;
   (b) a region consisting of the amino acid sequence of SEQ ID NO: 18 wherein 1 to 10 amino acids are deleted, substituted, inserted and/or added and having a catalytic ability for a luminescence activity with a luciferin which is a substrate;
   (c) a region consisting of an amino acid sequence having at least 90% homology to the amino acid sequence of SEQ ID NO: 18 and having a catalytic ability for a luminescence activity with a luciferin which is a substrate; and,
   (d) a region consisting of an amino acid sequence encoded by a polynucleotide which hybridizes under high stringent conditions to a polynucleotide consisting of a nucleotide sequence complementary to the nucleotide sequence of SEQ ID NO: 17 and having a catalytic ability for a luminescence activity with a luciferin which is a substrate, wherein the high stringent conditions are 5×SSC, 5×Denhardt's solution, 0.5% (w/v) SDS, 50% (v/v) formamide and 50° C.; and,
(2) a second region consisting of an amino acid sequence for a polypeptide having at least one cysteine residue for binding to other useful compound via its thiol group, wherein the second region is selected from the group consisting of (e) to (h) below:
   (e) a region consisting of the amino acid sequence of SEQ ID NO: 20;
   (f) a region comprising the amino acid sequence of SEQ ID NO: 20 wherein 1 to 3 amino acids are deleted, substituted, inserted and/or added and having at least one cysteine residue for binding to other useful compound via the thiol group;
   (g) a region comprising an amino acid sequence having at least 90% homology to the amino acid sequence of SEQ ID NO: 20 and having at least one cysteine residue for binding to other useful compound via the thiol group; and,
   (h) a region comprising an amino acid sequence encoded by a polynucleotide which hybridizes under high stringent conditions to a polynucleotide consisting of a nucleotide sequence complementary to the nucleotide sequence of SEQ ID NO: 19 and having at least one cysteine residue for binding to other useful compound via the thiol group, wherein the high stringent conditions are 5×SSC, 5×Denhardt's solution, 0.5% (w/v) SDS, 50% (v/v) formamide and 50° C.; and a ligand bound to the fusion protein via the thiol group of the cysteine residue in the second region and detecting light being emitted from the fusion protein in the presence of a luciferin to determine the substance.

2. The method according to claim 1, wherein:
(1) the first region is a region consisting of the amino acid sequence of SEQ ID NO: 18, and,
(2) the second region is a region consisting of the amino acid sequence of SEQ ID NO: 20.

3. The method according to claim 1, wherein the fusion protein further comprises an amino acid sequence for promoting translation and/or an amino acid sequence for purification.

4. The method according to claim 1, wherein the fusion protein consisting of an amino acid sequence of SEQ ID NO: 4, 6 or 8.

* * * * *